United States Patent
Forgione et al.

(10) Patent No.: US 11,034,702 B2
(45) Date of Patent: Jun. 15, 2021

(54) THIENOISOQUINOLINES AND THEIR DERIVATIVES FOR THE TREATMENT OF CANCER

(71) Applicant: VALORBEC, SOCIÉTÉ EN COMMANDITE, Montréal (CA)

(72) Inventors: Pasquale Forgione, Montréal (CA); Alisa Julienne Piekny, Lachine (CA); Dilan Boodhai Jaunky, Montréal (CA); Fei Chen, Pierrefonds (CA); Jiang Tian Liu, Montréal (CA)

(73) Assignee: VALORBEC, SOCIÉTÉ EN COMMANDITE, Montréal (CA)

( * ) Notice: Subject to any disclaimer, the term of this patent is extended or adjusted under 35 U.S.C. 154(b) by 0 days.

(21) Appl. No.: 16/465,966

(22) PCT Filed: Dec. 6, 2017

(86) PCT No.: PCT/CA2017/051473
§ 371 (c)(1),
(2) Date: May 31, 2019

(87) PCT Pub. No.: WO2018/102920
PCT Pub. Date: Jun. 14, 2018

(65) Prior Publication Data
US 2020/0024284 A1    Jan. 23, 2020

Related U.S. Application Data

(60) Provisional application No. 62/430,387, filed on Dec. 6, 2016.

(51) Int. Cl.
*C07D 495/04* (2006.01)
*A61P 35/00* (2006.01)
*C07D 471/04* (2006.01)
*C07D 491/048* (2006.01)
*C07D 495/14* (2006.01)

(52) U.S. Cl.
CPC .......... *C07D 495/04* (2013.01); *A61P 35/00* (2018.01); *C07D 471/04* (2013.01); *C07D 491/048* (2013.01); *C07D 495/14* (2013.01)

(58) Field of Classification Search
CPC ... A61P 35/00; C07D 471/04; C07D 491/048; C07D 495/14
USPC ........................................................ 546/80
See application file for complete search history.

(56) References Cited

U.S. PATENT DOCUMENTS

| | | | |
|---|---|---|---|
| 7,696,221 B2 | 4/2010 | Coghlan et al. | |
| 2006/0058337 A1* | 3/2006 | Steffan | C07D 221/12 514/298 |
| 2007/0203224 A1* | 8/2007 | Neamati | C07D 339/06 514/424 |
| 2010/0216772 A1* | 8/2010 | Pegoraro | C07D 221/12 514/212.04 |
| 2011/0301133 A1* | 12/2011 | Wu | A61P 7/02 514/171 |

FOREIGN PATENT DOCUMENTS

| | | |
|---|---|---|
| WO | 2006069182 | 6/2006 |
| WO | 2014056567 | 4/2014 |

OTHER PUBLICATIONS

Dorwald; "Side Reactions in Organic Synthesis", Wiley-VCH, 2005: front matter; pp. I-XV and chapter 1; pp. 1-16. (Year: 2005).*
Extended European Search Report in Application 17878226, dated Nov. 26, 2019, 6 pages. (Year: 2019).*
Jaunky et al., "Abstract 3808: Novel compound conferring selectivity for cancer cell", published on Jul. 15, 2016.
English Translation—Machine Generated of WO2014056567(A1), "Materials for Organic Electroluminescent Devices", published on Apr. 17, 2014.
Hay et al., "Clinical development success rates for investigational drugs", Nature Biotechnology, vol. 32, No. 1, Jan. 2014, pp. 40-51.
Pearce et al., "An Empirical Process for the Design of High-Throughput Screening Deck Filters", J. Chem. Inf. Model. Apr. 5, 2006, 46, 1060-1068.
Baell et al., "New Substructure Filters for Removal of Pan Assay Interference Compounds (PAINS) from Screening Libraries and for Their Exclusion in Bioassays", J. Med. Chem. Feb. 4, 2010, 53, 2719-2740.
Lagorce et al., "FAF-Drugs2: Free ADME/tox filtering tool to assist drug discovery and chemical biology projects", BMC Bioinformatics 2008, 9:396, Published: Sep. 24, 2008.

(Continued)

*Primary Examiner* — Daniel R Carcanague
(74) *Attorney, Agent, or Firm* — Bereskin & Parr LLP/S.E.N.C.R.L., s.r.l.

(57) ABSTRACT

The present disclosure relates to fused N-arylsulfonamidyl-thienoisoquinoline compounds, derivatives and pharmaceutical compositions thereof, and methods and uses in inhibiting cancer cell growth, along with a supplemental anti-cancer agent. Centrosome targeting and microtubule depolymerisation are attractive in designing the present chemotherapeutic compounds. The various diseases and conditions treated include various types of cell cancers, and in vitro inhibition.

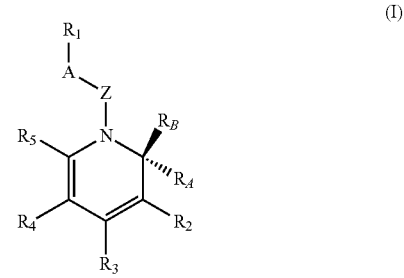

(I)

14 Claims, 27 Drawing Sheets

(56) References Cited

OTHER PUBLICATIONS

Kazius et al., "Derivation and Validation of Toxicophores for Mutagenicity Prediction", J. Med. Chem. 2005, 48, 312-320. Published on Dec. 17, 2004.
Bruns et al., "Rules for Identifying Potentially Reactive or Promiscuous Compounds", J. Med. Chem. Oct. 12, 2012, 55, 9763-9772.
Mukheijee et al., "Quinolines: a new hope against inflammation", Drug Discovery Today, vol. 18, Nos. 7/8, Apr. 2013.
Mukheijee et al., "Medicinal Chemistry of Quinolines as Emerging Anti-inflammatory Agents: An Overview", Current Medicinal Chemistry, 2013, 20, 4386-4410. (The year of publication is sufficiently earlier than the effective U.S. filing date so that the particular month of publication is not an issue).
Beccalli et al., "Microwave-Assisted Intramolecular Cyclization of Electron-Rich Heterocycle Derivatives by a Palladium-Catalyzed Coupling Reaction", Synthesis 2008, No. 1, pp. 0136-0140. Revised: Oct. 9, 2007.
Wong et al., "A One-Pot Double C—H Activation Palladium Catalyzed Route to a Unique Class of Highly Functionalized Thienoisoquinolines", Organic Letters, Apr. 13, 2012, vol. 14, No. 11, 2738-2741.
Chen et al., "One-Pot tandem Palladium-Catalyzed Decarboxylative Cross-Coupling and C—H Activation Route to Thienoisoquinolines", Adv. Synth. Catal. Apr. 15, 2014, 356, 1725-1730.
Chan et al., "Mitosis-targeted anti-cancer therapies: where they stand", Cell Death and Disease (Oct. 18, 2012) 3, e411.
Parker et al., "Microtubules and their role in cellular stress in cancer", Frontiers in Oncology, Jun. 2014, vol. 4, 1-19.
Mogilner et al., "Towards a quantitative understanding of mitotic spindle assembly and mechanics", Journal of Cell Science 123 (20), 3435-3445, 2010. (The year of publication is sufficiently earlier than the effective U.S. filing date so that the particular month of publication is not an issue).
Sacristan et al., "Joined at the hip: kinetochores, microtubules, and spindle assembly checkpoint signaling", Trends in Cell Biology, Jan. 2015, vol. 25, No. 1, 21-28.
Topham et al., "Mitosis and apoptosis: how is the balance set?", Current Opinion in Cell Biology, Jul. 2013, 25:780-785.
Burgess et al., "Stressing mitosis to death", Frontiers in Oncology, Jun. 2014, vol. 4, Article 140, 1-7.
Zasadil et al., "Cytotoxicity of paclitaxel in breast cancer is due to chromosome missegregation on multipolar spindles", Sci Transl Med., Mar. 2014, 6(229), 1-24.
Hinchcliffe, "Centrosomes and the Art of Mitotic Spindle Maintenance", International Review of Cell and Molecular Biology, vol. 313 (2014), 179-217.
Gergely et al., "Multiple centrosomes: together they stand, divided they fall", Genes & Development 22:2291-2296 (2008). (The year of publication is sufficiently earlier than the effective U.S. filing date so that the particular month of publication is not an issue).
Godinho et al., "Causes and consequences of centrosome abnormalities in cancer", Philosophical Transactions of the Royal Society 369:20130467 (2014). (The year of publication is sufficiently earlier than the effective U.S. filing date so that the particular month of publication is not an issue).
Ogden et al., "Let's huddle to prevent a muddle: centrosome declusteringas an attractive anticancer strategy", Cell Death and Differentiation (Jun. 1, 2012) 19, 1255-1267.
Chan, "A Clinical Overview of Centrosome Amplification in Human Cancers", International Journal of Biological Sciences, Oct. 16, 2011; 7(8):1122-1144.
Kawamura et al., "Identification of novel small molecule inhibitors of centrosome clustering in cancer cells", Oncotarget, october, vol. 4, No. 10, Sep. 25, 2013.
Eke et al., "The Small Molecule Inhibitor QLT0267 Radiosensitizes Squamous Cell Carcinoma Cells of the Head and Neck", PLoS One, Jul. 2009, vol. 4, Issue 7.
Fielding et al., "A critical role of integrim-linked kinase, ch-TOG and TACC3 in centrosome clustering in cancer cells", Oncogene (2011) 30, 521-534. Publised online Sep. 13, 2010.
Yang et al., "Discovery of Potent KIFC1 Inhibitors Using a Method of Integrated High-Throughput Synthesis and Screening", J. Med. Chem., Nov. 19, 2014, 57, 9958-9970.
Li et al., "KIFC1 is a novel potential therapeutic target for breast cancer", Cancer Biology & Therapy 16:9, 1316-1322; Sep. 2015.
Zhang et al., "Discovery of a novel inhibitor of kinesin-like protein KIFC1", Biochem J. Apr. 15, 2016; 473(8): 1027-1035.
Akhmanova et al., "Control of microtubule organization and dynamics: two ends in the limelight", Molecular Cell Biology, vol. 16, Dec. 2015, 711-726.
Luconi et al., "Xenograft models for preclinical drug testing: Implications for adrenocortical cancer", Molecular and Cellular Endocrinology 351 (2012) 71-77 (Available online Oct. 26, 2011).
Hollingshead, "Antitumor Efficacy Testing in Rodents", Commentary, JNCI, vol. 100, Issue 21, Nov. 5, 2008.
Fiebig et al., "Clonogenic assay with established human tumour xenografts: correlation of in vitro to in vivo activity as a basis for anticancer drug discovery", European Journal of Cancer 40 (Jan. 26, 2004) 802-820.
Friedrich et al., "Spheroid-based drug screen: considerations and practical approach", Nature Protocols, vol. 4 No. 3 (Feb. 12, 2009) 309-324.
Froehlich et al., "Generation of Multicellular Breast Cancer Turmor Spheroids: Comparison of Different Protocols", J Mammary Gland Biol Neoplasia (Aug. 12, 2016) 21:89-98.
Zhang et al., "Recent advances in stimuli-responsive degradable block copolymer micelles: synthesis and controlled drug delivery applications", Chem. Commun., May 25, 2012, 48, 7542-7552.

* cited by examiner

A.

500nM C75 (8 hrs)

DMSO

D.

Metaphase Mitotic Spindle

C.

D.

B.

C.

E.

G.

B.

E.

F.

THIENOISOQUINOLINES AND THEIR DERIVATIVES FOR THE TREATMENT OF CANCER

CROSS REFERENCE TO RELATED APPLICATIONS

The present application is a 35 USC 371 national stage entry of PCT/CA2017/051473 filed on Dec. 6, 2017 and which claims priority from U.S. provisional application No. 62/430,387 filed on Dec. 6, 2016. These documents are hereby incorporated by reference in their entirety.

FIELD OF THE DISCLOSURE

This disclosure relates to thienoisoquinoline compounds and their derivatives, and more particularly to methods for selectively inhibiting growth in cancer using thienoisoquinoline compounds.

BACKGROUND OF THE DISCLOSURE

Cancer is now the leading cause of death in Canada. According to statistics from the Canadian Cancer Society, 1 out of 4 Canadians will die from the disease, and 2 out of 5 Canadians will develop cancers over their lifetime. Since the incidence of cancer is higher in people aged 50 and older, these numbers are expected to soar as the number of senior citizens in Canada increases. While the mortality rates from some cancers have decreased due to success in the clinic or through prevention (e.g. breast and prostate cancers), many aggressive, hard-to-treat cancers persist (e.g. lung, pancreatic and brain cancers). One of the main methods used to treat cancers is via the use of chemotherapies, which often has severe side-effects for patients, because most chemotherapeutic drugs also target healthy cells. Further, patients often develop resistance to drugs through various mechanisms. Combinatorial therapies are now being used to reduce side-effects and resistance, where two or more drugs are administered simultaneously or concurrently at lower doses. In addition, personalized medicine, where genetic profiling of individual tumours is used to tailor treatments more specifically to each patient, is another, more recent, treatment option. Thus, it is important to expand the repertoire of drugs to increase the number of cancers that can be treated effectively. However, current methods that are being used to search for novel anti-cancer compounds are often not successful[1]. They may be too restrictive, because they search for compounds with a specific molecular target that may not be optimal, or their drug-like qualities and ease of synthesis are not considered. For example, poor quality compounds may have solubility issues, they may aggregate and require high concentrations to be effective in vivo[2-6].

A subset of successful anti-cancer drugs used to treat a wide spectrum of cancers target mitosis, which is important for cell division[12,13]. One of the hallmarks shared by cancer cells is that they divide rapidly in an uncontrolled manner. The mitotic spindle is a structure that forms to align and segregate chromosomes, and to ensure that each daughter cell inherits the appropriate genetic content during division[14]. If the mitotic spindle fails to attach to the chromosomes properly, then the spindle assembly checkpoint (SAC) is not satisfied and the cell will arrest and undergo apoptosis[14-17]. Alternatively, chromosomes can be missegregated, leading to aneuploidy and mitotic catastrophe in subsequent divisions[18]. As healthy somatic cells enter mitosis, two centrosomes move apart and nucleate microtubules to form a bipolar spindle that then captures the chromosomes[19]. Many metastatic cancer cells have aberrant centrosomes, which are structurally or functionally defective[20-22]. Since centrosomes are the main sites for nucleating microtubules, cells with aberrant centrosomes often have defective mitotic spindles, such as multipolar spindles, with defective chromosome attachment[23]. Therefore, cancer cells rely on mechanisms to cluster fragmented or amplified centrosomes to form two poles[16,17,20-22]. The mechanisms that cancer cells use to cluster aberrant centrosomes are not well-understood, but are attractive to target via chemotherapies because their requirement is selective to cancer cells. In support of this, several publications have described searching for compounds that specifically target centrosome clustering[24-29]. However, the compounds described in these papers do not achieve high efficacy and are not ideal for clinical phase trials.

Thienoisoquinoline-phenyl sulfonamide compounds have been described in U.S. Pat. No. 7,696,221 (herein incorporated by reference in its entirety) for use as ER-NF kappa B receptors. Synthesis of thienoisoquinolines by a 5-step linear synthesis employing a palladium-catalyzed decarboxylative cross-coupling and functionalization sequence has been reported by Chen et al.[11], herein incorporate by reference in its entirety.

SUMMARY OF THE DISCLOSURE

According to an aspect, there is provided herein a method for selectively inhibiting growth in a cancer cell, comprising exposing the cancer cell to a compound of Formula I:

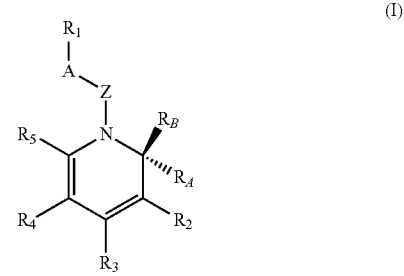

(I)

wherein

A is a $C_6$-$C_{12}$ aryl or a three- to seven-membered aromatic heterocycle;

Z is SO, $SO_2$, CO or $CH_2$;

$R_A$ and $R_B$ are each independently H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

$R_1$ is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

$R_2$ and $R_3$ are joined together to form a $C_6$-$C_{12}$ aryl or a three- to seven-membered aromatic heterocycle; and $R_4$ and $R_5$ are joined together to form a $C_6$-$C_{12}$ aryl or a three- to seven-membered aromatic heterocycle, $R_1$, $R_A$, $R_B$ the $C_6$-$C_{12}$ aryl and the three- to seven-membered aromatic heterocycle being each independently unsubstituted or substituted with at least one substituent chosen from $C_1$-$C_6$ alkyl, $C_1$-$C_6$ alkoxy, $C_6$-$C_{12}$ aryl, the three- to seven-membered aromatic heterocycle, $C_1$-$C_6$ hydroxyalkyl, $C_1$-$C_6$ alkythio, $C_1$-$C_6$ thioalkyl, $C_1$-$C_6$ sulfonylakyl, $C_1$-$C_6$ aminoalkyl, $C_1$-$C_6$ alkylamino, CN, $NO_2$, 4,5-dioxoyl, $NH_2$ $CF_3$, $CF_2H$, $CFH_2$, F, Cl, Br and I, OH, CHO, or a pharmaceutically acceptable salt, solvate or prodrug thereof.

According to another aspect, there is provided herein a method for disrupting centrosome integrity, preventing and/or reducing centrosome clustering, declustering centrosomes, regulating centrosome clustering and/or inducing microtubule depolymerization in a cancer cell, comprising exposing the cancer cell to a compound of Formula I.

According to yet another aspect, there is provided herein a method for selectively inhibiting growth in a cancer cell, comprising exposing the cancer cell to a combination of a compound of Formula I and an anti-cancer agent and/or an anti-mitotic agent.

According to another aspect, there is provided herein a method for inhibiting growth in a cancer cell, comprising exposing the cancer cell to a synergistic combination of a compound of Formula I and an anti-cancer agent and/or an anti-mitotic agent, wherein the combination more than additively inhibits growth of the cancer cell.

According to another aspect, there is provided herein a method for increasing selectivity of an anti-cancer agent and/or an anti-mitotic agent to a cancer cell, comprising exposing the cancer cell with a compound of Formula I and the anti-cancer agent and/or the anti-mitotic agent.

According to another aspect, there is provided herein a method of treating a cancer in a subject, comprising administering to the subject an effective amount of a compound of Formula I.

According to another aspect, there is provided herein a method of treating a cancer in a subject, comprising administering to the subject an effective amount of a combination of a compound of Formula I and an anti-cancer agent and/or an anti-mitotic agent.

According to a further aspect, there is provided herein a use of a compound of Formula I for selectively inhibiting growth in a cancer cell.

According to another aspect, there is provided herein a use of a compound of Formula I for disrupting centrosome integrity, preventing and/or reducing centrosome clustering, declustering centrosomes, regulating centrosome clustering and/or inducing microtubule depolymerization in a cancer cell.

According to yet another aspect, there is provided herein a use of a combination of a compound of Formula I and an anti-cancer agent and/or an anti-mitotic agent for selectively inhibiting growth in a cancer cell.

According to another aspect, there is provided herein a use of a compound of Formula I for the treatment of cancer in a subject.

According to another aspect, there is provided herein a use of a combination of a Formula I and an anti-cancer agent and/or an anti-mitotic agent for the treatment of cancer in a subject.

According to another aspect, there is provided herein a use of a compound of Formula I in combination with an anti-cancer agent and/or an anti-mitotic agent for increasing selectivity of the anti-cancer agent and/or the anti-mitotic agent to a cancer cell.

According to a further aspect, there is provided herein a compound of Formula I:

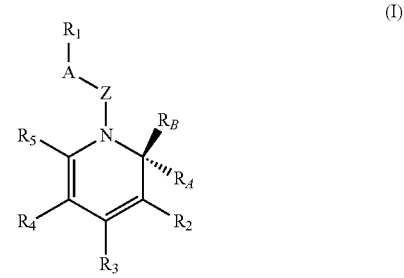

wherein

A is a $C_6$-$C_{12}$ aryl or a three- to seven-membered aromatic heterocycle;

Z is SO, $SO_2$, CO or $CH_2$;

$R_A$ and $R_B$ are each independently H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

$R_1$ is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

$R_2$ and $R_3$ are joined together to form a $C_6$-$C_{12}$ aryl or a three- to seven-membered aromatic heterocycle; and $R_4$ and $R_5$ are joined together to form a $C_6$-$C_{12}$ aryl or a three- to seven-membered aromatic heterocycle, $R_1$, $R_A$, $R_B$ said $C_6$-$C_{12}$ aryl and said three- to seven-membered aromatic heterocycle being each independently unsubstituted or substituted with at least one substituent chosen from $C_1$-$C_6$ alkyl, $C_1$-$C_6$ alkoxy, $C_6$-$C_{12}$ aryl, three- to seven-membered aromatic heterocycle, $C_1$-$C_6$ hydroxyalkyl, $C_1$-$C_6$ alkythio, $C_1$-$C_6$ thioalkyl, $C_1$-$C_6$ sulfonylakyl, $C_1$-$C_6$ aminoalkyl, $C_1$-$C_6$ alkylamino, CN, $NO_2$, 4,5-dioxoyl, $NH_2$ $CF_3$, $CF_2H$, $CFH_2$, F, Cl, Br and I, OH, CHO, or a pharmaceutically acceptable salt, solvate or prodrug thereof.

According to a further aspect, there is provided herein a compound of Formula IA:

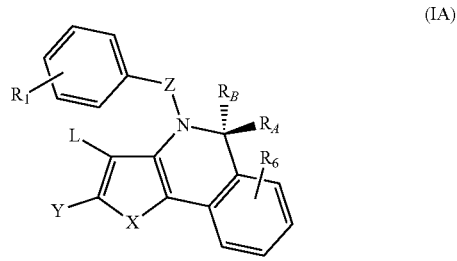

L is H, $C_1$-$C_3$ alkyl, $C_1$-$C_3$ alkoxy, $C_1$-$C_3$ thioalkyl, $C_1$-$C_3$ haloalkyl, ON, $CF_3$, $CF_2H$, $CFH_2$, F, Cl, Br or I;

X is S, O, $NR_7$ or NH;

Y is F, Cl, Br, I, H, $CH_3$, $CF_3$, $CHF_2$, $CF_2H$ or CN;

Z is $SO_2$, CO or $CH_2$;

$R_A$ and $R_B$ are each independently H, Me, Et, $CF_3$, $CF_2H$, $CFH_2$, F or Cl;

$R_1$ is $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br or I;

$R_6$ is $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br or I; and $R_7$ is $C_1$-$C_6$ alkyl, $C_1$-$C_6$ haloalkyl, $C_1$-$C_6$ sulfonylakyl, $C_1$-$C_6$ alkylamino, $CF_3$, $CF_2H$, $CFH_2$, a $C_6$-$C_{12}$ aryl or a three- to seven-membered aromatic heterocycle, L, $R_A$, $R_B$, $R_1$, $R_6$, the $C_6$-$C_{12}$ aryl and the three- to seven-membered aromatic heterocycle being each independently unsubstituted or substituted with at least one substituent chosen from $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, F, Cl, Br and I, or a pharmaceutically acceptable salt, solvate or prodrug thereof.

According to a further aspect, there is provided herein a compound chosen from:

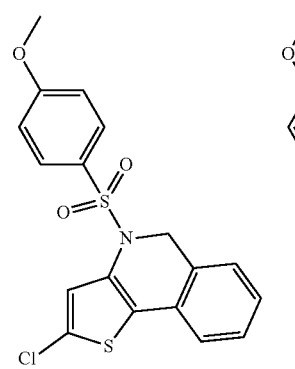
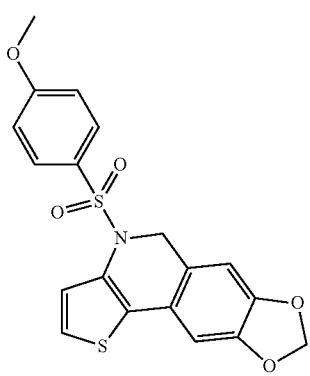
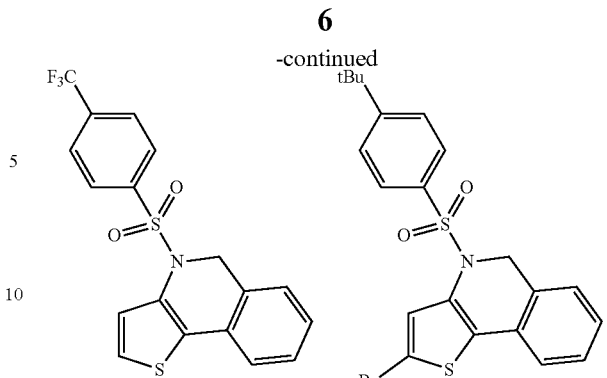
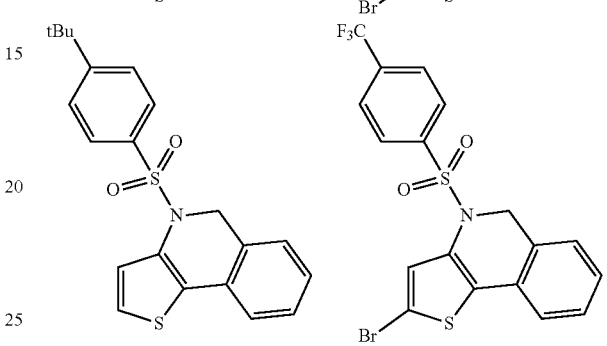
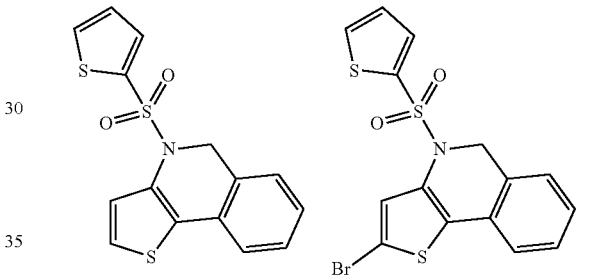
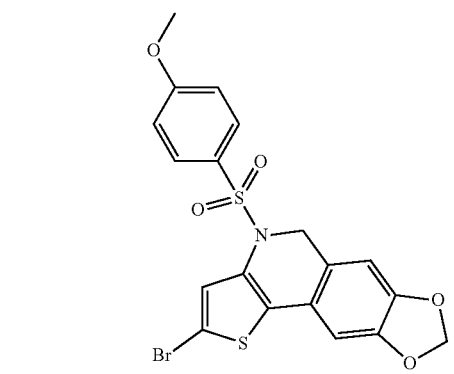
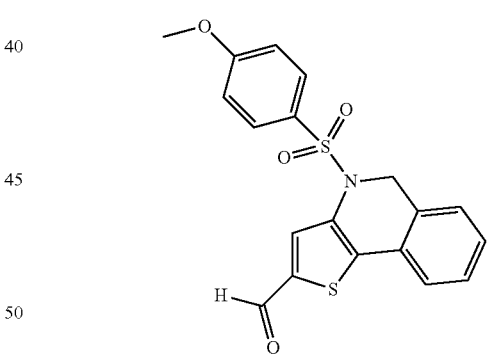
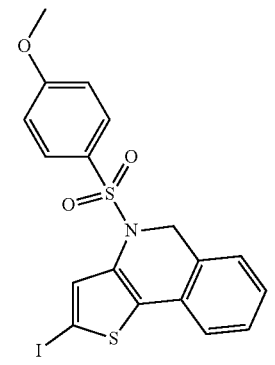
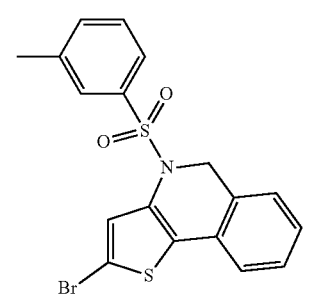
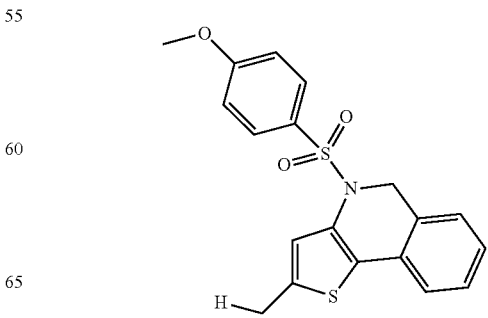

-continued
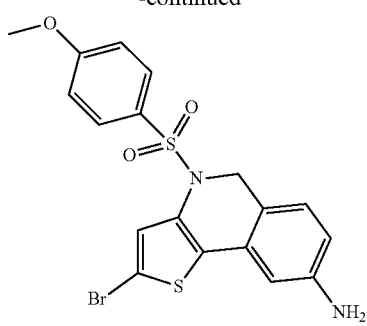
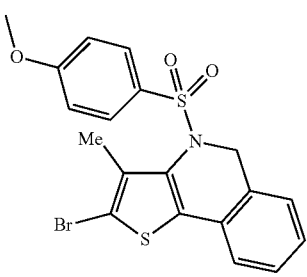
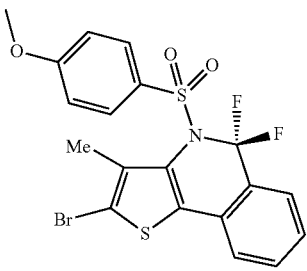
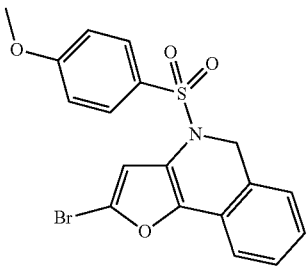
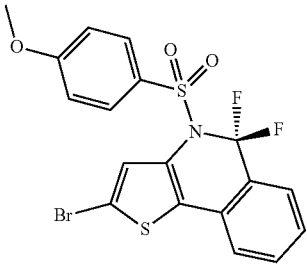
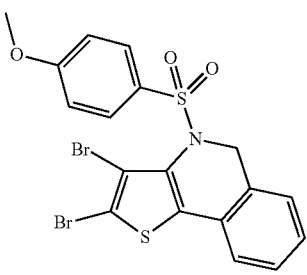
-continued
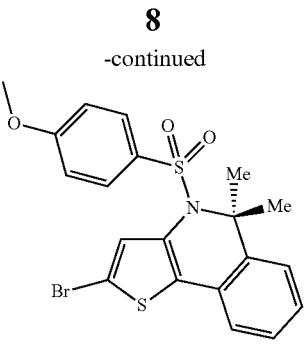
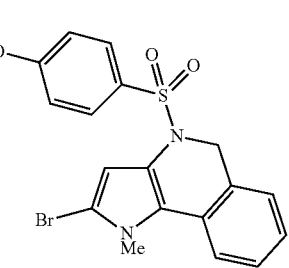
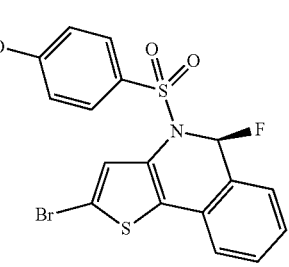
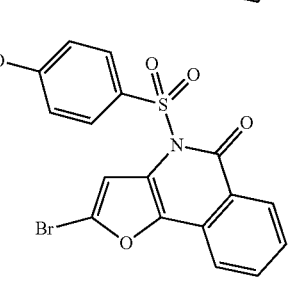
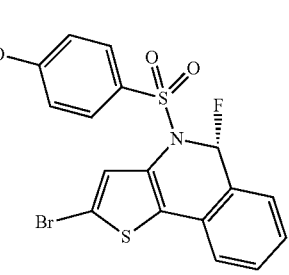
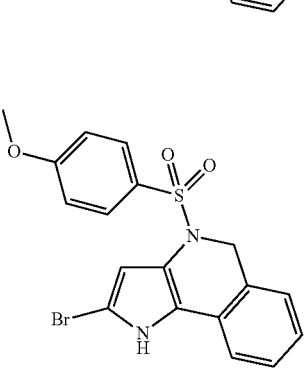

-continued
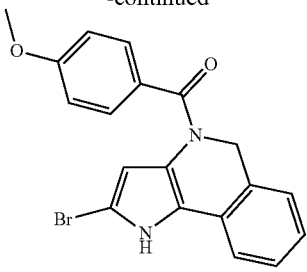
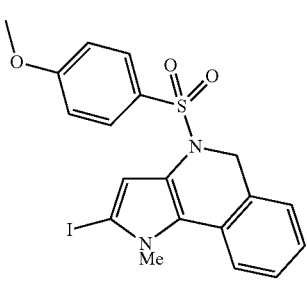
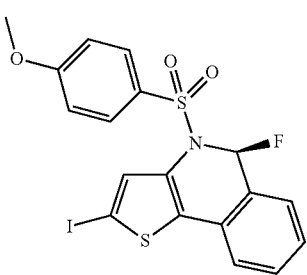
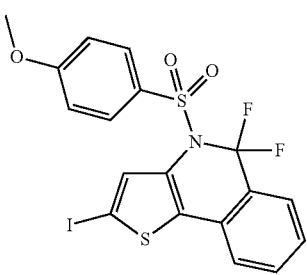
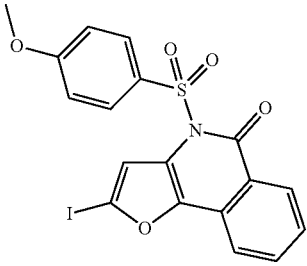
-continued
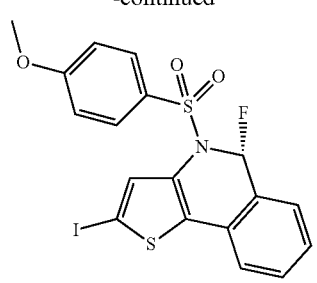
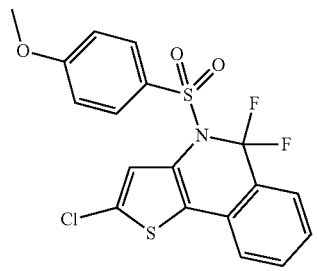
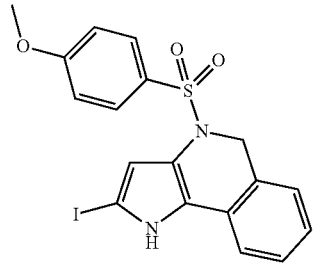
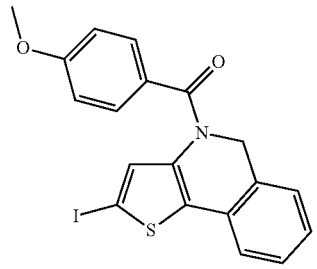
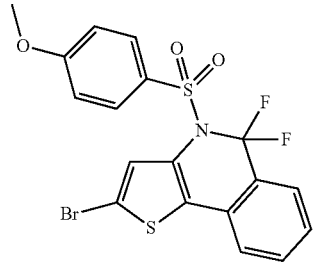
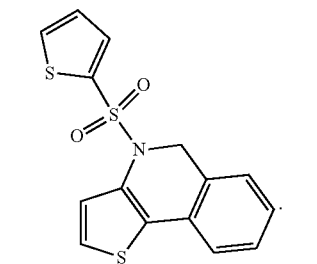

According to a further aspect, there is provided herein a compound of Formula IB:

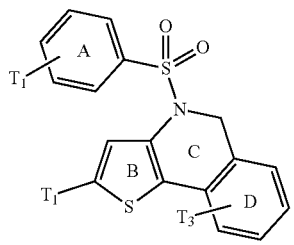

(IB)

TABLE 1

|  | T₁ | T₂ | T₃ |
|---|---|---|---|
| C39 | 3-Me | H | H |
| C71 | 4-Me | Ph | H |
| C74 | 4-Me | Br | H |
| C75 | 4-OMe | Br | H |
| C90 | 4-OMe | H | H |
| C91 | 4-Me | H | H |
| C93 | 3-Me | Br | H |
| C108 | 4-CF₃ | H | H |
| C200 | 4-CF₃ | Br | H |
| C201 | 4-tBu | Br | H |
| C207 | 4-OMe | I | H |
| C208 | 4-OMe | Cl | H |

According to a further aspect, there is provided herein a compound Formula IC:

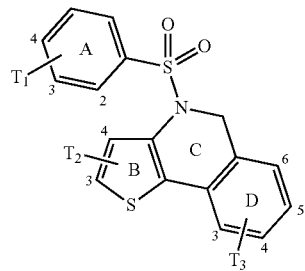

(IC)

TABLE 2

| T₁ | T₂ | T₃ |
|---|---|---|
| 4-Me | H | H |
| 3-Me | H | H |
| 2-Me | H | H |
| 4-OMe | H | H |
| 4-F | H | H |
| 4-Me | 3-Br | H |
| 4-OMe | 3-Br | H |
| 4-Me | 3-Benzyl | H |
| 4-Me | 3-Toluenyl | H |
| 4-Me | 3-Naphthalenyl | H |
| 4-Me | 3-(4-Methoxylphenyl) | H |
| 4-Me | 3-(3-Methoxylphenyl) | H |
| 4-Me | 3-(4-ethyl benzoate) | H |
| 4-Me | 3-(3-ehtyl benzoate) | H |
| 4-Me | 3-(4-fluorophenyl) | H |
| 4-Me | 3-(4-benzonitrile) | H |
| 4-Me | 3-(4-trifluoromethylphenyl) | H |
| 4-Me | 3-pyridinyl | H |

TABLE 2-continued

| T₁ | T₂ | T₃ |
|---|---|---|
| 4-OMe | 3-Cl | H |
| 4-OMe | 3-I | H |
| 3-Me | 3-Br | H |
| 4-CF₃ | H | H |
| 4-CF₃ | 3-Br | H |
| 4-tBu | 3-Br | H |
| 4-OMe | 3-CHO | H |
| 4-OMe | 3-CH₂OH | H |
| 4-OMe | 3-CH₂OCH₃ | H |
| 4-OMe | 3-COCH₃ | H |
| 4-OMe | 3-Br | 4,5-dioxoyl |
| 4-OMe | 3-Br | 3-NO₂ |
| 4-OMe | 3-Br, 4-Methyl | H |
| 4-OMe | 3-Br | 3-NH₂, 6-Br |
| Thiophene ring | 3-Br | H |
| 4-OMe | 3,4-di-Me | H |
| 4-OMe | 3-CN, 4-Me | H |
| 4-OMe | 3-Br | 3-Br |
| 4-OMe | 3-Br | 3-NH₂ |
| 4-OMe | 3-H | 6-NO₂ |
| 4-OMe | 3-H | 4-NH₂ |
| 4-OMe | 3-Br | 4-NH₂ |
| 4-OMe | 3-Br | 6-NH₂ |
| 4-OMe | 3-OH | 6-NH₂ |
| 4-OMe | 3-Br | 4-NO₂ |
| 4-OMe | 3-Br | 6-NO₂ |
| 4-OMe | 3-Br | 3-OH |
| 4-OMe | 3-H | 4-NO₂ |
| 4-OMe | 3-NO₂ | H |
| 4-OMe | 3-Me | H |
| 4-OMe | 3-NH₂, 4-Me | H |
| 4-OMe | 3-CHO, 4-Me | H |
| 4-OMe | 3-OH, 4-Me | H |
| 4-OMe | 3-OH | H |
| 4-OMe | 3-NH₂ | H |
| 4-OMe | 3-CF₃ | H |
| 4-OMe | 3-F | H |
| 4-OMe | 3-OMe | H |
| 4-OMe | 3-CN | H |
| 4-OEt | 3-Br | H |
| 4-OiPr | 3-Br | H |
| 4-NMe₂ | 3-Br | H |
| 4-OMe | 3-Br, 4-Br | H |

BRIEF DESCRIPTION OF THE FIGURES

Further features and advantages of the disclosure will become more readily apparent from the following description of specific embodiments as illustrated by way of examples in the appended figures wherein:

FIG. 1A) shows bright-field images of fields of view of HeLa cells treated with DMSO or 500 nM C75 for 8 hours. There were more rounded mitotic cells after C75 treatment in comparison to the control. FIG. 1B) is a line graph showing the percentage of HeLa and HFF1 cells in mitosis after treatment with various concentrations of C75 for 8 hours. The bars indicate standard deviation. FIG. 1C) is a series of images showing cells that were fixed and co-stained for tubulin (microtubules) and DAPI (DNA). Treatment of HeLa cells with 300 nM C75 caused the mitotic spindles to be disorganized, while they were not affected in HFF1 cells. Treatment of 750 nM C75 caused complete fragmentation of the mitotic spindles in HeLa cells, while they were disorganized in HFF1 cells. The scale bar for the cells is 10 μm.

FIG. 2A) is a line graph showing the percentage of HCT116 (p53−/−) cells, A549 cells, HeLa cells and H1299 cells in mitosis after treatment with various concentrations of C75 for one population doubling time. All of the cell lines show an increase in the proportion of mitotic cells after treatment with 200 nM C75. The bars indicate standard deviation. FIG. 2B) is a series of images showing HFF1, H1299, MCF-10A and MCF-7 cells that were fixed and co-stained for tubulin (microtubules) and DAPI (DNA) after 6-8 hours of treatment with 300 nM of C87 (inactive derivative) or C75 as indicated. While the mitotic spindles were not dramatically altered by C75 in HFF1 cells, they were monopolar (as shown) or fragmented in the other cell types. FIG. 2C) are images showing fixed HeLa, BT-549, A549 and HCT116 (p53−/−) cells that were fixed and co-stained for tubulin (microtubules) and DAPI (DNA) after 6-8 hours of treatment treated with 300 nM of C87 (less active derivative) or C75 as indicated. The mitotic spindles were more strongly fragmented after C75 treatment in these cells vs. the cells in FIG. 2B). FIG. 2E) shows images of fixed HeLa cells treated as shown in 2D), co-stained for tubulin (microtubules) and DAPI (DNA). While mitotic spindles recovered bipolarity after removing nocodazole, they remained multipolar after removing C75. FIG. 2F) is a series of time-lapse images of a live HeLa cell expressing GFP:tubulin after treatment with C75 as shown in 2D) and 2E). The scale bar for all cells is 10 µm.

FIG. 3A) is a line graph showing the percentage of mitotic HeLa or HFF1 cells treated with a range of paclitaxel (Taxol™; tubulin-targeting drug) concentrations+/−C75 as indicated. The bars indicate standard deviation. FIG. 3B) is a series of bar graphs showing the proportion of HCT116 cells that have monopolar spindles, bipolar spindles with aligned chromosomes, bipolar spindles with misaligned chromosomes and multipolar/fragmented spindles after treatments as shown. Treatments include DMSO (control), varying concentrations of paclitaxel and/or varying concentrations of C75 after 7 hours. While treatment of HCT116 cells with 2.5 nM paclitaxel caused a threshold of mitotic spindle phenotypes, adding increasing concentrations of C75 in combination with 2.5 nM paclitaxel caused the phenotypes to progressively worsen. FIG. 3C) is bar graph showing the average distance between centrosome fragments in HCT116 cells after treatments as shown. While centrosome fragments moved closer together with increased concentrations of paclitaxel, they moved further apart with increased concentrations of C75. FIG. 3D) is a series of images of fixed HCT116 cells stained for tubulin (microtubules) and DAPI (DNA), demonstrating the differences in the distance between spindle fragments. FIG. 3E) is a line graph showing the percentage of mitotic HeLa or HFF1 cells treated with a range of nocodazole concentrations+/−C75 as indicated. The bars indicate standard deviation. FIG. 3F) is a series of images showing fixed HeLa cells after treatment with C75+/− nocodazole co-stained for tubulin, γ-tubulin and DNA (DAPI). A dotted line shows the outline of the cells. Adding nocodazole to cells treated with 300 nM C75 caused mitotic spindle phenotypes to worsen and appear more similar to those after treatment with 600 nM C75. The scale bar for all cells is 10 µm. FIG. 3G) is a bar graph showing the percentage of phenotypes observed for metaphase HeLa cells treated with nocodazole or C75, or both for 20 minutes (n>15 per treatment).

DETAILED DESCRIPTION OF THE DISCLOSURE

Figure 1:
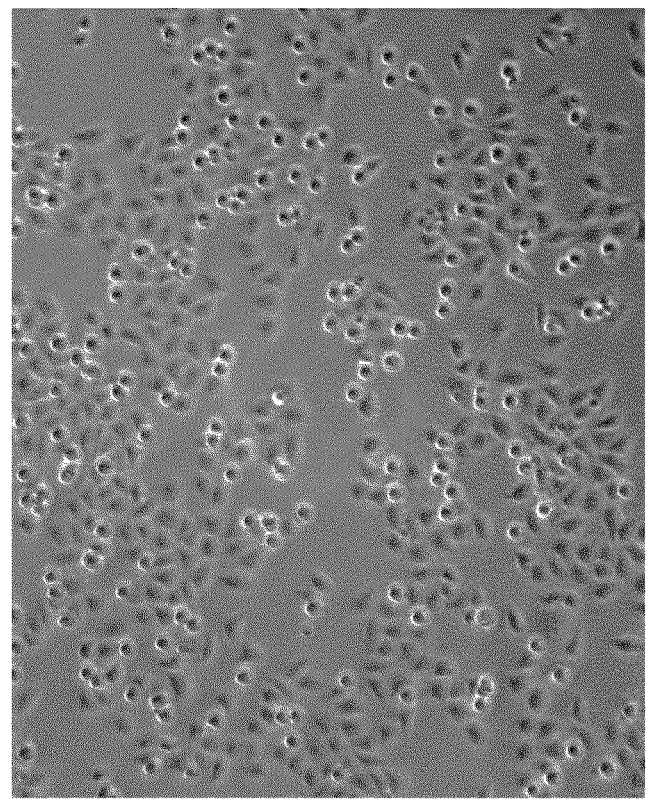
FIGS. 1A, 1B and 1C show that Compound 75 (C75) selectively causes mitotic arrest in cancer cells and disrupts spindle morphology.
FIG. 1D) is a cartoon schematic showing the key features of a metaphase cell.
Figure 1:
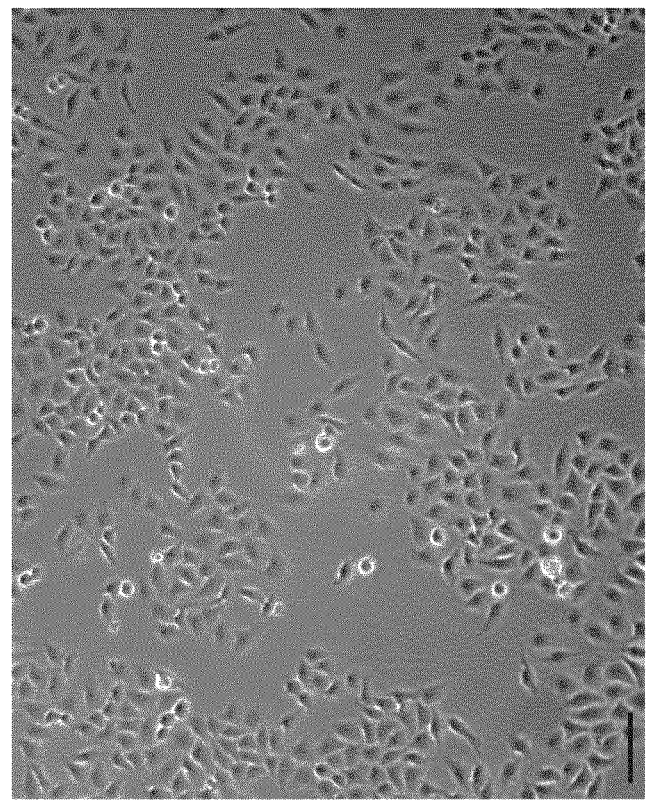
Figure 1:
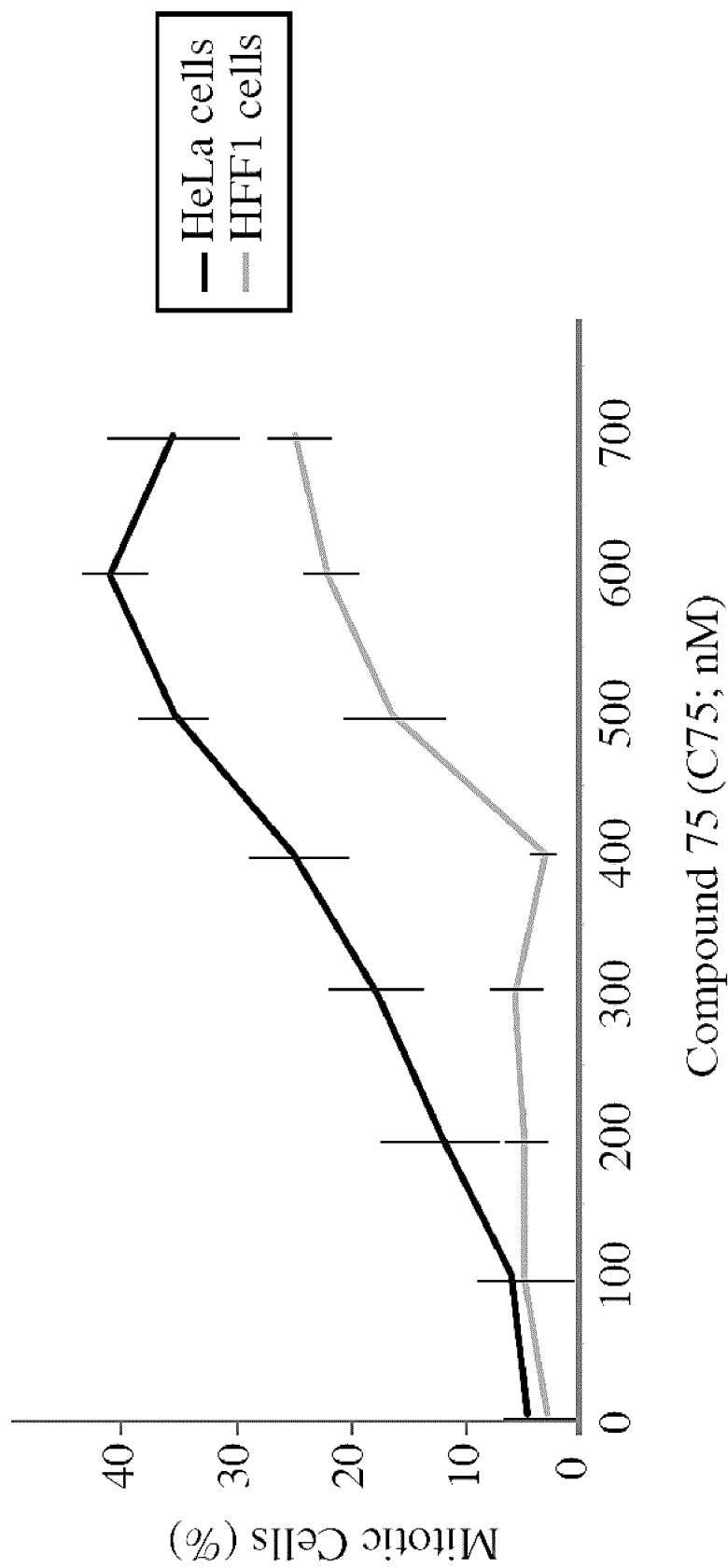
Figure 1:
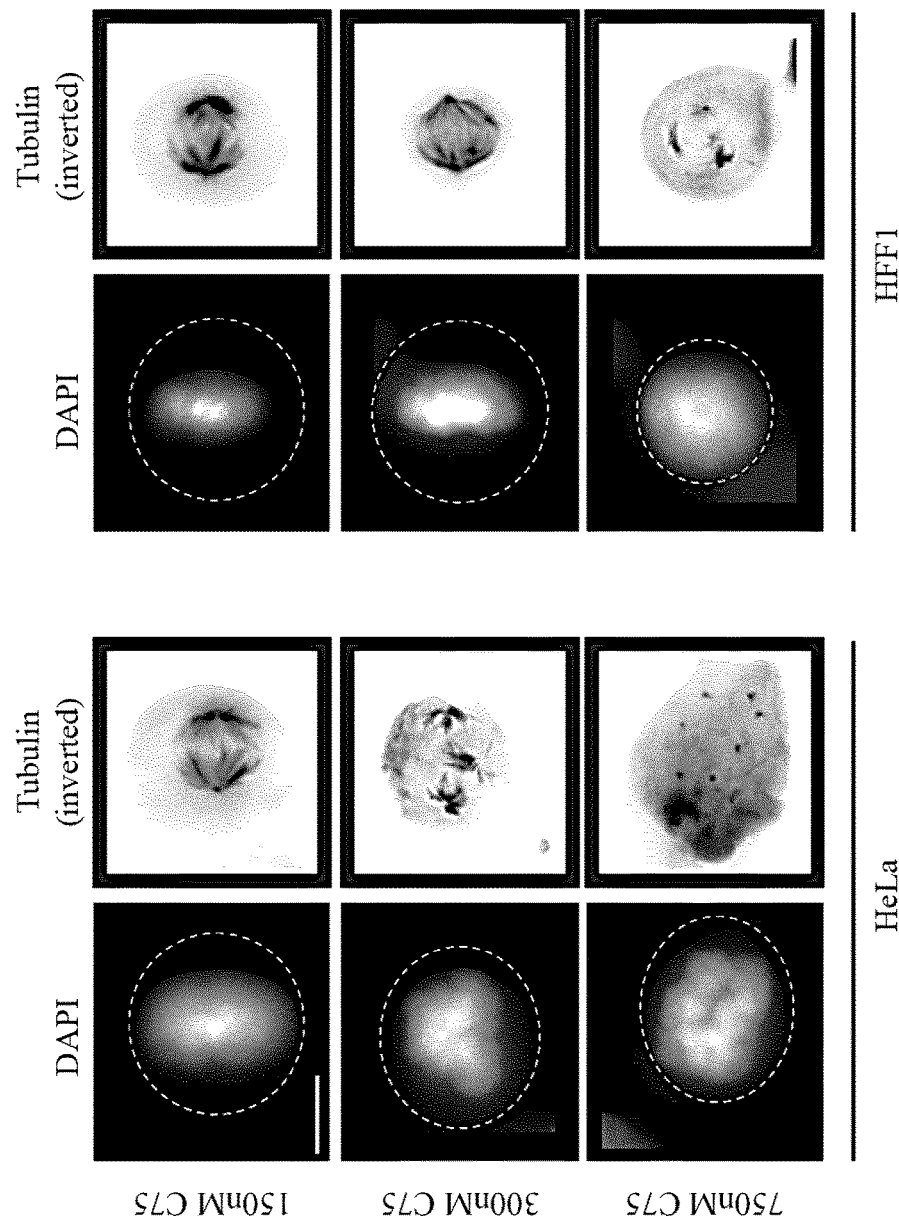
Figure 1:
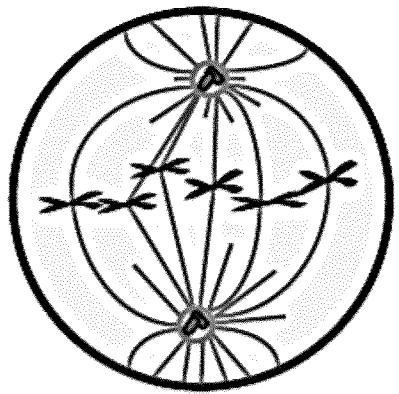
Figure 1:
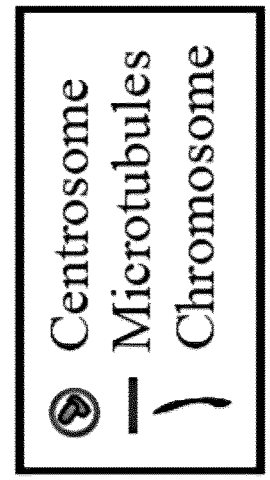

Accordingly, a class of anti-cancer compounds with potential for clinical use has been identified. By synthesizing compounds with a quinoline scaffold that already has been proven to have successful drug-like properties[7-11], it has been made possible to overcome limitations related to quality. These compounds appear to have a unique mechanism of action in comparison to known anti-cancer drugs, by targeting a process that occurs uniquely in cancer cells, making the compounds selective for cancer cells. In addition, these compounds enhance the selectivity of other anti-cancer drugs, making them suitable for use in combinatorial therapies.

I. Definitions

The expression "compound(s) of the present disclosure" as used in the present document refers to compounds of formulae I and IA presented in the present disclosure, isomers thereof, such as stereoisomers (for example, enantiomers, diastereoisomers, including racemic mixtures) or tautomers, or to pharmaceutically acceptable salts, solvates, hydrates and/or prodrugs of these compounds, isomers of these latter compounds, or racemic mixtures of these latter compounds. The expression "compound(s) of the present disclosure" also refers to mixtures of the various compounds or variants mentioned in the present paragraph.

It is to be understood that the present disclosure includes isomers, racemic mixtures, pharmaceutically acceptable salts, solvates, hydrates and prodrugs of compounds described therein and mixtures comprising two or more of such compounds.

The compounds of the disclosure may have at least one asymmetric centre. Where the compounds disclosed herein possess more than one asymmetric centre, they may exist as diastereomers. It is to be understood that all such isomers and mixtures thereof in any proportion are encompassed within the scope of the present disclosure. It is to be understood that while the stereochemistry of the compounds of the present disclosure may be as provided for in any given compound listed herein, such compounds of the disclosure may also contain certain amounts (for example less than 30%, less than 20%, less than 10%, or less than 5%) of compounds of the present disclosure having alternate stereochemistry.

The term "alkyl" as used herein means straight and/or branched chain, saturated alkyl groups containing from one to n carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, wherein n is the maximum number of carbon atoms in the group.

The term "aryl" as used herein refers to a cyclic or polycyclic aromatic ring. For example, the aryl group can be phenyl or napthyl.

The expression "aromatic heterocycle" as used herein refers to an aromatic cyclic or fused polycyclic ring system having at least one heteroatom selected from the group consisting of N, O, S and P. Non-limitative examples include heteroaryl groups are furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The expression "non-aromatic heterocycle" includes non-aromatic rings or ring systems that contain at least one ring having at least having at least one heteroatom selected from the group consisting of N, O, S and P. This term includes, in a non-limitative manner all of the fully saturated and partially unsaturated derivatives of the above mentioned aromatic heterocycles groups. Examples of non-aromatic heterocycle groups include, in a non-limitative manner, pyrrolidinyl, tetrahydrofuranyl, morpholinyl, thiomorpholinyl, piperidinyl, piperazinyl, thiazolidinyl, isothiazolidinyl, and imidazolidinyl.

The term "suitable", as in for example, "suitable counter anion" or "suitable reaction conditions" means that the selection of the particular group or conditions would depend on the specific synthetic manipulation to be performed and the identity of the molecule but the selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where $CO_2H$ is a functional group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

Compounds of the present disclosure include prodrugs. In general, such prodrugs will be functional derivatives of these compounds which are readily convertible in vivo into the compound from which it is notionally derived. Prodrugs of the compounds of the present disclosure may be conventional esters formed with available hydroxy, or amino group. For example, an available OH or nitrogen in a compound of the present disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the present disclosure are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The term "cancer" as used herein means a primary or a secondary cancer and includes a non-metastatic cancer and/or a metastatic cancer. Reference to cancer includes reference to cancer cells. For example, the cancer is cervical cancer, breast cancer, ovarian cancer, brain cancer, melanoma, colorectal cancer, glioblastoma, liver cancer, lung cancer, prostate cancer, head cancer, gastric cancer, kidney cancer, endometrial cancer, testis cancer, urothelial cancer, acute lymphoblastic leukemia, acute myeloid leukemia, Hodgkin lymphoma, neuroblastoma, non-Hodgkin lymphoma, soft tissue cancer, bone sarcoma, thyroid cancer, transitional cell bladder cancer, Wilm's tumour, glioma, pancreatic cancer or spleen cancer. For example, the cancer includes any cancer causing centrosome aberrations in the cancer cell.

The term "cancer cell" as used herein refers to in vitro cancer cells but also to in vivo cancer cells, e.g. cancer cells present in a subject such as a mammal or a human. For example, in vitro cancer cells may include human breast cancer cells (e.g. BT-549 and MCF-7 cells), mouse neuroblastoma cells (e.g. N1E-115 cells), human lung cancer (e.g. A549 cells), human non-small cell lung cancer cells (e.g. H1299 cells), colorectal cancer cells (e.g. HCT116 cells) or human cervical cancer cells (e.g. HeLa).

The term "anti-cancer agent" as used herein means an agent capable of producing a therapeutic effect by inhibiting, suppressing or reducing a cancer (e.g., as determined by clinical symptoms or the amount of cancerous cells) in a subject as compared to a control. Examples of anti-cancer agents include for example non-tubulin-targeting drugs such as doxorubicin, and tubulin-targeting drugs such as taxanes (e.g. paclitaxel), vinca alkaloids (e.g. vinblastine).

The term "anti-mitotic agent" as used herein means an agent that can be used for blocking cancer cell proliferation. For example, the anti-mitotic agent can be an agent that causes microtubule depolymerization such as for example nocodazole or colchicine.

The term "mixture" as used herein, means a composition comprising two or more compounds. In an embodiment a mixture is a mixture of two or more distinct compounds, for example a mixture comprising a compound herein disclosed and an anti-cancer agent such as a taxane for example. In a further embodiment, when a compound is referred to as a "mixture", it may comprise two or more "forms" of the compounds, such as, salts, solvates, prodrugs or, where applicable, stereoisomers of the compound in any ratio. A person of skill in the art would understand that a compound in a mixture can also exist as a mixture of forms. For example, a compound may exist as a hydrate of a salt or as a hydrate of a salt of a prodrug of the compound. All forms of the compounds disclosed herein are within the scope of the present application.

The term "subject" as used herein includes all members of the animal kingdom including a mammal. In an embodiment, the mammal is a mouse. In another embodiment, the mammal is a human.

The terms "suitable" and "appropriate" refer to the selection of particular groups or conditions that would depend for example on the specific synthetic manipulation to be performed and the identity of the compound, however the selection remains well within the skill of a person trained in the art. All method steps described herein are to be conducted under conditions suitable to provide the product described. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression an "effective amount" of a compound or composition of the present disclosure is a quantity sufficient to, when administered to the subject, including a mammal, for example a human, effect beneficial or desired results, including clinical results, and, as such, an "effective amount" depends upon the context in which it is being applied. For example, in the context of treating cancer, for example, it is an amount of the compound or composition, alone or in combination with an anti-cancer agent and/or an anti-mitotic agent, sufficient to achieve treatment of the cancer as compared to a response in the absence of administration of the compound or composition, alone or in combination with an anti-cancer agent and/or an anti-mitotic agent. The amount of a given compound or composition of the present disclosure that corresponds to an effective amount will vary depending upon various factors, such as for example the given drug or compound, the pharmaceutical formulation, the route of administration, the type of disease or disorder, the identity of the subject or host being treated, and the like, but can nevertheless be routinely determined by one skilled in the art. Also, as used herein, an "effective amount" of a compound of the present disclosure is an amount which inhibits, suppresses or reduces a cancer (e.g., as determined by clinical symptoms or the amount of cancerous cells) in a subject as compared to a control. As further used herein, the "effective amount" is an amount that is sufficient to induce mitotic arrest, disrupt centrosome integrity, prevent and/or reduce centrosome clustering, decluster centrosomes and/or induce microtubule depolymerization in a cancer cell.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment. "Palliating" a disease or disorder, means that the extent and/or undesirable clinical manifestations of a disorder or a disease state are lessened and/or time course of the progression is slowed or lengthened, as compared to not treating the disorder.

The term "administered" as used herein means administration of a therapeutically effective dose of a composition of the application to a cell either in cell culture or in a patient.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

In compositions comprising an "additional" or "second" component, the second component as used herein is chemically different from the other components or first component. A "third" component is different from the other, first, and second components, and further enumerated or "additional" components are similarly different.

The definitions and embodiments described in particular sections are intended to be applicable to other embodiments herein described for which they are suitable as would be understood by a person skilled in the art.

II. Methods and Compounds

It is demonstrated herein that the presently disclosed compounds are useful for inducing death in several cancer cells and further are useful when combined with other drugs such as anti-mitotic agents or anti-cancer agents.

Accordingly, there is provided in a first aspect a method for selectively inhibiting growth in a cancer cell, comprising exposing the cancer cell to a compound of Formula I:

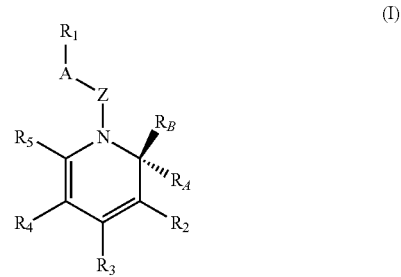

wherein
A is a $C_6$-$C_{12}$ aryl or a three- to seven-membered aromatic heterocycle;
Z is SO, $SO_2$, CO or $CH_2$;
$R_A$ and $R_B$ are each independently H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;
$R_1$ is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;
$R_2$ and $R_3$ are joined together to form a $C_6$-$C_{12}$ aryl or a three- to seven-membered aromatic heterocycle; and
$R_4$ and $R_5$ are joined together to form a $C_6$-$C_{12}$ aryl or a three- to seven-membered aromatic heterocycle,
$R_1$, $R_A$, $R_B$ the $C_6$-$C_{12}$ aryl and the three- to seven-membered aromatic heterocycle being each independently unsubstituted or substituted with at least one substituent chosen from $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br and I, or a pharmaceutically acceptable salt, solvate or prodrug thereof.

For example, the inhibiting growth comprises inducing mitotic arrest in the cancer cell.

According to another aspect, there is provided herein a method for disrupting centrosome integrity, preventing and/or reducing centrosome clustering, declustering centrosomes, regulating centrosome clustering and/or inducing microtubule depolymerization in a cancer cell, comprising exposing the cancer cell to a compound of Formula I.

According to yet another aspect, there is provided herein a method for selectively inhibiting growth in a cancer cell, comprising exposing the cancer cell to a combination of a compound of Formula I and an anti-cancer agent and/or an anti-mitotic agent.

According to another aspect, there is provided herein a method for inhibiting growth in a cancer cell, comprising exposing the cancer cell to a synergistic combination of a compound of Formula I and an anti-cancer agent and/or an anti-mitotic agent, wherein the combination more than additively inhibits growth of the cancer cell.

According to another aspect, there is provided herein a method for increasing selectivity of an anti-cancer agent and/or an anti-mitotic agent to a cancer cell, comprising exposing the cancer cell with a compound of Formula I and the anti-cancer agent and/or the anti-mitotic agent.

For example, the cancer cells are contacted with a thienoisoquinoline compound herein disclosed at a concentration in the nanomolar range. For example, the method comprises exposing the cancer cell to the compound having a concentration of about 1 nM, about 5 nM, about 100 nM, about 150 nM, about 200 nM, about 250 nM, about 300 nM, about 350 nM, about 400 nM, about 450 nM, about 500 nM, about 550 nM, about 600 nM, about 1000 nM, about 5000 nM or about 10000 nM.

For example, the method comprises exposing the cancer cell to the compound for at least 1 minute, 2 minutes, 3 minutes, 4 minutes, 5 minutes, 10 minutes, 15 minutes, 20 minutes, 30 minutes, at least 45 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 24 hours, at least 30 hours, at least 36 hours, at least 42 hours, at least 48 hours, at least 60 hours, at least 72 hours or at least 80 hours. For example, the cancer cells can also be contacted with a thienoisoquinoline compound herein disclosed for a population doubling time. The term "population doubling time" is to be understood as the period of time required to double the cell population.

For example, the cancer cell is a cancer cell with aberrant centrosomes.

For example, the cancer cell is a breast cancer cell, a cervical cancer cell, a lung cancer cell, a non-small cell lung cancer cell, a pancreatic cancer cell, a colorectal cancer cell, a colon cancer cell, a neuroblastoma cancer cell or an ovarian cancer cell.

For example, the cancer cell is a mammal cancer cell.

For example, the mammal cancer cell is a human cancer cell.

For example, the method is carried out in vitro.

For example, the method is carried out in vivo.

For example, the cancer cell is present in a subject.

For example, the subject is a mammal.

For example, the mammal is a human.

According to another aspect, there is provided herein a method of treating a cancer in a subject, comprising administering to the subject an effective amount of a compound of Formula I.

According to another aspect, there is provided herein a method of treating a cancer in a subject, comprising administering to the subject an effective amount of a combination of a compound of Formula I and an anti-cancer agent and/or an anti-mitotic agent.

For example, the cancer is a cancer causing aberrant centrosomes.

For example, the cancer is breast cancer, cervical cancer, lung cancer, non-small cell lung cancer, pancreatic cancer, colorectal cancer, colon cancer, neuroblastoma cancer or ovarian cancer.

For example, the subject is a mammal.

For example, the mammal is a human.

For example, the compound for Formula I and anti-cancer agent and/or anti-mitotic agent are administered sequentially or concomitantly.

For example, the anti-cancer agent is a taxane, a *vinca* alkaloid or a colchicine-site binder.

For example, the anti-cancer agent is a non-mitotic anti-cancer agent.

For example, the anti-mitotic agent is nocodazole.

For example, the cancer cells are further contacted with nocodazole at a concentration of about 5 nM, about 10 nM, about 15 nM, about 20 nM, about 25 nM, about 30 nM, about 33 nM, about 35 nM, about 40 nM, about 45 nM, about 50 nM, about 55 nM, about 60 nM, about 66 nM, about 70 nM, about 75 nM, about 100 nM, about 125 nM or about 135 nM.

For example, the taxane is paclitaxel, cabazitaxel, or docetaxel.

For example, the cancer cells are further contacted with a taxane at a concentration of about 1 nM, about 2 nM, about 3 nM, about 4 nM, about 5 nM, about 6 nM, about 7 nM, about 8 nM, about 9 nM, about 10 nM, about 11 nM, about 12 nM, about 13 nM, about 14 nM, about 15 nM, about 16 nM, about 17 nM, about 18 nM, about 19 nM, about 20 nM, about 25 nM, about 30 nM, about 35 nM, about 40 nM, about 45 nM, about 50 nM, about 60 nM, about 70 nM, about 80 nM, about 90 nM or about 100 nM.

For example, the *vinca* alkaloid is vinblastine, vincristine, vindesine, and vinorelbine.

For example, the colchicine-site binder is colchicine, a combrestatin or podophyllotoxin.

For example, the non-mitotic anti-cancer agent is doxorubicin, an anthracycline, an alkylating drug or an antimetabolite.

For example, the compound of Formula I is a compound of Formula IA:

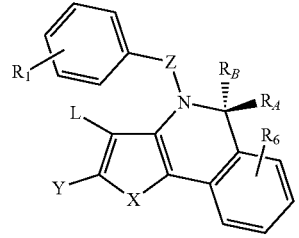

(IA)

L is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

X is S, O, NH, CH=CH, CH=N, N=CH or $NR_7$;

Y is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

Z is SO, $SO_2$, CO or $CH_2$;

$R_A$ and $R_B$ are each independently H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, $CF_3$, $CF_2H$, $CFH_2$, F, Cl, Br, I, a $C_6$-$C_{12}$ aryl or a three- to seven-membered aromatic heterocycle;

$R_1$ is H, $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, $C_1$-$C_6$ sulfonylakyl, $C_1$-$C_6$ aminoalkyl, $C_1$-$C_6$ alkylamino, CN, CF$_3$, CF$_2$H, CFH$_2$, F, Cl, Br, I, a C$_6$-C$_{12}$ aryl or a three- to seven-membered aromatic heterocycle;

R$_6$ is H, C$_1$-C$_6$ alkyl, C$_1$-C$_6$ alkoxy, C$_1$-C$_6$ hydroxyalkyl, C$_1$-C$_6$ alkythio, C$_1$-C$_6$ thioalkyl, C$_1$-C$_6$ haloalkyl, F, C$_1$-C$_6$ sulfonylakyl, C$_1$-C$_6$ aminoalkyl, C$_1$-C$_6$ alkylamino, CN, CF$_3$, CF$_2$H, CFH$_2$, Cl, Br, I, a C$_6$-C$_{12}$ aryl or a three- to seven-membered aromatic heterocycle; and R$_7$ is C$_1$-C$_6$ alkyl, C$_1$-C$_6$ haloalkyl, C$_1$-C$_6$ sulfonylakyl, C$_1$-C$_6$ alkylamino, CF$_3$, CF$_2$H, CFH$_2$, a C$_6$-C$_{12}$ aryl or a three- to seven-membered aromatic heterocycle, L, R$_A$, R$_B$, R$_1$, R$_6$, R$_7$, the C$_6$-C$_{12}$ aryl and the three- to seven-membered aromatic heterocycle being each independently unsubstituted or, when possible, substituted with at least one substituent chosen from C$_1$-C$_6$ alkyl, C$_1$-C$_6$ alkoxy, C$_1$-C$_6$ hydroxyalkyl, C$_1$-C$_6$ alkythio, C$_1$-C$_6$ thioalkyl, C$_1$-C$_6$ haloalkyl, C$_1$-C$_6$ sulfonylakyl, CN, C$_1$-C$_6$ aminoalkyl, C$_1$-C$_6$ alkylamino, CF$_3$, CF$_2$H, CFH$_2$, F, Cl, Br and I, or a pharmaceutically acceptable salt, solvate or prodrug thereof.

For example, the compound of Formula I is a compound of Formula IA:

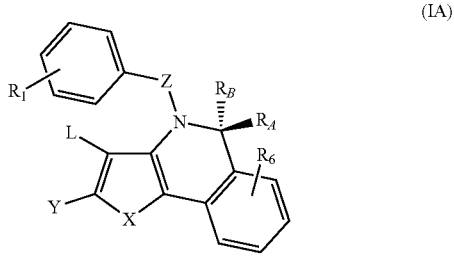

(IA)

L is H, C$_1$-C$_3$ alkyl, C$_1$-C$_3$ alkoxy, C$_1$-C$_3$ hydroxyalkyl, C$_1$-C$_3$ alkythio, C$_1$-C$_3$ thioalkyl, C$_1$-C$_3$ sulfonylakyl, C$_1$-C$_3$ aminoalkyl, C$_1$-C$_3$ alkylamino, ON, CF$_3$, CF$_2$H, CFH$_2$, F, Cl, Br, I;

X is S, O, NR$_7$ or NH;

Y is F, Cl, Br, I, H, CH$_3$, CF$_3$, CHF$_2$, CF$_2$H or CN;

Z is SO$_2$, CO or CH$_2$;

R$_A$ and R$_B$ are each independently H, C$_1$-C$_3$ alkyl, C$_1$-C$_3$ hydroxyalkyl, C$_1$-C$_3$ sulfonylakyl, C$_1$-C$_3$ alkylamino, CF$_3$, CF$_2$H, CFH$_2$, F;

R$_1$ is C$_1$-C$_3$ alkyl, C$_1$-C$_3$ alkoxy, C$_1$-C$_3$ hydroxyalkyl, C$_1$-C$_3$ sulfonylakyl, C$_1$-C$_3$ aminoalkyl, C$_1$-C$_3$ alkylamino, CN, CF$_3$, CF$_2$H, CFH$_2$, F, Cl, Br or I;

R$_6$ is C$_1$-C$_3$ alkyl, C$_1$-C$_3$ alkoxy, C$_1$-C$_3$ hydroxyalkyl, C$_1$-C$_3$ sulfonylakyl, C$_1$-C$_3$ aminoalkyl, C$_1$-C$_3$ alkylamino, CN, CF$_3$, CF$_2$H, CFH$_2$, F, Cl, Br or I; and R$_7$ is is C$_1$-C$_6$ alkyl, C$_1$-C$_6$ haloalkyl, C$_1$-C$_6$ sulfonylakyl, C$_1$-C$_6$ alkylamino, CF$_3$, CF$_2$H, CFH$_2$, a C$_6$-C$_{12}$ aryl or a three- to seven-membered aromatic heterocycle;

L, R$_A$, R$_B$, R$_1$, R$_6$, the C$_6$-C$_{12}$ aryl and the three- to seven-membered aromatic heterocycle being each independently unsubstituted or substituted with at least one substituent chosen from C$_1$-C$_6$ alkyl, C$_1$-C$_6$ alkoxy, C$_1$-C$_6$ hydroxyalkyl, C$_1$-C$_6$ alkythio, C$_1$-C$_6$ thioalkyl, C$_1$-C$_6$ haloalkyl, F, Cl, Brand I, or a pharmaceutically acceptable salt, solvate or prodrug thereof.

For example, the compound of Formula I is a compound of Formula IA:

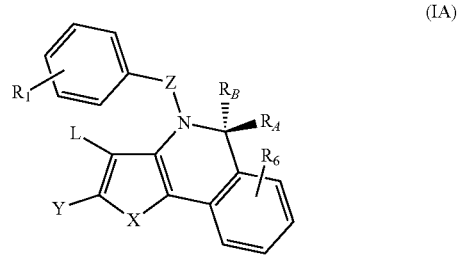

(IA)

L is H;
X is S;
Z is SO$_2$, CO or CH$_2$;
Y is F, Cl, Br or I;
R$_A$ is H;
R$_B$ is H;
R$_1$ is in para position with respect to Z and is chosen from C$_1$-C$_3$ alkyl, C$_1$-C$_3$ alkoxy, C$_1$-C$_3$ hydroxyalkyl, C$_1$-C$_3$ sulfonylakyl, C$_1$-C$_3$ aminoalkyl, C$_1$-C$_3$ alkylamino, CN, CF$_3$, CF$_2$H, CFH$_2$, F, Cl, Br and I; and
R$_6$ is C$_1$-C$_3$ alkyl, C$_1$-C$_3$ alkoxy, C$_1$-C$_3$ hydroxyalkyl, C$_1$-C$_3$ sulfonylakyl, C$_1$-C$_3$ aminoalkyl, C$_1$-C$_3$ alkylamino, CN, CF$_3$, CF$_2$H, CFH$_2$, F, Cl, Br or I,
R$_1$, R$_6$, the C$_6$-C$_{12}$ aryl and the three- to seven-membered aromatic heterocycle being each independently unsubstituted or substituted with at least one substituent chosen from C$_1$-C$_6$ alkyl, C$_1$-C$_6$ alkoxy, C$_1$-C$_6$ hydroxyalkyl, C$_1$-C$_6$ alkythio, C$_1$-C$_6$ thioalkyl, C$_1$-C$_6$ haloalkyl, F, Cl, Br and I, or a pharmaceutically acceptable salt, solvate or prodrug thereof.

For example,
L is H;
Z is SO$_2$;
Y is H, F, Cl, Br, I or C$_6$-C$_{12}$ aryl;
R$_A$ is H;
R$_B$ is H;
R$_1$ is H, C$_1$-C$_6$ alkyl, C$_1$-C$_3$ haloalkyl or C$_1$-C$_3$ alkoxy; and
R$_6$ is H.

For example,
L is H;
Z is SO$_2$;
Y is H, F, Cl, Br, I or phenyl;
R$_A$ is H;
R$_B$ is H;
R$_1$ is H, C$_1$-C$_3$ alkyl, CF$_3$ or methoxy; and
R$_6$ is H.

For example, the compound is chosen from

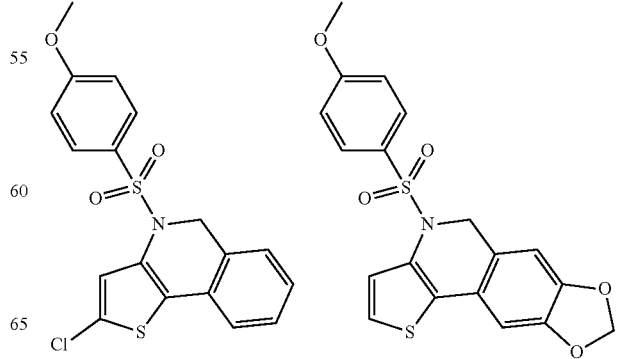

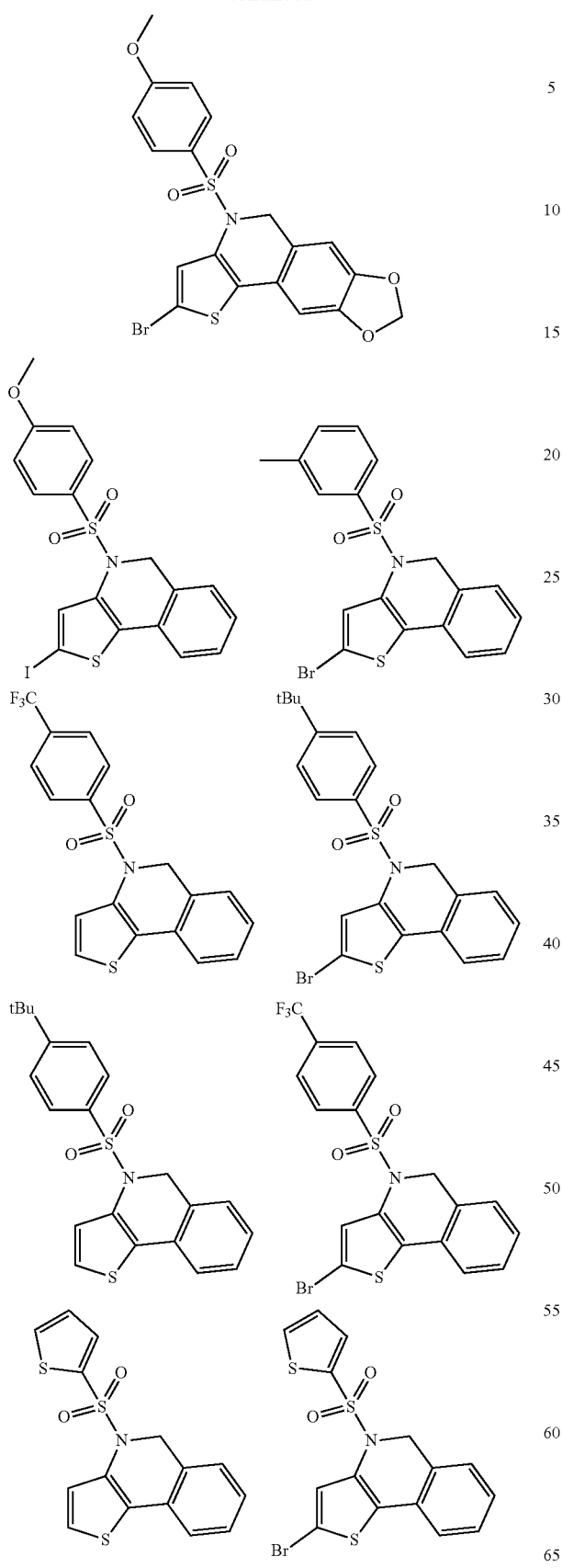
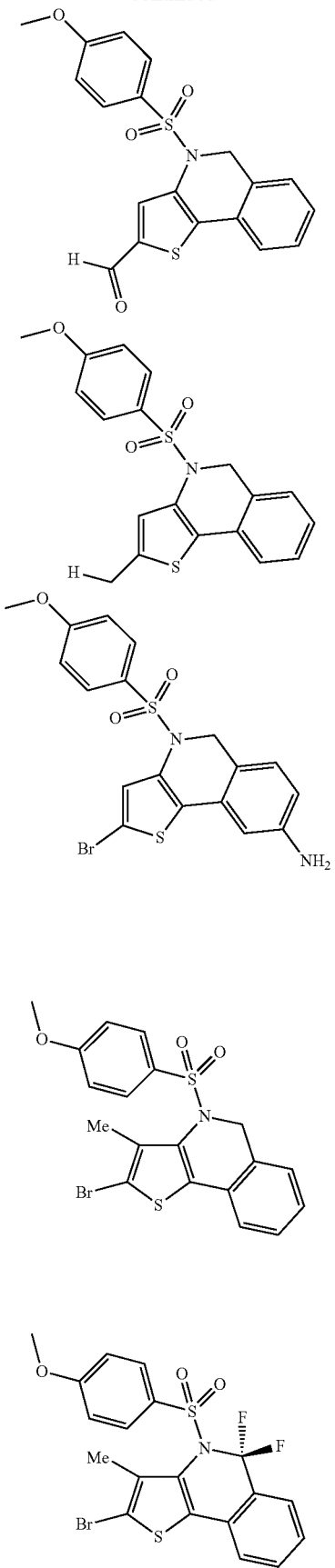

27
-continued
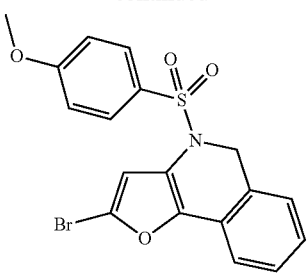
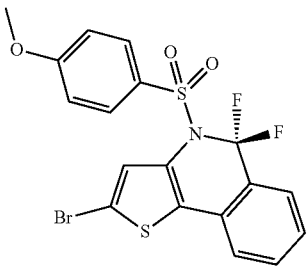
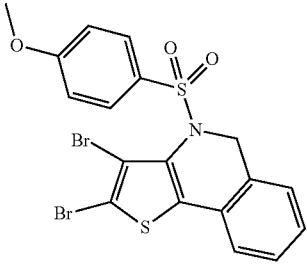
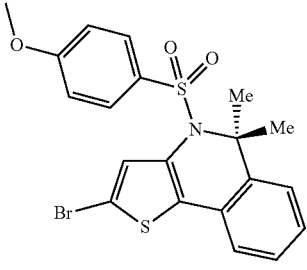
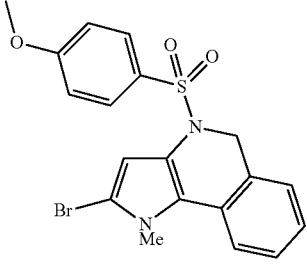
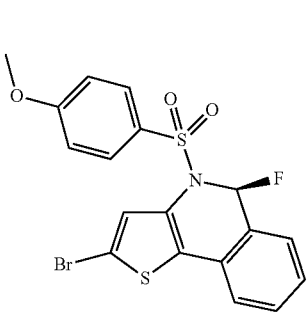
28
-continued
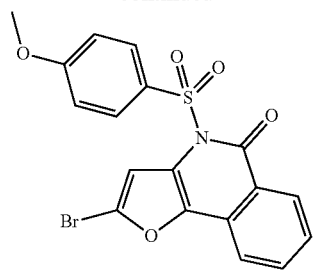
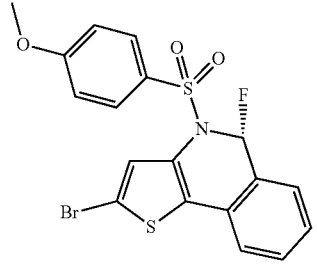
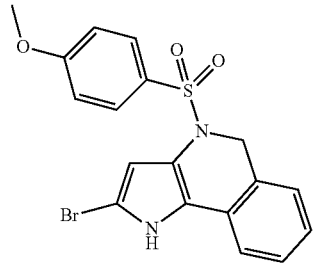
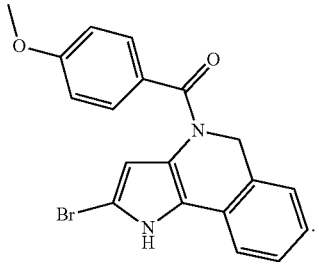
For example, the compound is
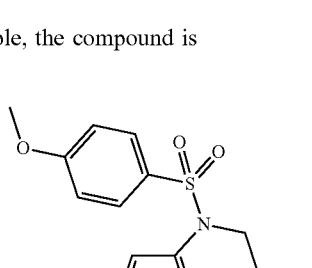
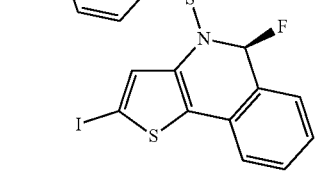

-continued
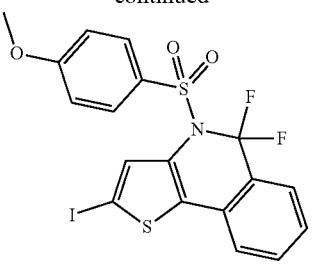
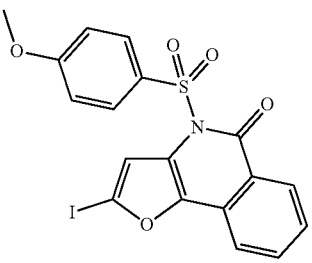
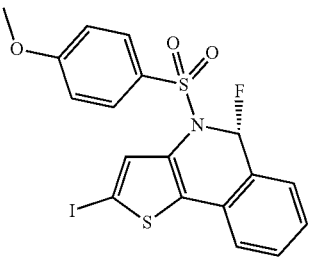
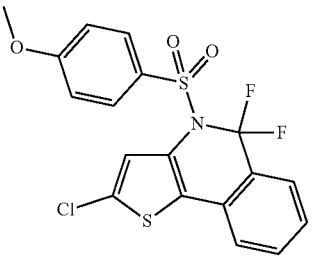
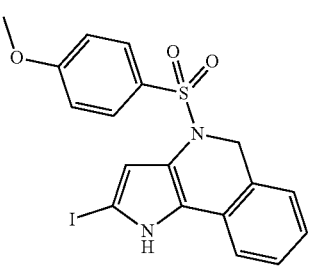
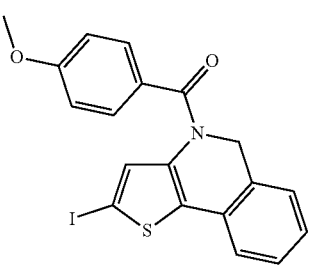
-continued
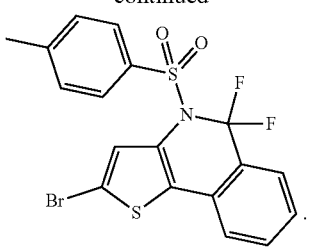
For example, the compound is chosen from
C87
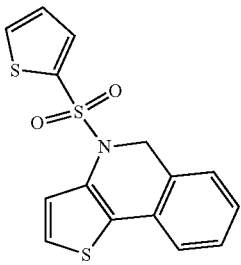
C75
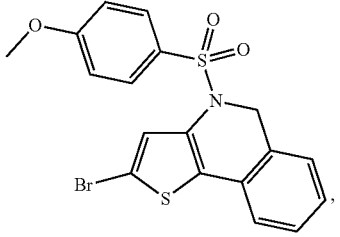 [SMILES: COc1ccc(S(=O)(=O)N2Cc3ccccc3-c3sc(Br)cc32)cc1]
C90
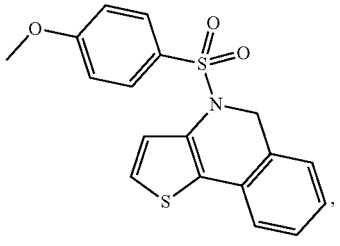
C207
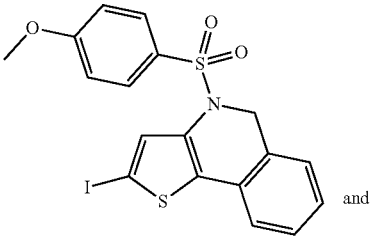
and
C91
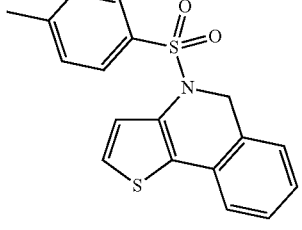

For example, the compound is

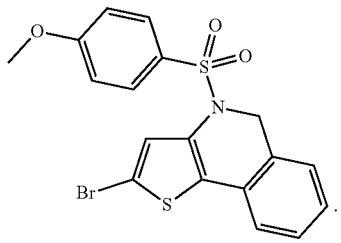

C75

According to a further aspect, there is provided herein a use of a compound of Formula I for selectively inhibiting growth in a cancer cell.

According to another aspect, there is provided herein a use of a compound of Formula I for disrupting centrosome integrity, preventing and/or reducing centrosome clustering, declustering centrosomes, regulating centrosome clustering and/or inducing microtubule depolymerization in a cancer cell.

According to yet another aspect, there is provided herein a use of a combination of a compound of Formula I and an anti-cancer agent and/or an anti-mitotic agent for selectively inhibiting growth in a cancer cell.

For example, inhibiting growth in the cancer cell is selective.

For example, inhibiting growth comprises inducing mitotic arrest in the cancer cell.

According to another aspect, there is provided herein a use of a compound of Formula I for the treatment of cancer in a subject.

According to another aspect, there is provided herein a use of a combination of a Formula I and an anti-cancer agent and/or an anti-mitotic agent for the treatment of cancer in a subject.

According to another aspect, there is provided herein a use of a compound of Formula I in combination with an anti-cancer agent and/or an anti-mitotic agent for increasing selectivity of the anti-cancer agent and/or the anti-mitotic agent to a cancer cell.

For example, the compound herein disclosed and/or the combination comprising the compound and an anti-cancer agent and/or an anti-mitotic agent herein disclosed are comprised in a composition that comprises an injectable dosage form. For example, the composition is administered by intratumoral injection.

For example, the compound herein disclosed and/or the combination comprising the compound and an anti-cancer agent and/or an anti-mitotic agent herein disclosed are comprised in a composition administered by parenteral, intravenous, subcutaneous, intramuscular, intracranial, intraspinal, intracisternal, intraperitoneal, intranasal, aerosol or oral administration.

According to a further aspect, there is provided herein a compound of Formula IA:

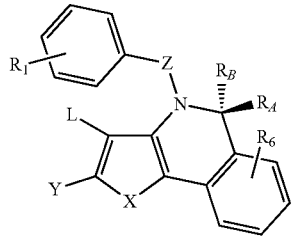

(IA)

L is H, $C_1$-$C_3$ alkyl, $C_1$-$C_3$ alkoxy, $C_1$-$C_3$ thioalkyl, $C_1$-$C_3$ haloalkyl, CN, $CF_3$, $CF_2H$, $CFH_2$, F, Cl, Br or I;

X is S, O, $NR_7$ or NH;

Y is F, Cl, Br, I, H, $CH_3$, $CF_3$, $CHF_2$, $CF_2H$ or CN;

Z is $SO_2$, CO or $CH_2$;

$R_A$ and $R_B$ are each independently H, Me, Et, $CF_3$, $CF_2H$, $CFH_2$, F or Cl;

$R_1$ is $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br or I;

$R_6$ is $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br or I; and $R_7$ is $C_1$-$C_6$ alkyl, $C_1$-$C_6$ haloalkyl, $C_1$-$C_6$ sulfonylakyl, $C_1$-$C_6$ alkylamino, $CF_3$, $CF_2H$, $CFH_2$, a $C_6$-$C_{12}$ aryl or a three- to seven-membered aromatic heterocycle, L, $R_A$, $R_B$, $R_1$, $R_6$, the $C_6$-$C_{12}$ aryl and the three- to seven-membered aromatic heterocycle being each independently unsubstituted or substituted with at least one substituent chosen from $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, F, Cl, Brand I, or a pharmaceutically acceptable salt, solvate or prodrug thereof.

For example,

L is H;

X is S;

Z is $SO_2$, CO or $CH_2$;

Y is F, Cl, Br or I;

$R_A$ is H;

$R_B$ is H;

$R_1$ is in para position with respect to Z and is chosen from $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br and I; and $R_6$ is $C_1$-$C_3$ alkyl, $C_1$-$C_3$ alkoxy, $C_1$-$C_3$ hydroxyalkyl, $C_1$-$C_3$ sulfonylakyl, $C_1$-$C_3$ aminoalkyl, $C_1$-$C_3$ alkylamino, CN, $CF_3$, $CF_2H$, $CFH_2$, F, Cl, Br or I, $R_1$, $R_6$, the $C_6$-$C_{12}$ aryl and the three- to seven-membered aromatic heterocycle being each independently unsubstituted or substituted with at least one substituent chosen from $C_1$-$C_6$ alkyl, $C_1$-$C_6$ alkoxy, $C_1$-$C_6$ hydroxyalkyl, $C_1$-$C_6$ alkythio, $C_1$-$C_6$ thioalkyl, $C_1$-$C_6$ haloalkyl, F, Cl, Br and I, or a pharmaceutically acceptable salt, solvate or prodrug thereof.

For example,

L is H;

Z is $SO_2$;

Y is H, F, Cl, Br, I or $C_6$-$C_{12}$ aryl;

$R_A$ is H;

$R_B$ is H;

R₁ is H, $C_1$-$C_6$ alkyl, $C_1$-$C_3$ haloalkyl or $C_1$-$C_3$ alkoxy; and
R₆ is H.
For example,
L is H;
Z is $SO_2$;
Y is H, F, Cl, Br, I or phenyl;
$R_A$ is H;
$R_B$ is H;
R₁ is H, $C_1$-$C_3$ alkyl, $CF_3$ or methoxy; and
R₆ is H.
For example, the compound is chosen from
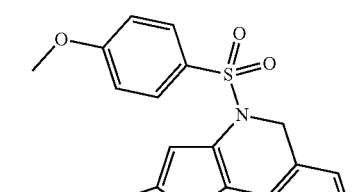
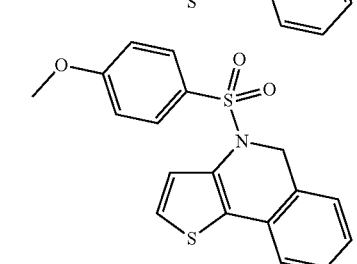
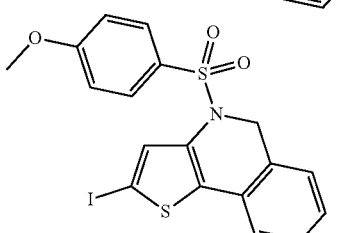
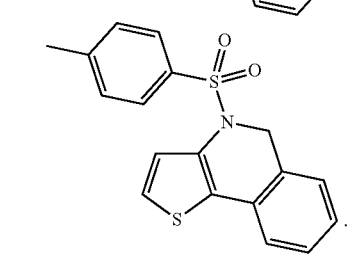
For example, the compound is
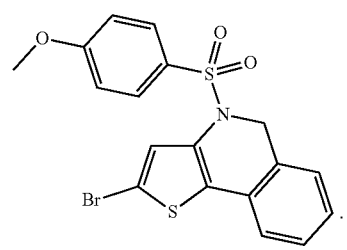
According to a further aspect, there is provided herein a compound chosen from:
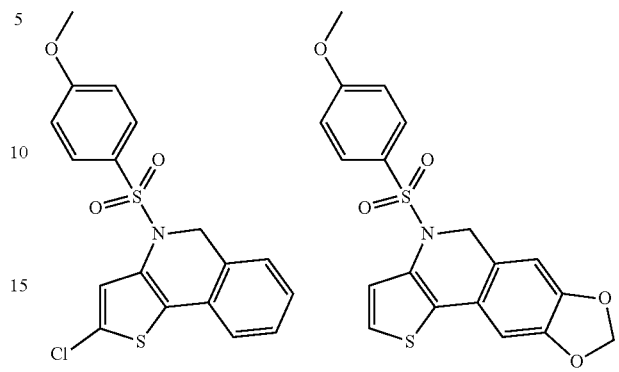
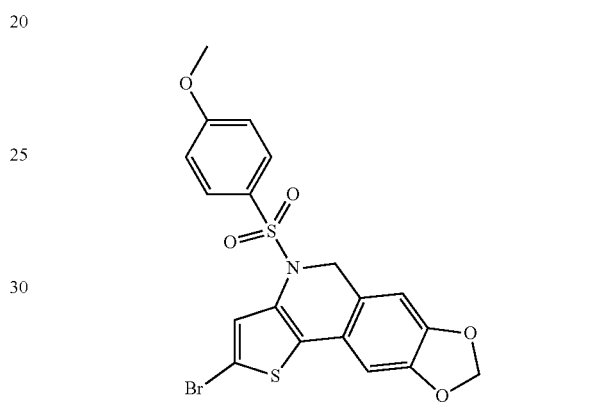
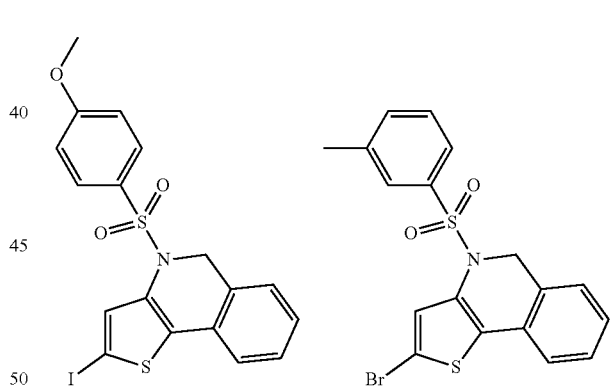
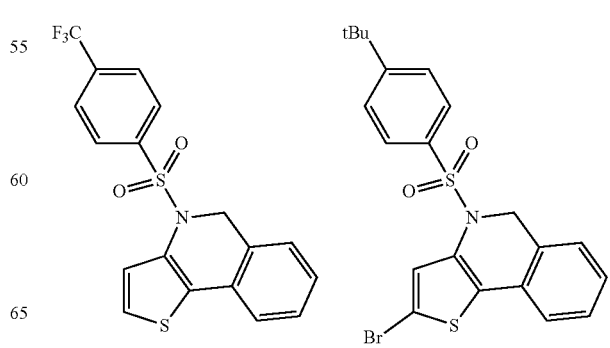

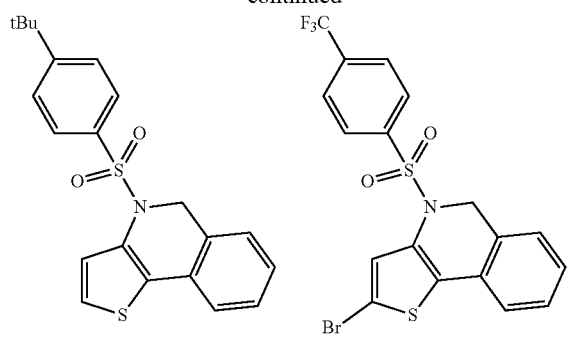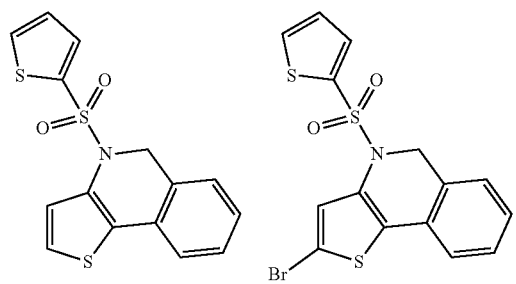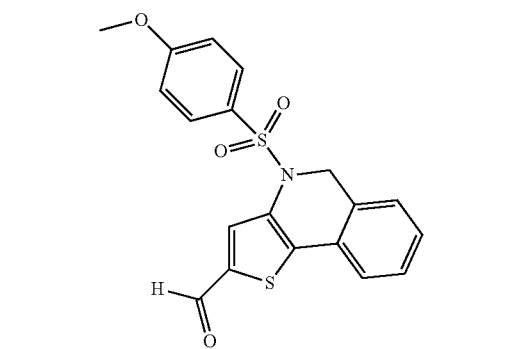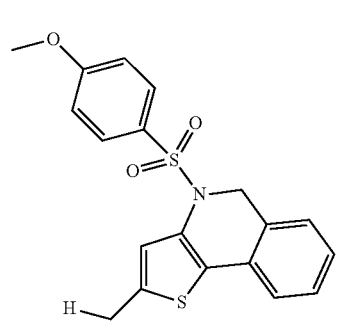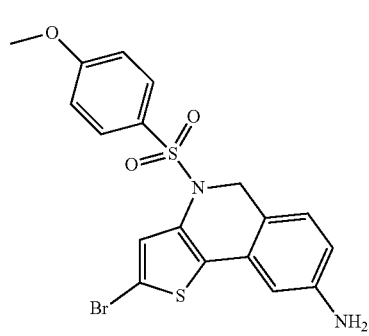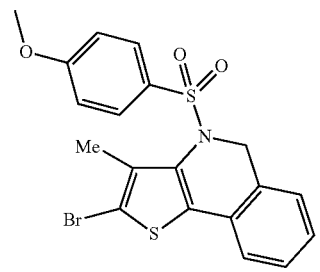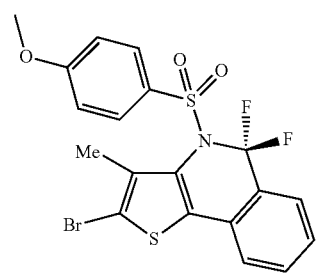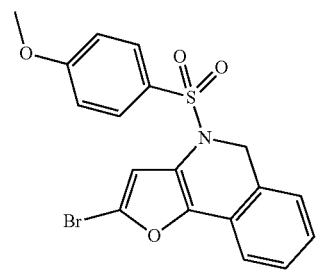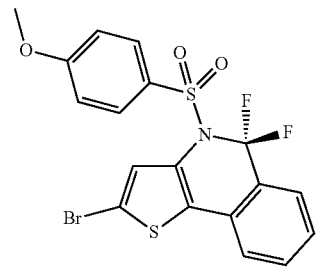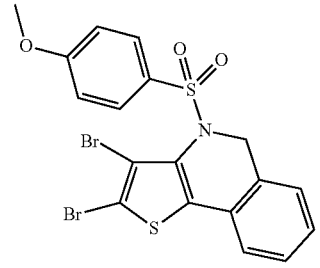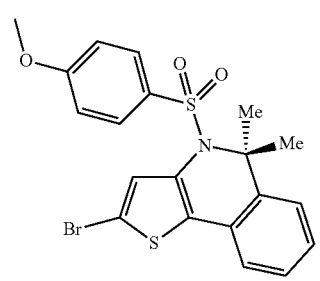

-continued
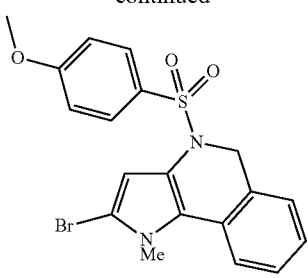
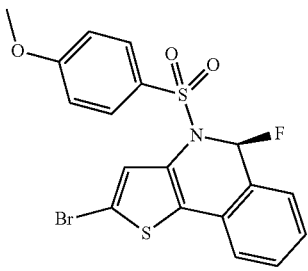
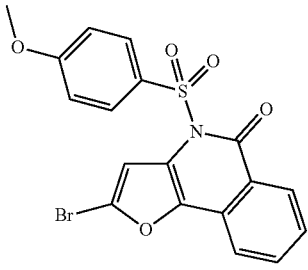
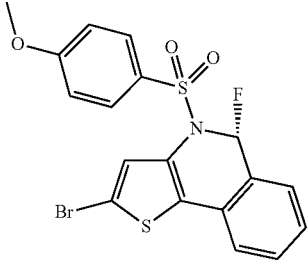
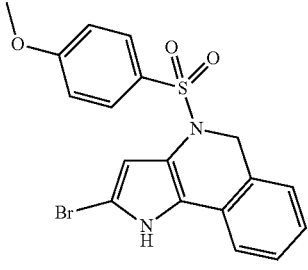
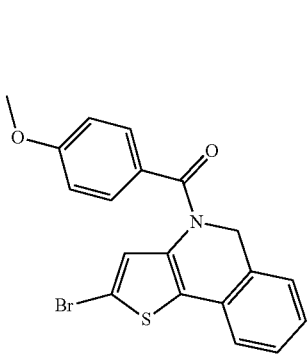
-continued
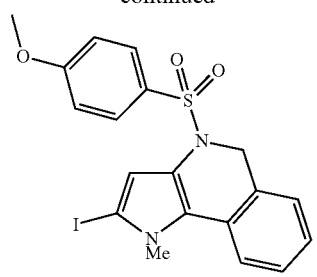
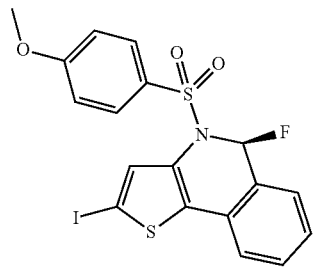
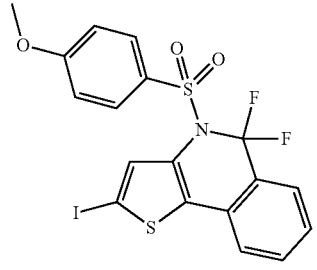
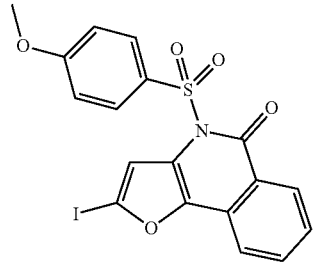
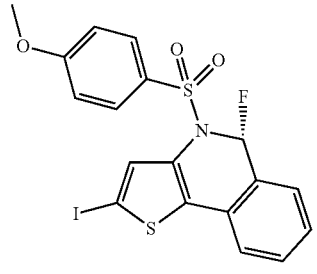
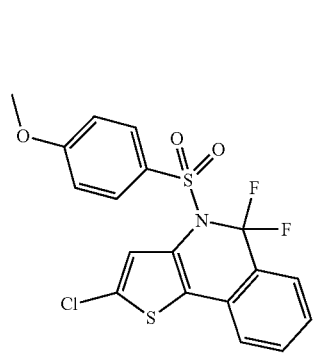

-continued

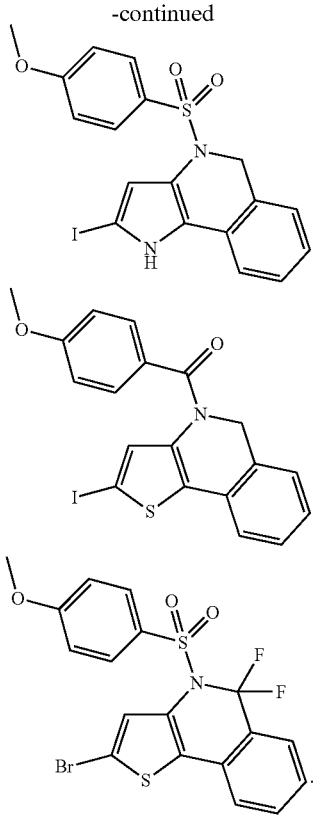

EXAMPLES

These examples are not to be construed as limiting the scope of the present disclosure in any way.

Example 1

A family of high-quality compounds with drug-like properties and potential for medicinal use were identified. A novel synthesis was designed to improve the yield of these compounds in a cost-effective manner and their ability to treat cancers was evaluated. More specifically, a novel synthesis for a high quality, small molecular weight thienoisoquinoline scaffold was designed[10,11].

19 variants with different structural modifications have been made. Table 3 below shows $IC_{50}$ not to values for a subset of thienoisoquinoline compounds in HeLa (cervical adenocarcinoma), BT549 (breast ductal carcinoma), A549 (lung carcinoma) and MCF-7 (mammary gland carcinoma) cells and HFF1 (fibroblast) and MCF-10A (mammary gland fibrocystic disease) non-cancer cells. Several thienoisoquinoline derivatives, for example C75, C91 and C207, show higher efficacy, i.e. more strongly affect viability, in cancer cells vs. non-cancer cells. In particular, it is shown that C75 causes death in multiple cancer cells with $IC_{50}$ values in the 100 nM range, including breast cancers (MCF7, BT549), lung cancer (A549), colorectal cancer (HCT116) in addition to HeLa cells (cervical cancer).

TABLE 3

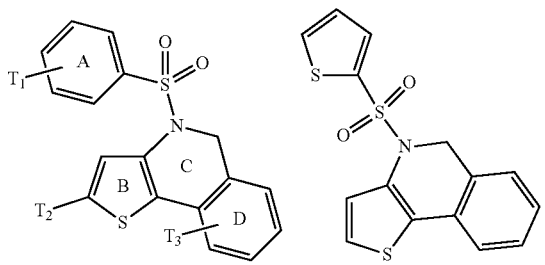

| | $T_1$ | $T_2$ | $T_3$ | $IC_{50}$-HeLa | $IC_{50}$-BT549 | $IC_{50}$-A549 | $IC_{50}$-MCF-7 | $IC_{50}$-HFF-1 | $IC_{50}$-MCF10A |
|---|---|---|---|---|---|---|---|---|---|
| C39 | 3-Me | H | H | >1 μM | — | — | — | — | — |
| C71 | 4-Me | Ph | H | >1 μM | — | — | — | — | — |
| C74 | 4-Me | Br | H | >1 μM | — | — | — | — | — |
| C75 | 4-OMe | Br | H | 27 nM | 158 nM | 109 nM | 101 nM | 467 nM | 309 nM |
| C87 | — | — | — | 845 nM | 4198 nM | 750 nM | 2463 nM | >1000 nM | 539 nM |
| C90 | 4-OMe | H | H | 177 nM | — | — | 149 nM | — | — |
| C91 | 4-Me | H | H | 197 nM | — | — | 1015 nM | 920 nM | — |
| C93 | 3-Me | Br | H | >1 μM | — | — | — | — | — |
| C108 | 4-$CF_3$ | H | H | >1 μM | — | — | — | — | — |
| C200 | 4-$CF_3$ | Br | H | >1 μM | — | — | — | — | — |
| C201 | 4-tBu | Br | H | >1 μM | — | — | — | — | — |
| C207 | 4-OMe | I | H | 70 nM | 178 nM | — | 86 nM | 150 nM | — |
| C208 | 4-OMe | Cl | H | | 204 nM | — | — | — | — |

C75 was further tested and found to cause mitotic arrest in HeLa cells. The bright-field images in FIG. 1A show fields of view of HeLa cells treated with (dimethyl sulfoxide) DMSO or 500 nM of C75. Further testing of C75 revealed it selectively causes mitotic arrest in HeLa cells in comparison to HFF1 (non-cancerous fibroblast) cells at concentrations in the nanomolar range (FIG. 1B, Table 3). While the mitotic spindle was not affected in HeLa cells treated with DMSO or in HFF1 cells treated with DMSO or 300 nM C75, spindle organization was perturbed in HeLa cells treated with 300 nM C75. Centrosomes were fragmented or declustered and microtubules were completely absent in HeLa cells treated with 750 nM C75 (FIG. 1C). Higher concentrations of C75 caused spindle phenotypes in HFF-1 cells, but they were quite different in comparison to HeLa cells (FIG. 1C).

Figure 2:
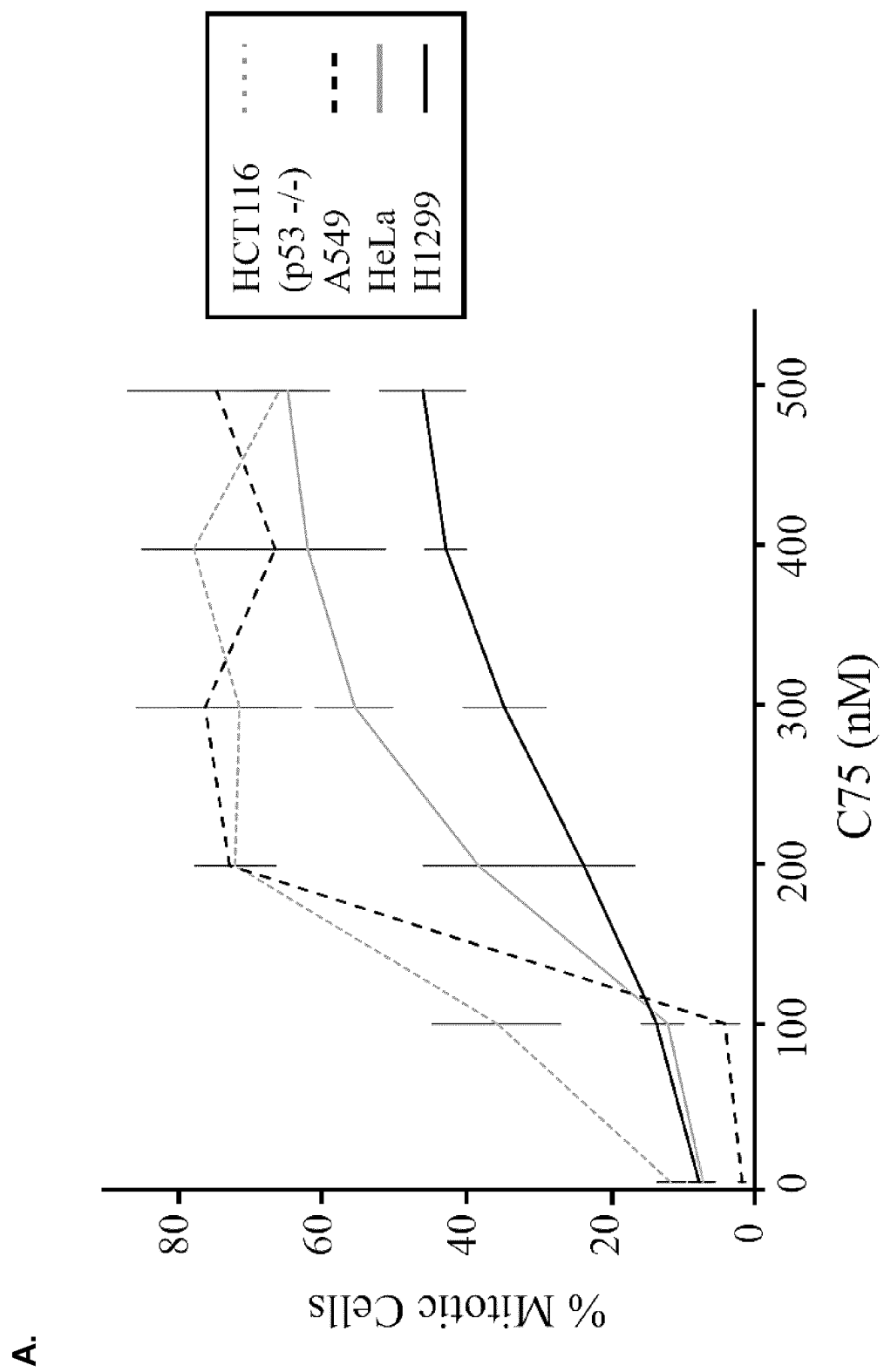
FIGS. 2A, 2B, 2C, 2E and 2F show that C75 selectively causes mitotic arrest in cancer cells and targets centrosomes.
FIG. 2D) shows a schematic of how HeLa cells in metaphase were treated with C75 or the tubulin-targeting drug nocodazole for 5 minutes, then the C75 and nocodazole drugs were washed out and cells were imaged after 40 minutes.
FIG. 2G) is a schematic showing the putative target for C75. Healthy cells have two centrosomes that separate and form a bipolar spindle, while cancer cells have aberrant centrosomes that cluster to form 'pseudo' bipolar spindles, and C75 may target this process and their integrity.
Figure 2:
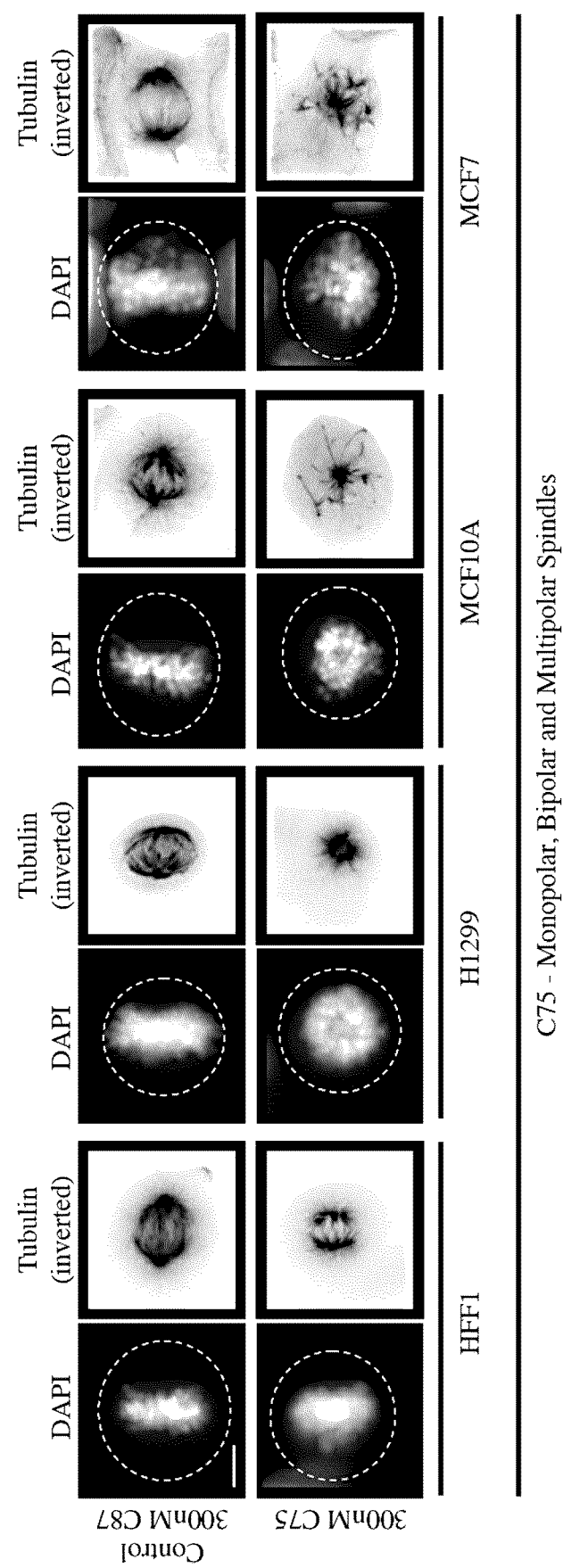
Figure 2:
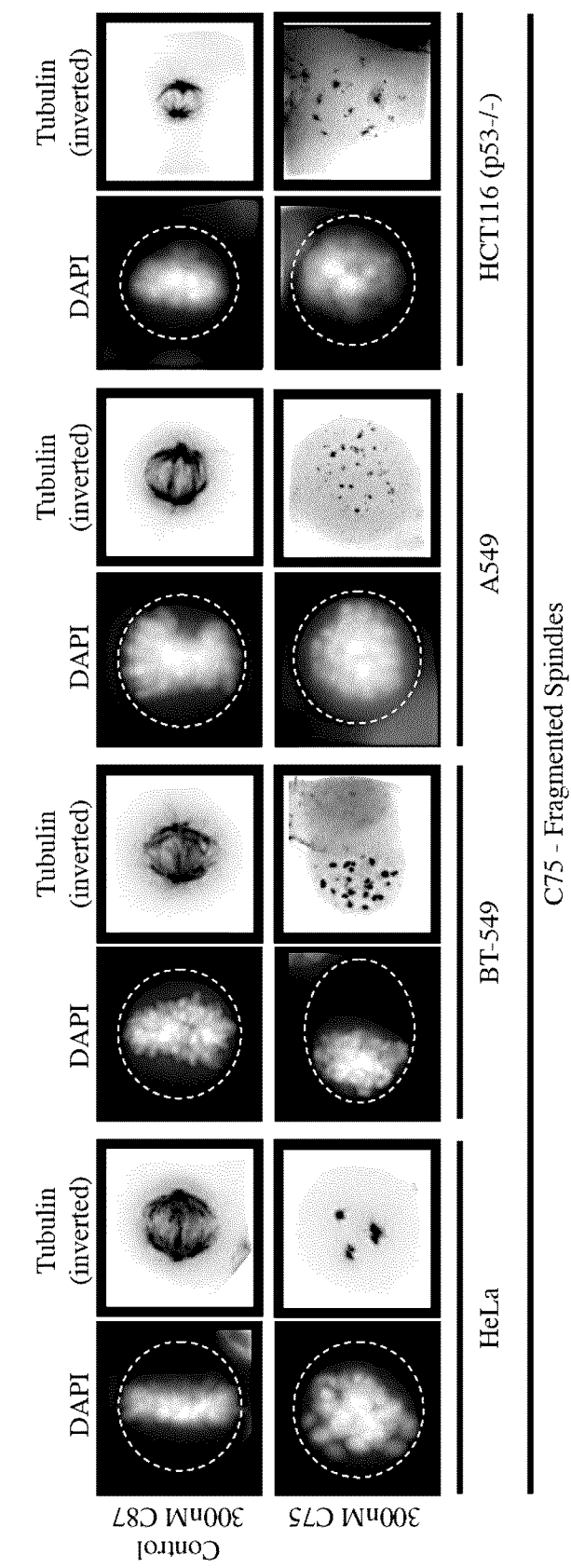
Figure 2:
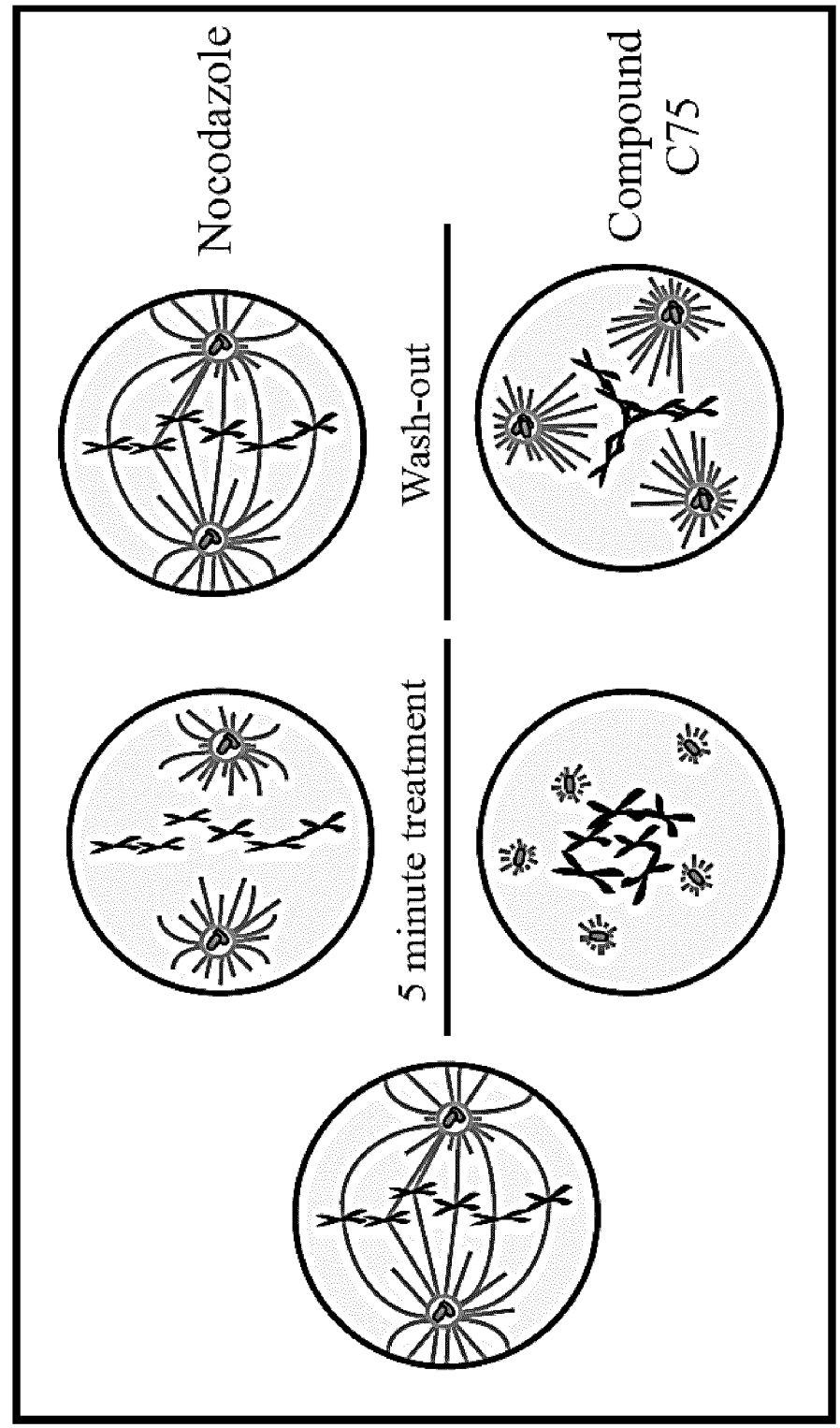
Figure 2:
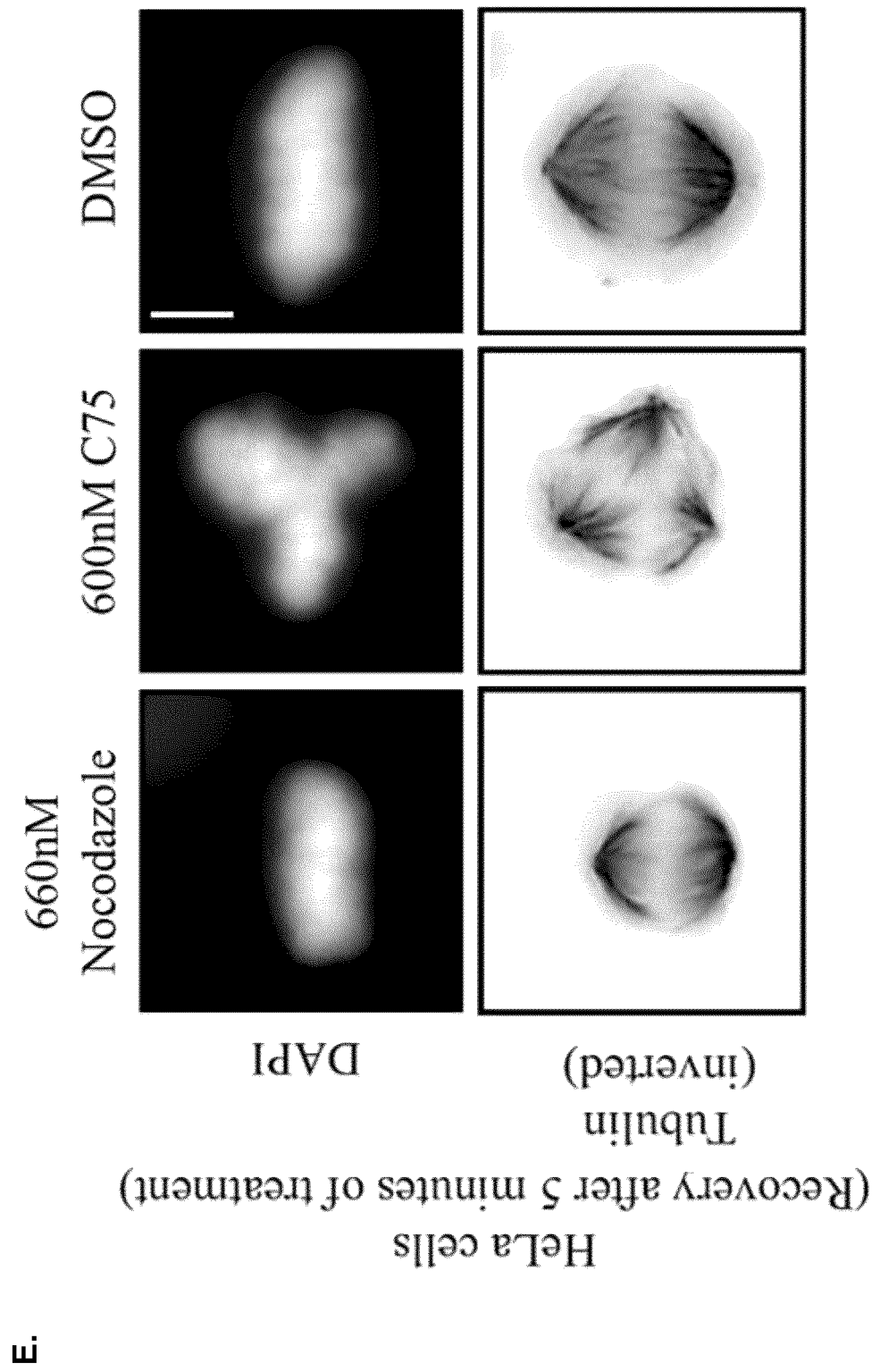
Figure 2:
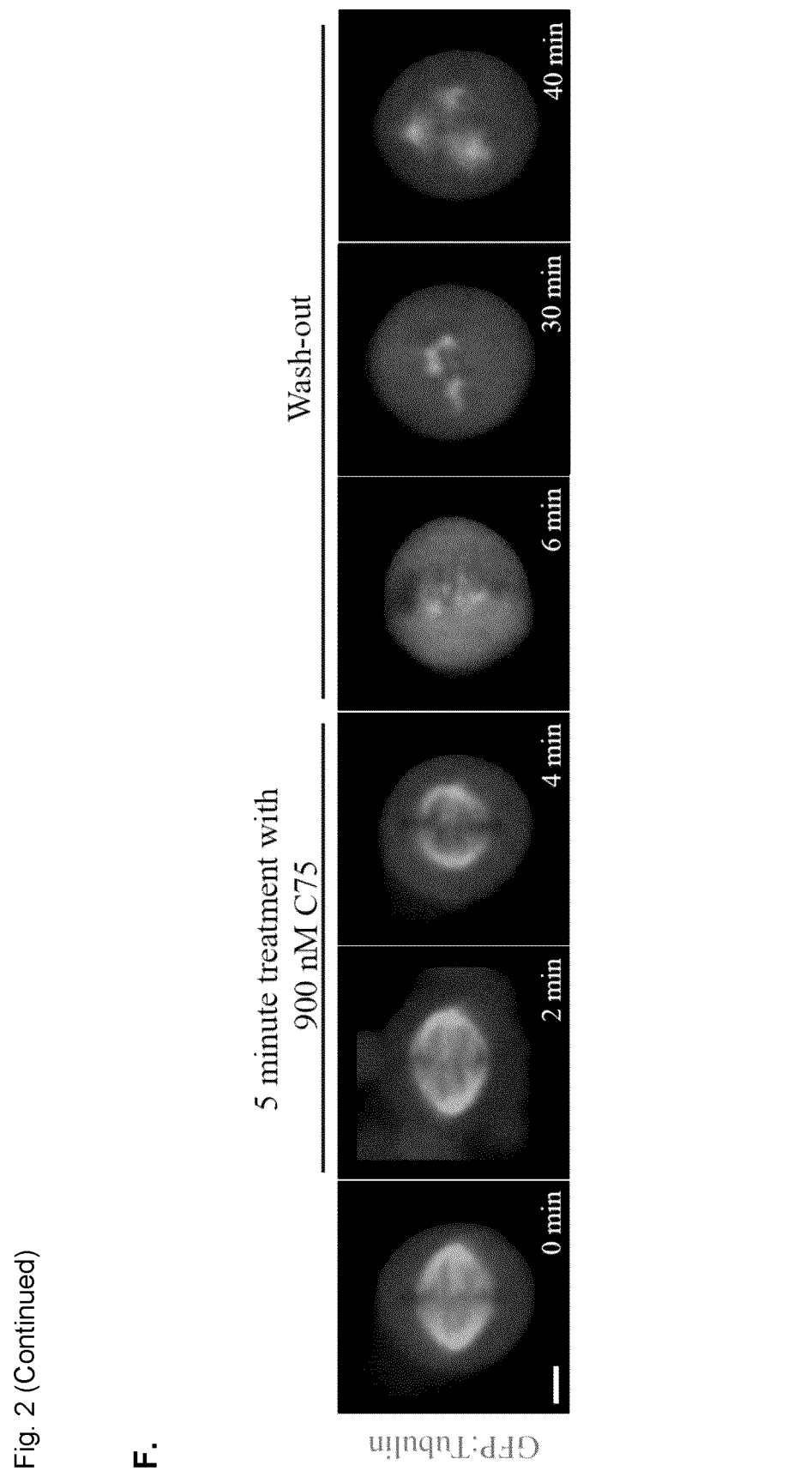
Figure 2:
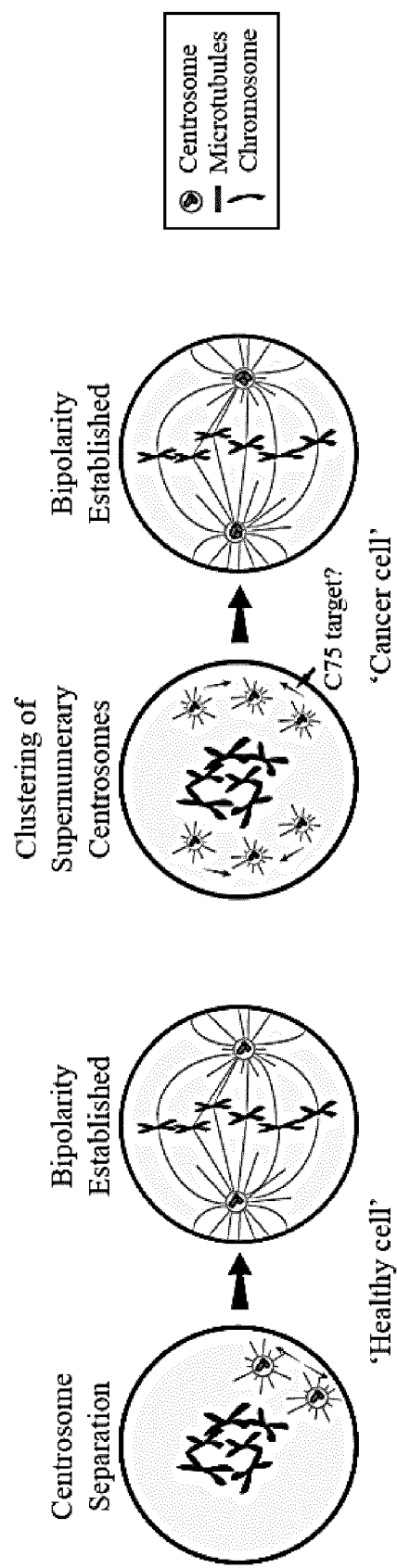

C75 was also tested for efficacy in different cancer cell lines. In HCT116 (colorectal cancer), HeLa (cervical cancer) cells, A549 (lung cancer) cells and H1299 (non-small cell lung cancer) cells, 100-200 nM C75 caused mitotic arrest within one population double time (FIG. 2A). HCT116 cells appeared to be most responsive (increase at 100 nM), while H1299 appeared to be the least responsive (small increase at 200 nM). In addition, C75 was found to cause spindle phenotypes that varied depending on the cell type. While the majority of HFF1 cells had bipolar spindles after C75 treatment, H1299 cells, MCF-10A cells and MCF-7 cells, displayed a mix of monopolar, bipolar and multipolar spindles after C75 treatment (FIG. 2B). More severe spindle phenotypes were observed in HeLa cells, BT-549 cells, A549 cells and HCT116 cells after C75 treatment, where most of the spindles were severely fragmented (FIG. 2C). To further assess the role of C75 in affecting centrosomes, HeLa cells were treated with C75 for a short period of time (5 minutes), then C75 was removed and the cells were analyzed for spindle phenotypes (schematic in FIG. 2D). While in cells treated with nocodazole, a drug that causes microtubule depolymerization, bipolar spindles reformed, in cells treated with C75, tri- or multipolar spindles formed (FIG. 2E). In addition, live imaging revealed that within 4-6 minutes after exposure to C75, the centrosomes fragmented or declustered and microtubules rapidly collapsed with no visible polymers remaining. Microtubule polymers grew within ~20-30 minutes, but the spindles were tri- or multipolar (FIG. 2F). This emphasizes the ability of thienoisoquinoline compounds to affect centrosomes in comparison to other compounds that affect mitosis by targeting tubulin (FIG. 2G).

Example 3

The thienoisoquinoline compounds may also have potential for use in combinatorial therapies. Several known anti-cancer drugs cause mitotic arrest by disrupting microtubule dynamics, and have been used to combat a spectrum of cancers, including paclitaxel and vinblastine[12,13]. Taxanes (e.g. paclitaxel), vinca alkaloids (e.g. vinblastine) and other drugs such as colchicine and nocodazole bind to β-tubulin or to the α-β-tubulin interface.

Figure 3:
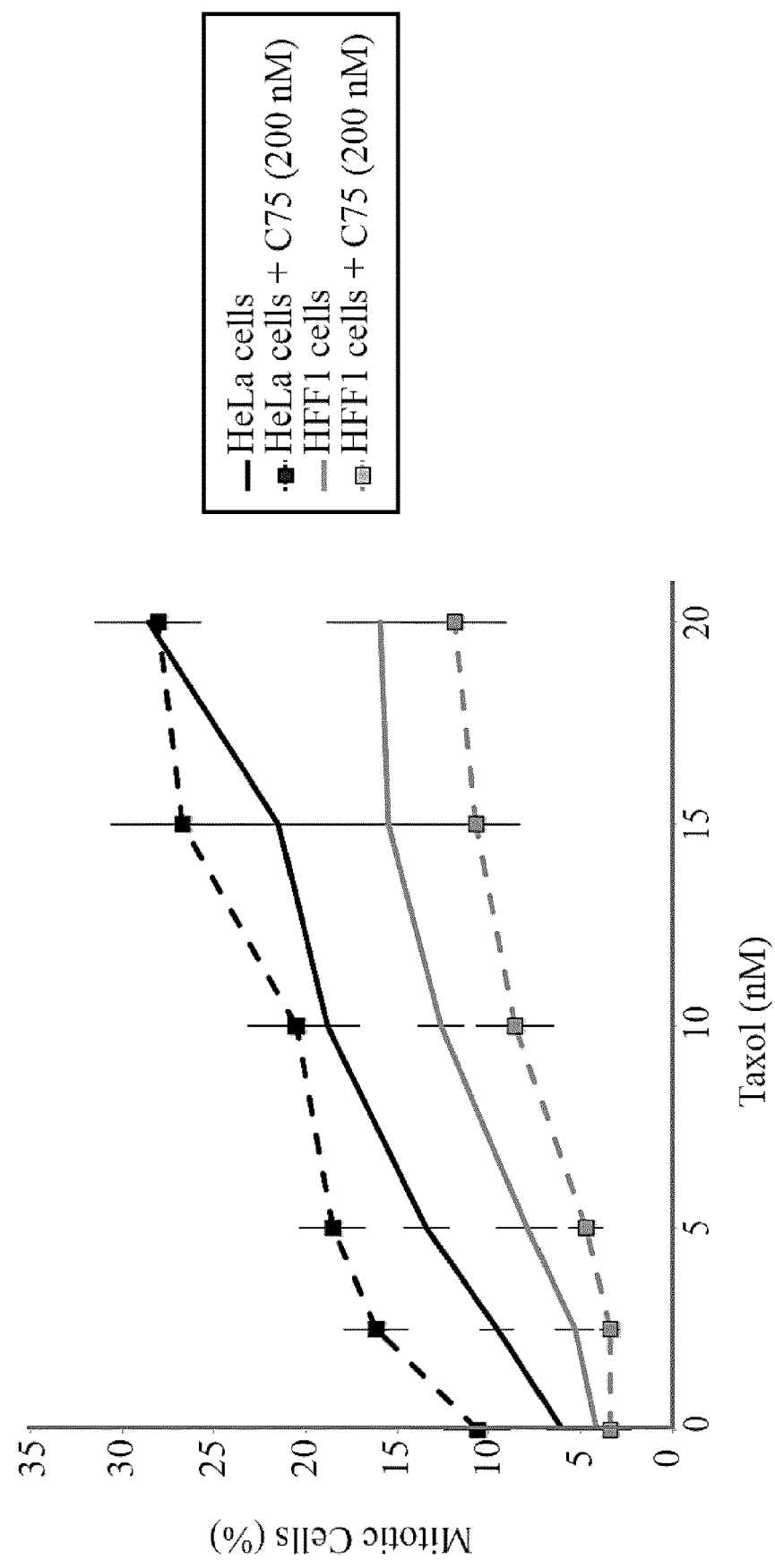
FIGS. 3A, 3B, 3C, 3D, 3E, 3F and 3G show that C75 enhances the selectivity of tubulin-targeting drugs for cancer cells.
Figure 3:
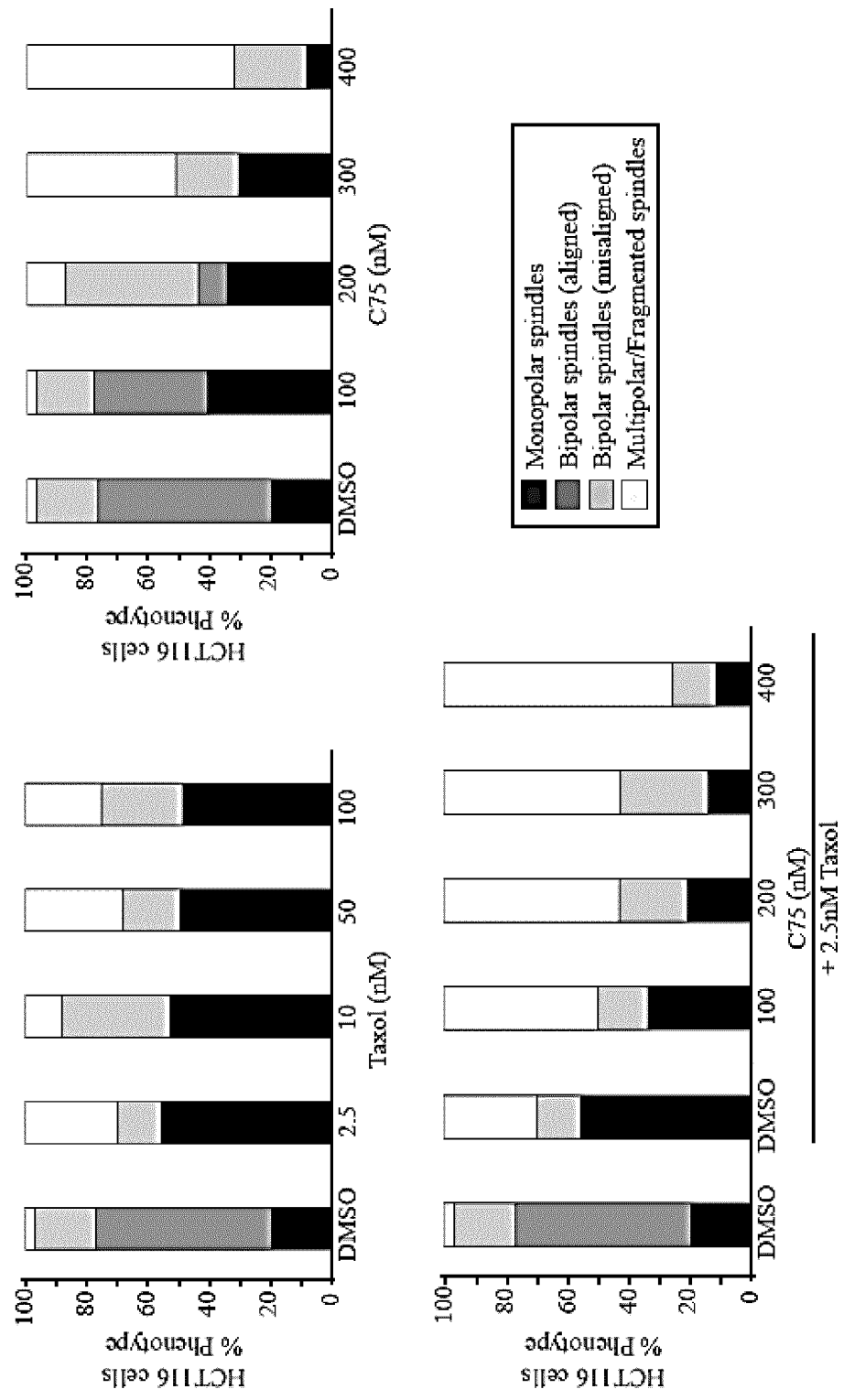
Figure 3:
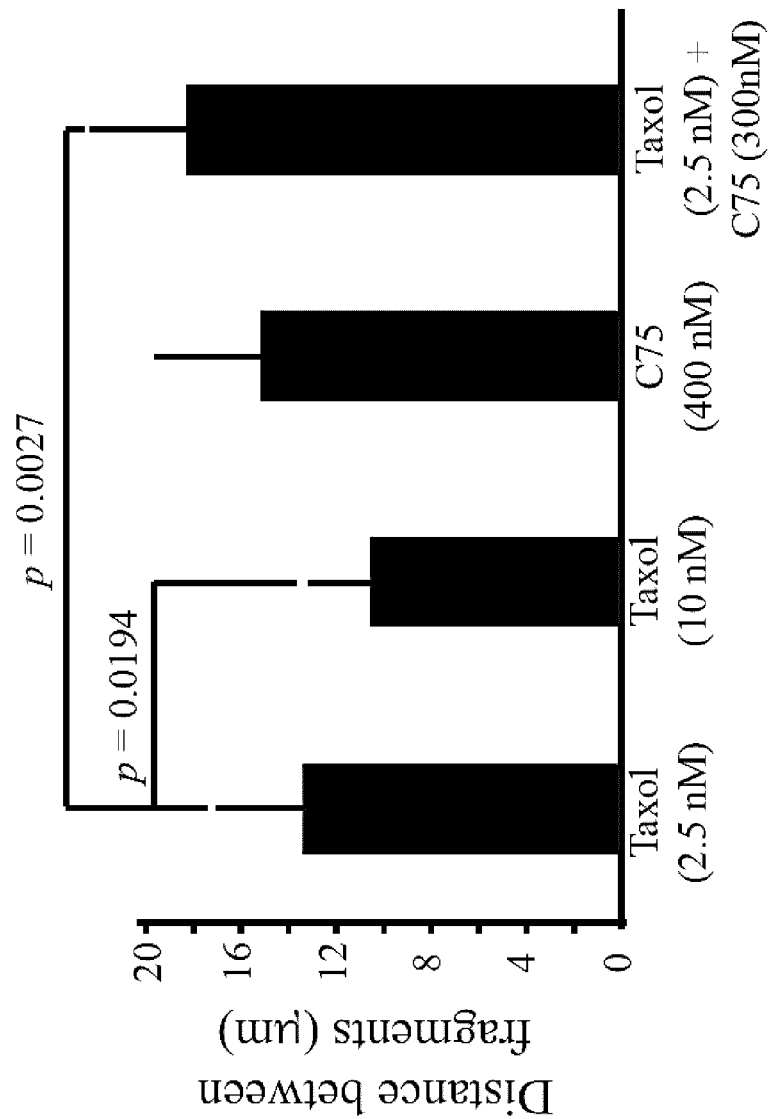
Figure 3:
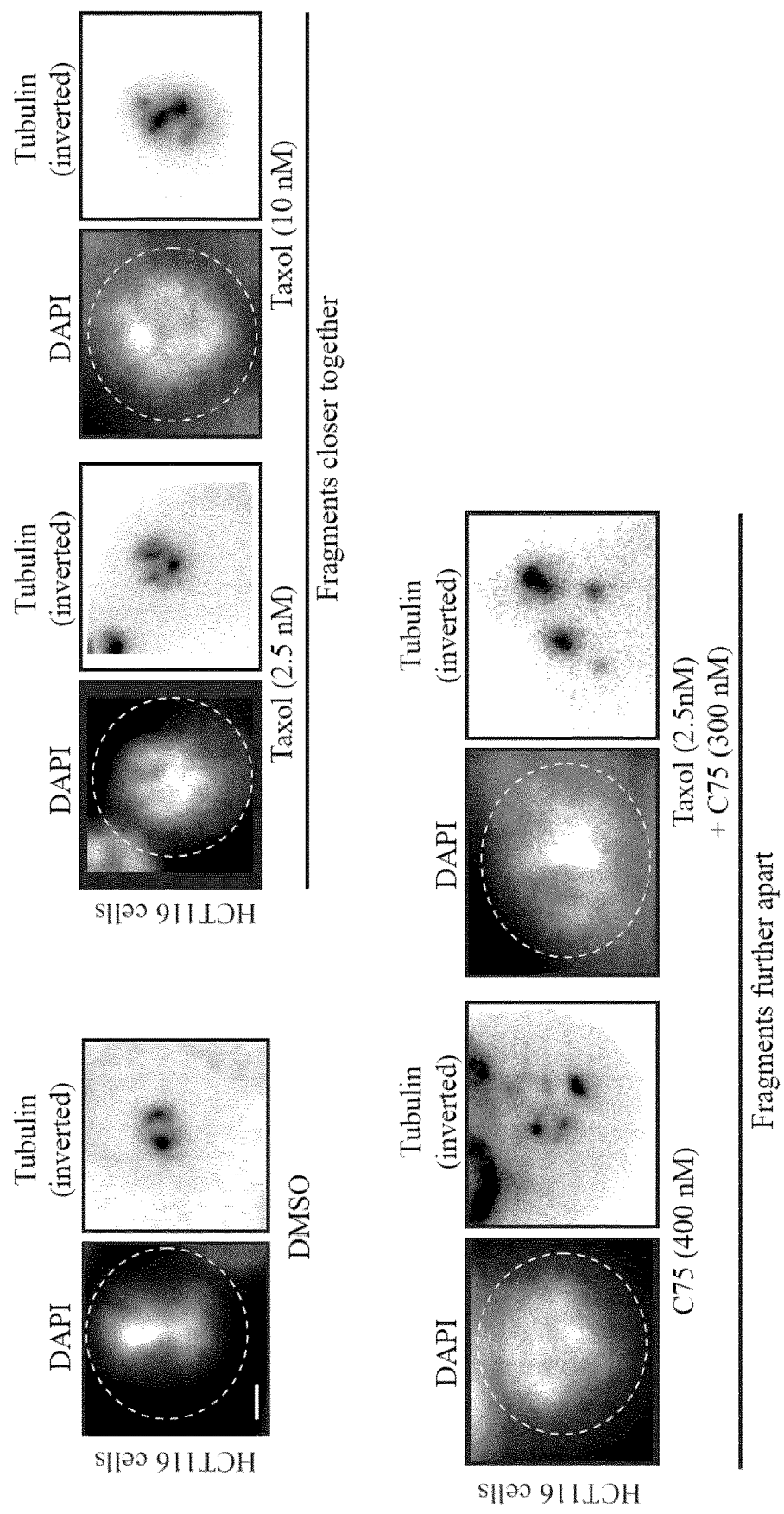
Figure 3:
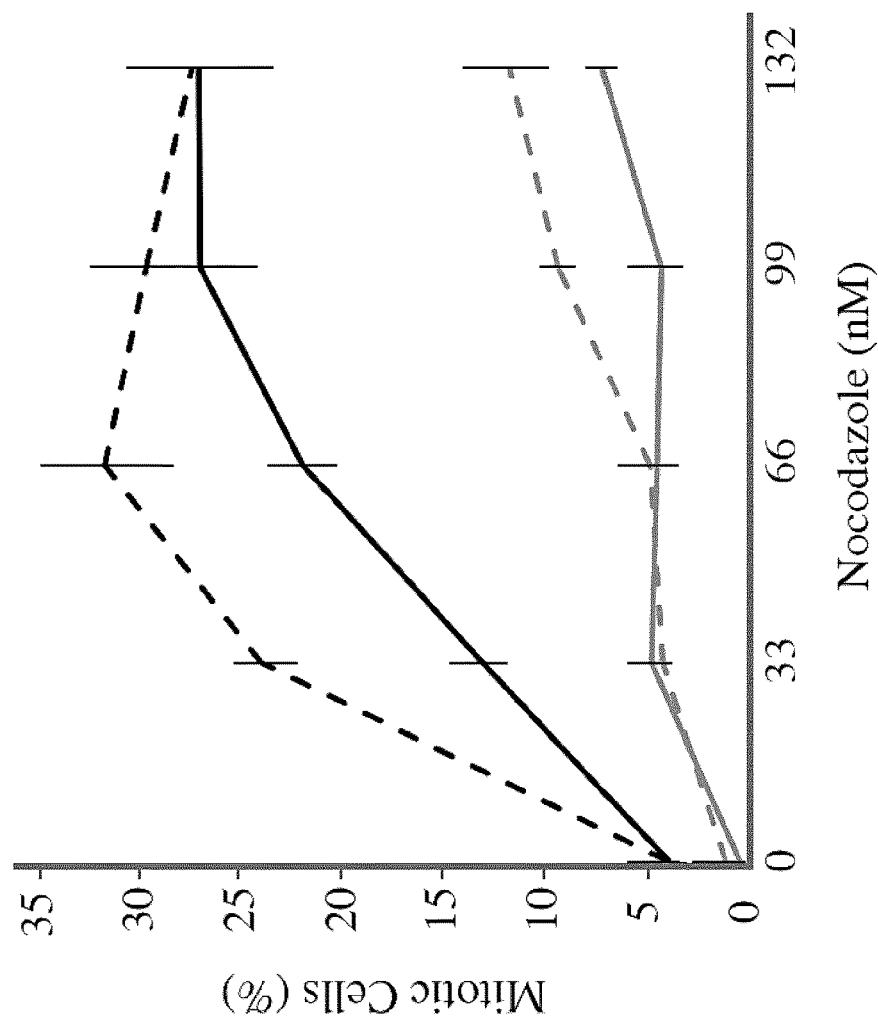
Figure 3:
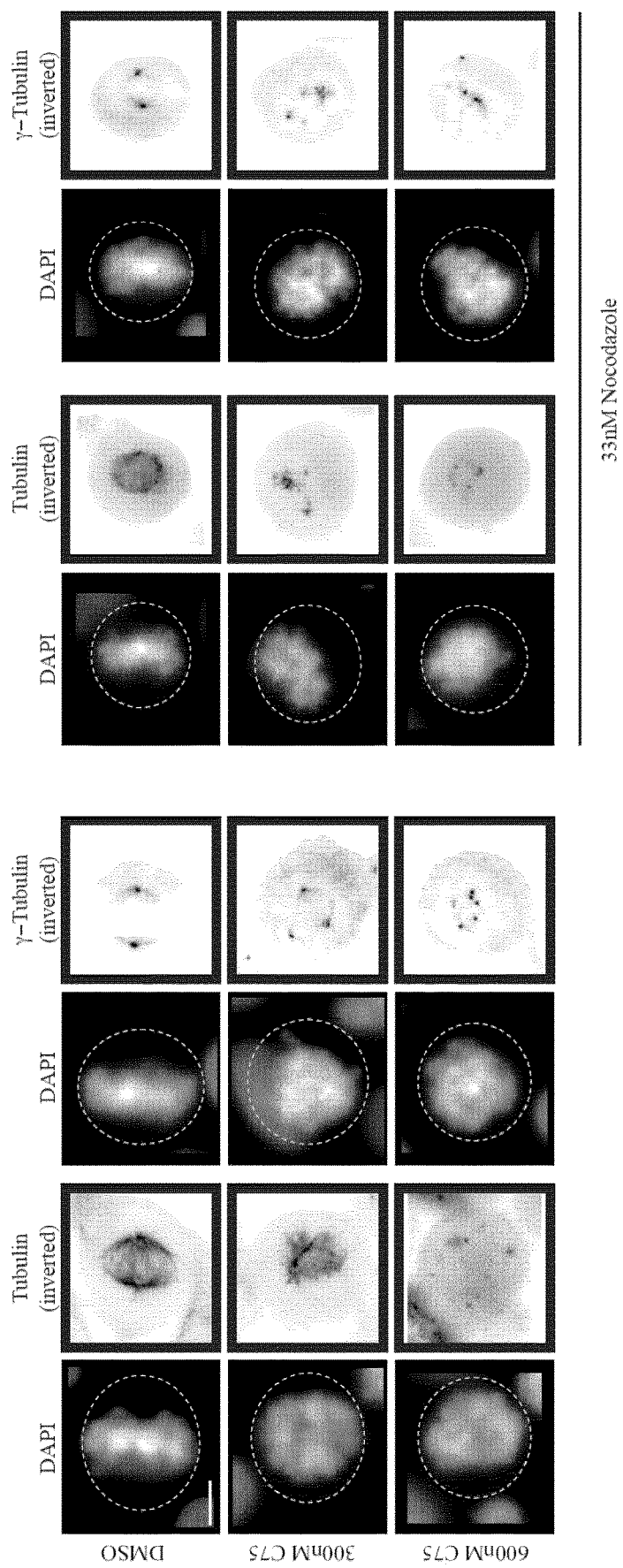
Figure 3:
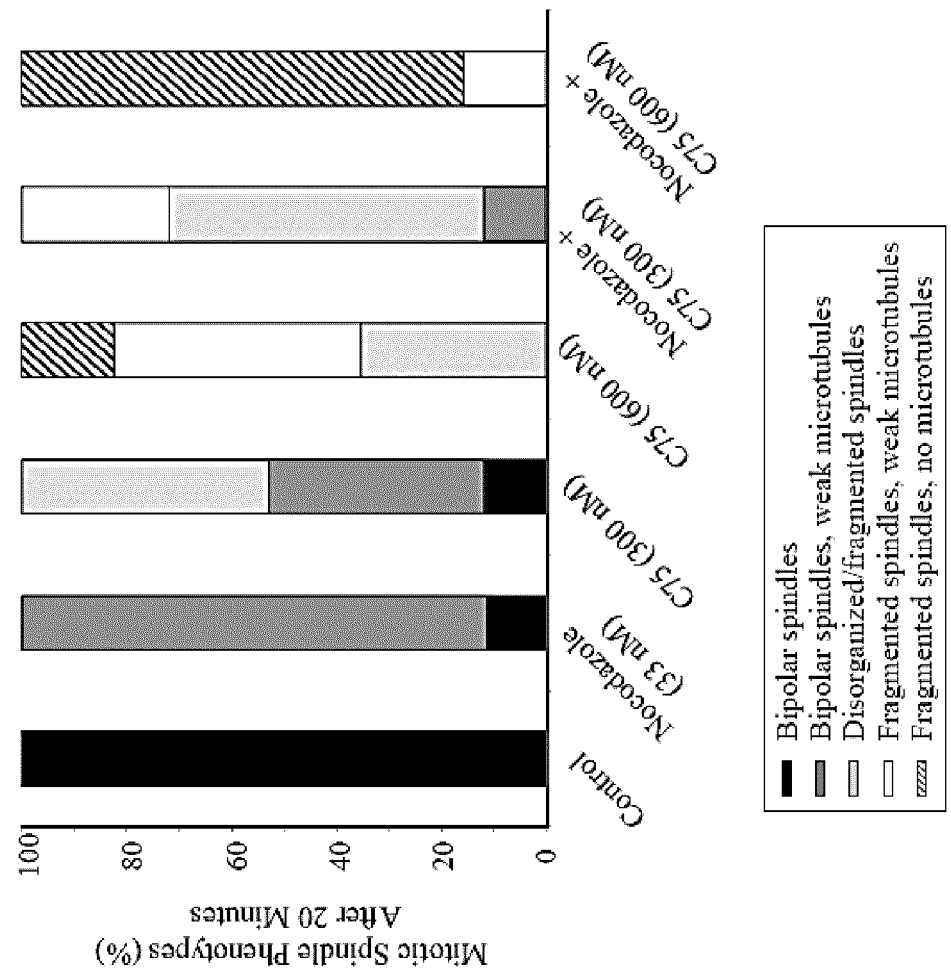

Typically, α-tubulin forms a dimer with β-tubulin that then assembles into the polymers that make microtubules[30]. At low concentrations, these drugs stabilize microtubules without changing their polymer mass, effectively 'freezing' the mitotic spindle. C75 does not appear to do this and enhances the selectivity of paclitaxel and nocodazole in HeLa cells vs. HFF1 cells (e.g. FIG. 3A, E). In addition, it was found that C75 offers a protective effect to non-cancerous HFF1 cells treated with paclitaxel (FIG. 3A). C75 enhances the phenotypes caused by paclitaxel in HCT116 cells (FIG. 3B-D). The proportion of mitotic spindle phenotypes is thresholded with 2.5 nM paclitaxel, and despite this, adding increased amounts of C75 worsens the phenotypes, suggesting that C75 has a unique molecular target vs. paclitaxel (FIG. 3B). Also, there was a significant decrease in fragment distance with increased paclitaxel concentration, but a significant increase in fragment distance when paclitaxel was combined with C75 (FIGS. 3C and 3D).

An in-depth analysis of HeLa cells treated with both C75 and nocodazole revealed that they have more extreme phenotypes when treated together vs. on their own (FIG. 3E-F). For instance, HeLa cells treated with nocodazole alone exhibit bipolar spindles with weak microtubules and HeLa cells treated with C75 alone have disorganized and/or fragmented mitotic spindles, whereas cells treated with both drugs exhibit increased fragmentation and loss of microtubules (FIG. 3G). Therefore, these thienoisoquinoline compounds such as C75 may have the potential for use in combinatorial therapies.

In addition, the thienoisoquinoline compounds disclosed herein may have the potential for use in combinatorial therapies with non-mitotic anti-cancer drugs (non-tubulin-targeting drugs) such as doxorubicin, an anthracycline, an alkylating drug, or an antimetabolite. Specifically, by not targeting tubulin, but still disrupting mitosis, the thienoisoquinoline compounds may be used as an anti-mitotic agent in cells that are resistant to tubulin-targeting drugs such as taxanes (e.g. due to the upregulation of alternate beta-tubulin isoforms). To evaluate this, cancer cell lines resistant to tubulin-targeting drugs or having higher resistance to tubulin-targeting drugs may be treated with a thienoisoquinoline compound in combination with a non-mitotic anti-cancer drug, for example Doxorubicin. Efficacy, for example in terms of mitotic arrest, may be evaluated using the methods described in Example 2.

Example 4

The anti-mitotic activity of a thienoisoquinoline compound can be evaluated in vivo using subcutaneous xenografts in rodents. Human cancer cells, e.g. obtained from patients and/or from cancer cell lines, are injected into each of the lower legs (one as a control) of nude rats or SCID mice. Other types of grafting in animal models to test the compounds, e.g. colorectal cancers with different metastases, are also contemplated. Different regiments of treatment will be tested by injection before tumors form, or after ~2 weeks when tumors are palpable (e.g. 50 mm$^3$). The treatment may also be administered orally, in particular to test for safety and bioavailability. The rodents are treated daily, after every 2-3 days, or weekly with an effective amount of a thienoisoquinoline compound or saline (control) under suitable conditions for a determined duration. Tumors will be monitored daily for change in growth (% treated vs. control). At the end of the study, tumors will be collected and fixed for more in depth analyses of tumor morphology. Toxicity will be monitored by weight loss and/or death[31-33].

Example 5

The anti-mitotic effect as well as synergistic and protective effects of a thienoisoquinoline compound in combination with an anti-cancer agent such as for example a taxane compound or vinca alkaloid, can also be assessed in vivo using similar methods as described in Example 4.

Example 6

Figure 4:
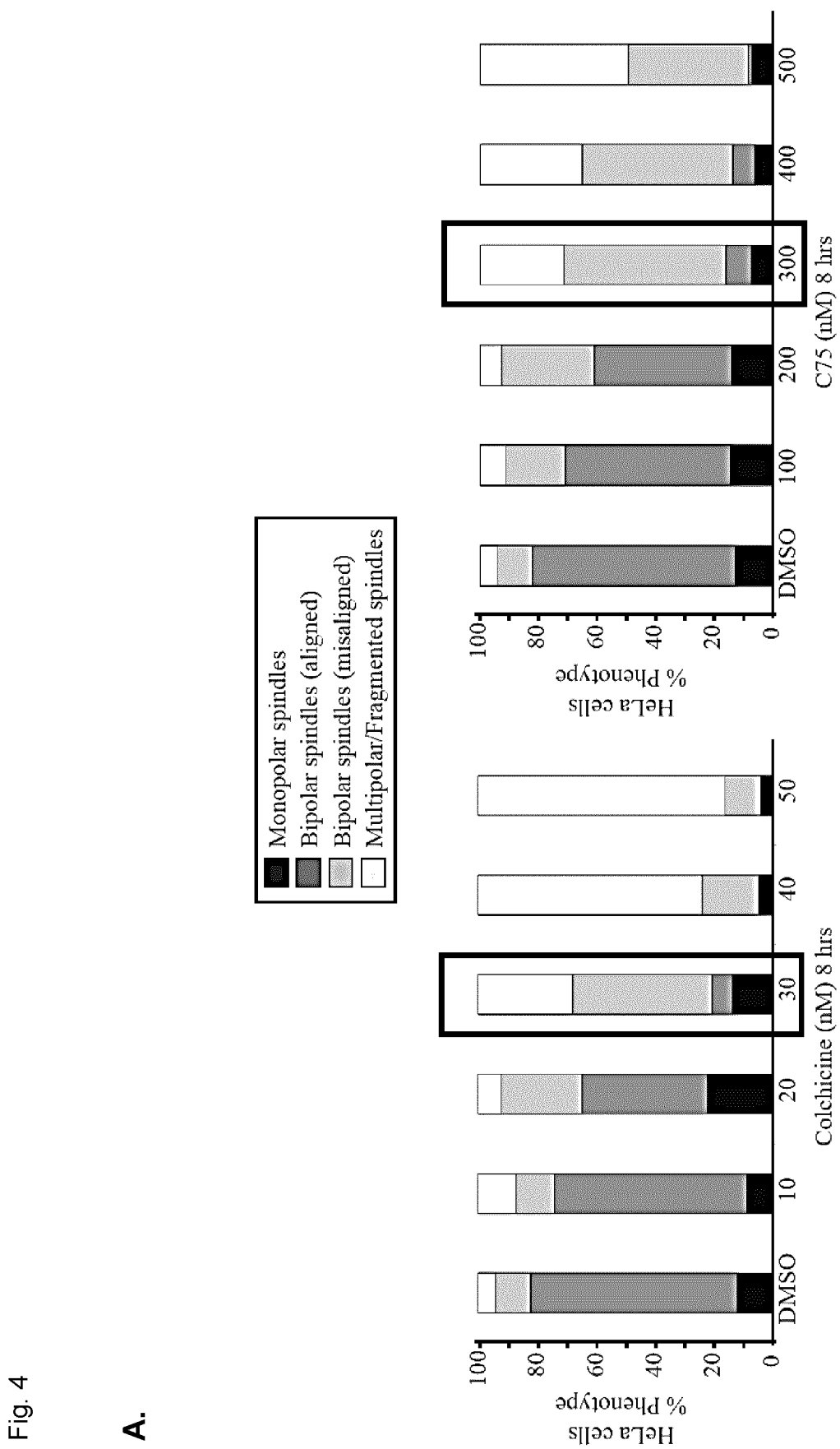
FIG. 4A is a series of bar graphs showing the proportion of HeLa cells that have monopolar spindles, bipolar spindles with aligned chromosomes, bipolar spindles with misaligned chromosomes and multipolar/fragmented spindles after treatments as shown with DMSO (control) and varying concentrations of colchicine or C75 after 8 hours.
FIG. 4B is a series of images of fixed HeLa cells stained for tubulin (microtubules) and DAPI (DNA) to show the different phenotypes that were observed after treatment with DMSO, colchicine or C75, respectively. Spindle fragmentation only occurred after extensive microtubule depolymerization in colchicine-treated cells, while the spindle poles fragmented prior to changes in microtubules after C75 treatment. The scale bar for all cells is 10 µm.
Figure 4:
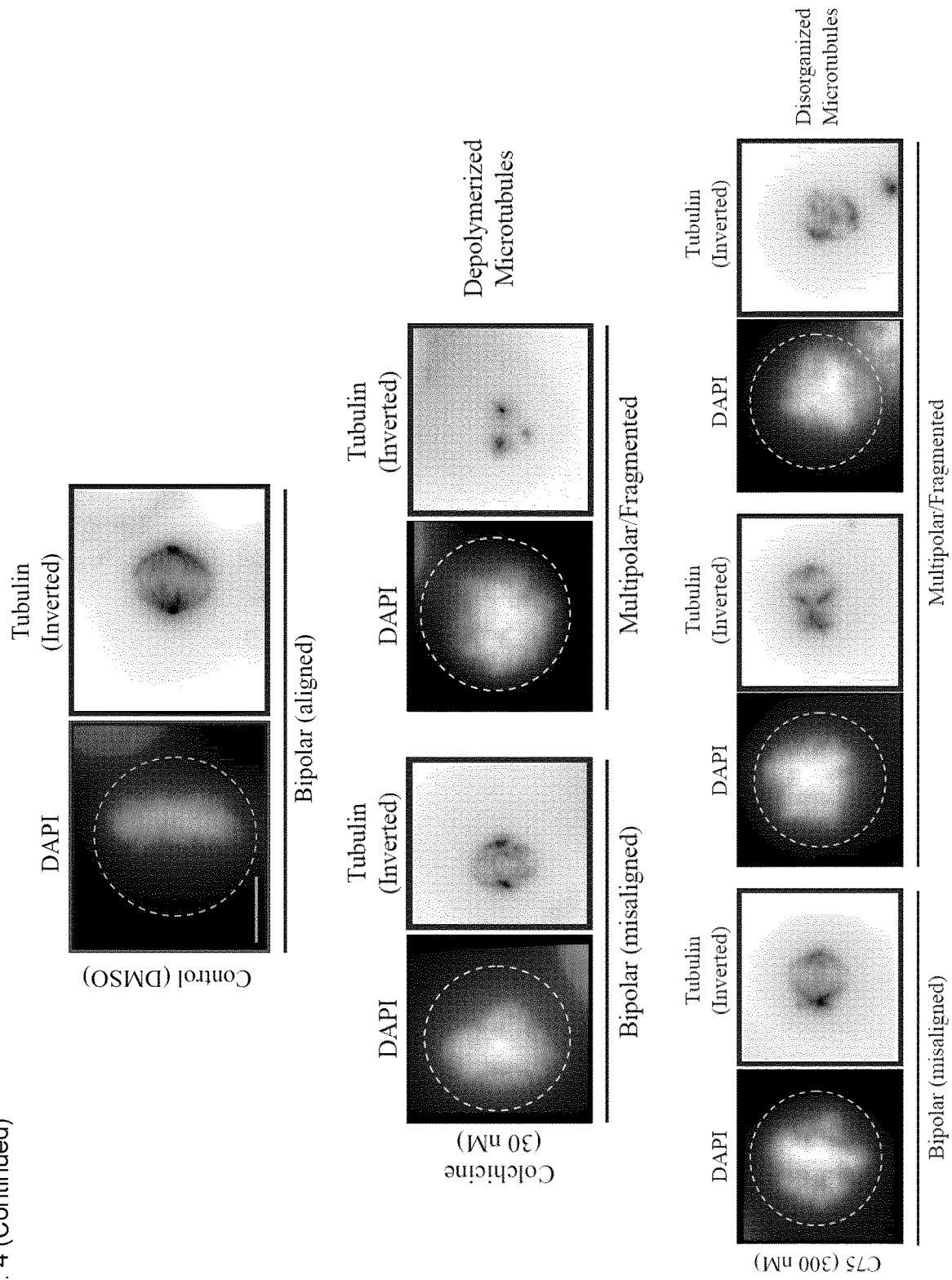

To show that C75 has a different effect on the mitotic spindle compared to microtubule depolymerizing agents, the spindle phenotypes were compared in HeLa cells after treatment with C75 or colchicine, which targets tubulin and induces microtubule depolymerization. As shown in FIGS. 4A and 4B, at lower concentrations of each drug (30 nM colchicine or 300 nM C75), cells treated with colchicine had bipolar spindles with less robust microtubules, while C75-treated cells had disrupted spindle poles. Cells treated with higher concentrations of colchicine (40 or 50 nM) had fragmented spindles, but only after extensive loss of microtubules, whereas C75 (400 or 500 nM) caused spindle fragmentation prior to extensive loss of microtubules.

Example 7—Testing in Tumour Spheroids

Figure 5A:
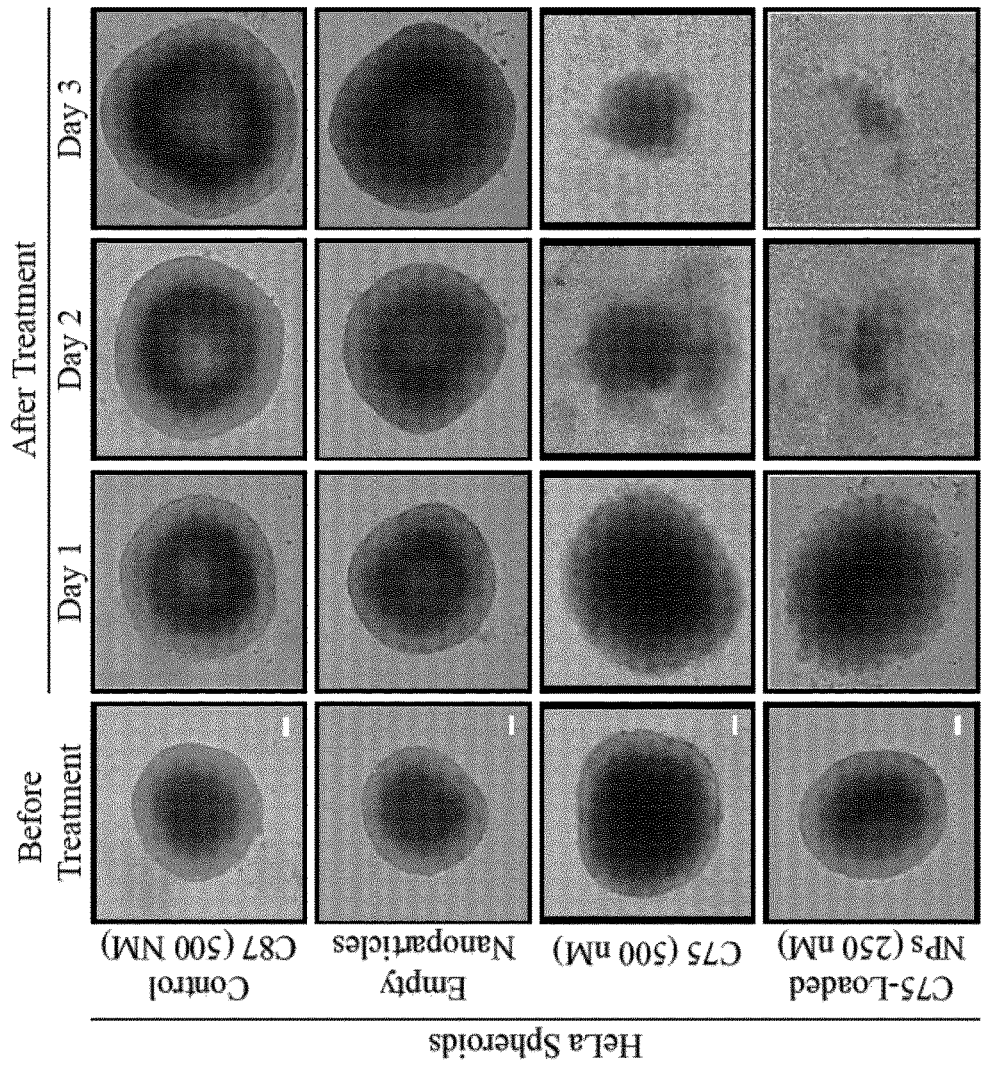
FIG. 5A) is a series of images of HeLa multicellular tumor spheroids (spheroids) treated with control (500 nM C87), empty nanoparticles, 500 nM C75 and 250 nM C75-loaded nanoparticles over 3 days. As can be seen, C75 disrupted HeLa spheroids after only 2 days, while the control spheroids continued to grow. The scale bar for all images is 100 µm.
Figure 5:
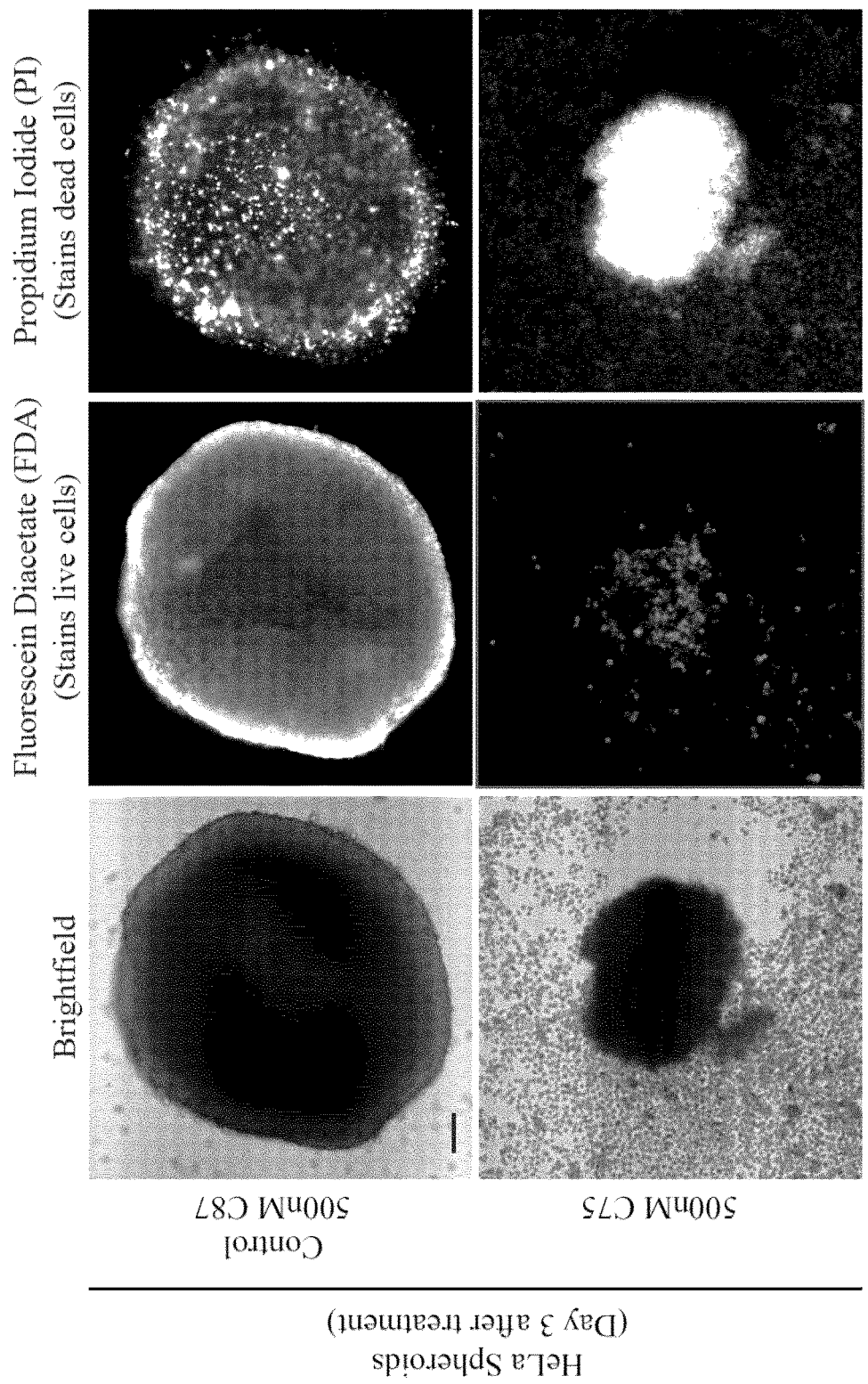
FIG. 5B) is a series images of HeLa spheroids after three days of treatment with control (500 nM C87) or 500 nM C75. The spheroids were stained for fluorescein diacetate (to detect live cells) and propidium iodide (to detect dead cells). The majority of HeLa cells were dead after C75 treatment. The scale bar for all images is 100 µm.
FIG. 5C) is a series of images of HCT116 spheroids treated with control (1 µM C87), 500 nM C75, 1 µM C75 and 500 nM C75-loaded nanoparticles over 5 days. As can be seen, C75 regressed the growth of HCT116 spheroids compared to control spheroids, which continued to grow. The borders of the spheroids treated with 1 µM C75 or with 500 nM C75-loaded nanoparticles became highly irregular, indicative of loss of spheroid integrity.
FIG. 5D) is a series images of HCT116 spheroids after six days of treatment with control (1 µM C87) or 1 µM C75. The spheroids were stained for fluorescein diacetate (live cells) and propidium iodide (dead cells). The HCT116 spheroids were much smaller after C75-treatment, but still contained live cells.
FIG. 5E) is a line graph showing the growth in surface area (%) of HCT116 spheroids treated with control (1 µM C87), 500 nM C75 and 1 µM C75 after six days.
FIG. 5F) is a series of images of A549 spheroids treated with control (750 nM C87), 500 nM C75, 1 µM C75 and 500 nM C75-loaded nanoparticles over 5 days. As can be seen, C75 regressed the growth of A549 spheroids. While C75-loaded nanoparticles did not appear to regress growth per se, the borders of the spheroids became highly irregular supporting their disruption. The scale bar for all images is 100 µm.
FIG. 5G) is a series of images of A549 spheroids after six days of treatment with control (750 nM C87) or 1 µM C75. The spheroids were stained for fluorescein diacetate (live cells) and propidium iodide (dead cells). As can be seen, C75 regressed the growth of the A549 spheroid and there were fewer live cells within the C75-treated spheroid in comparison to control.
Figure 5:
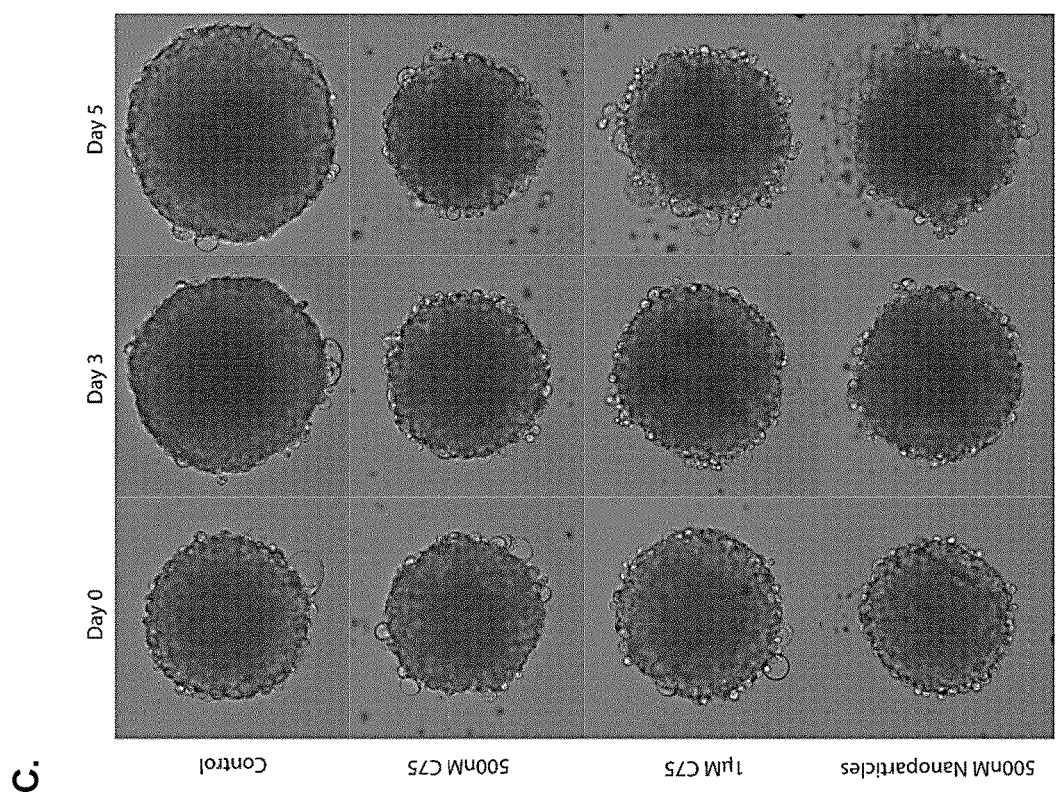
Figure 5:
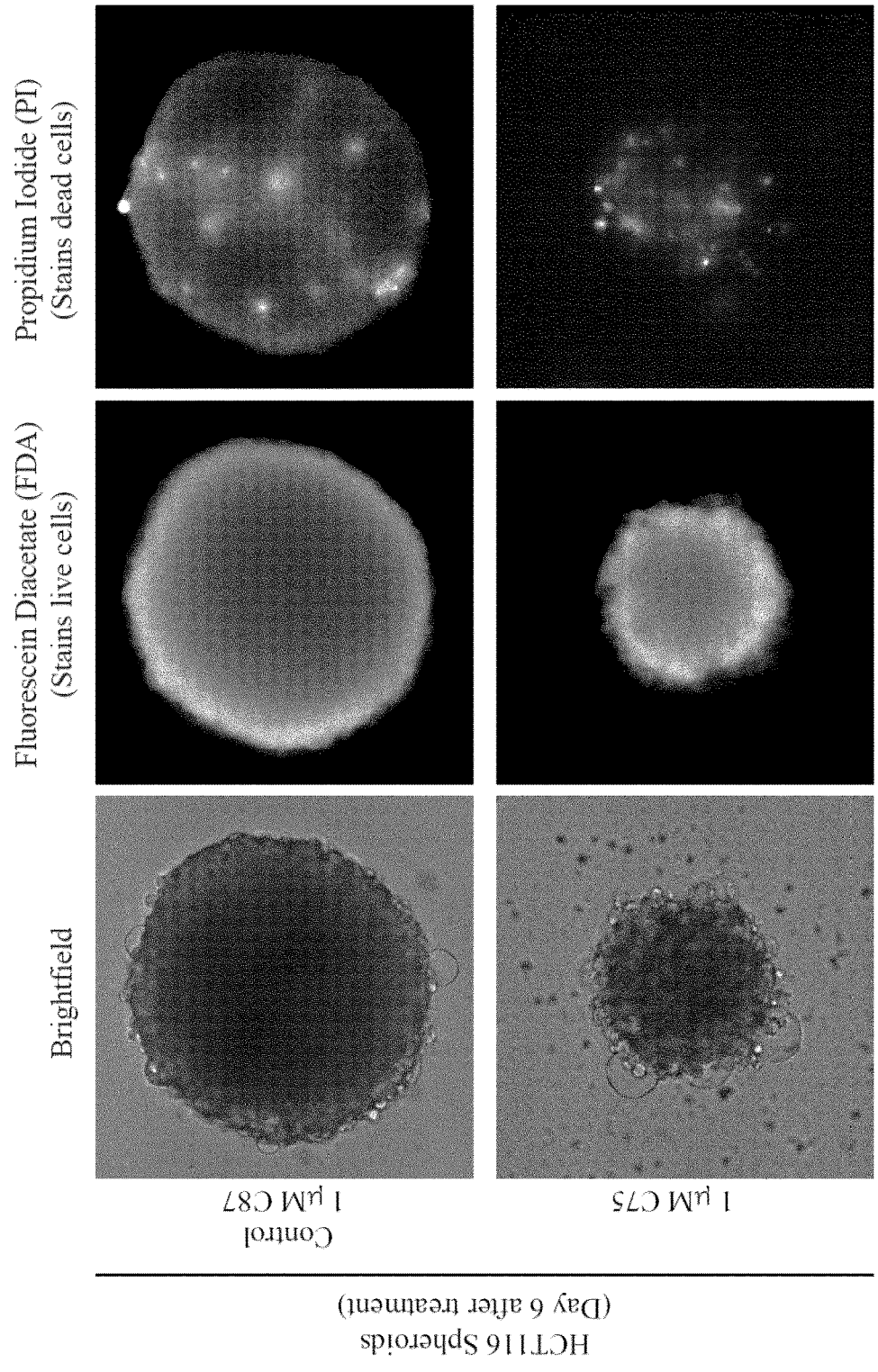
Figure 5:
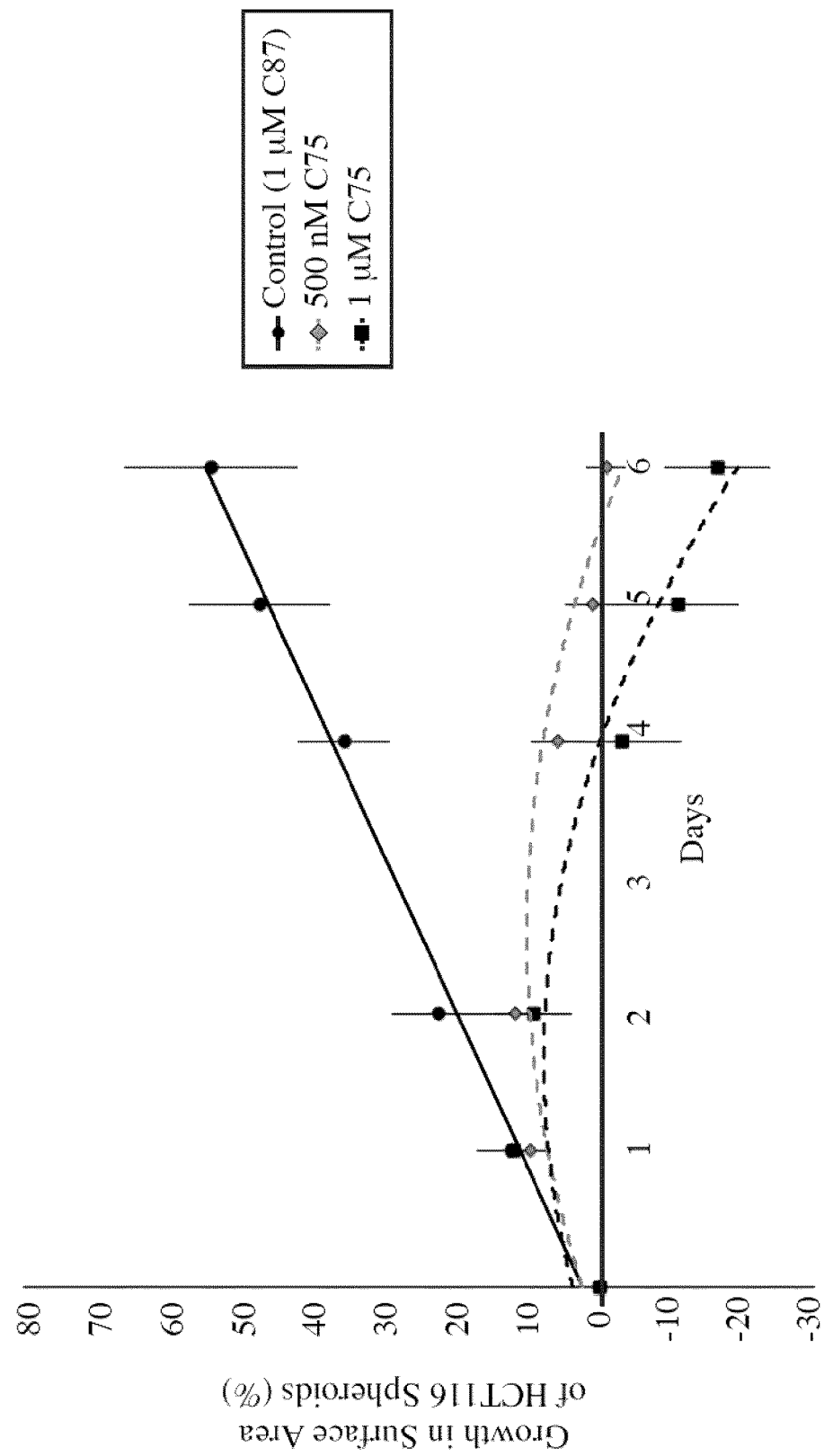
Figure 5:
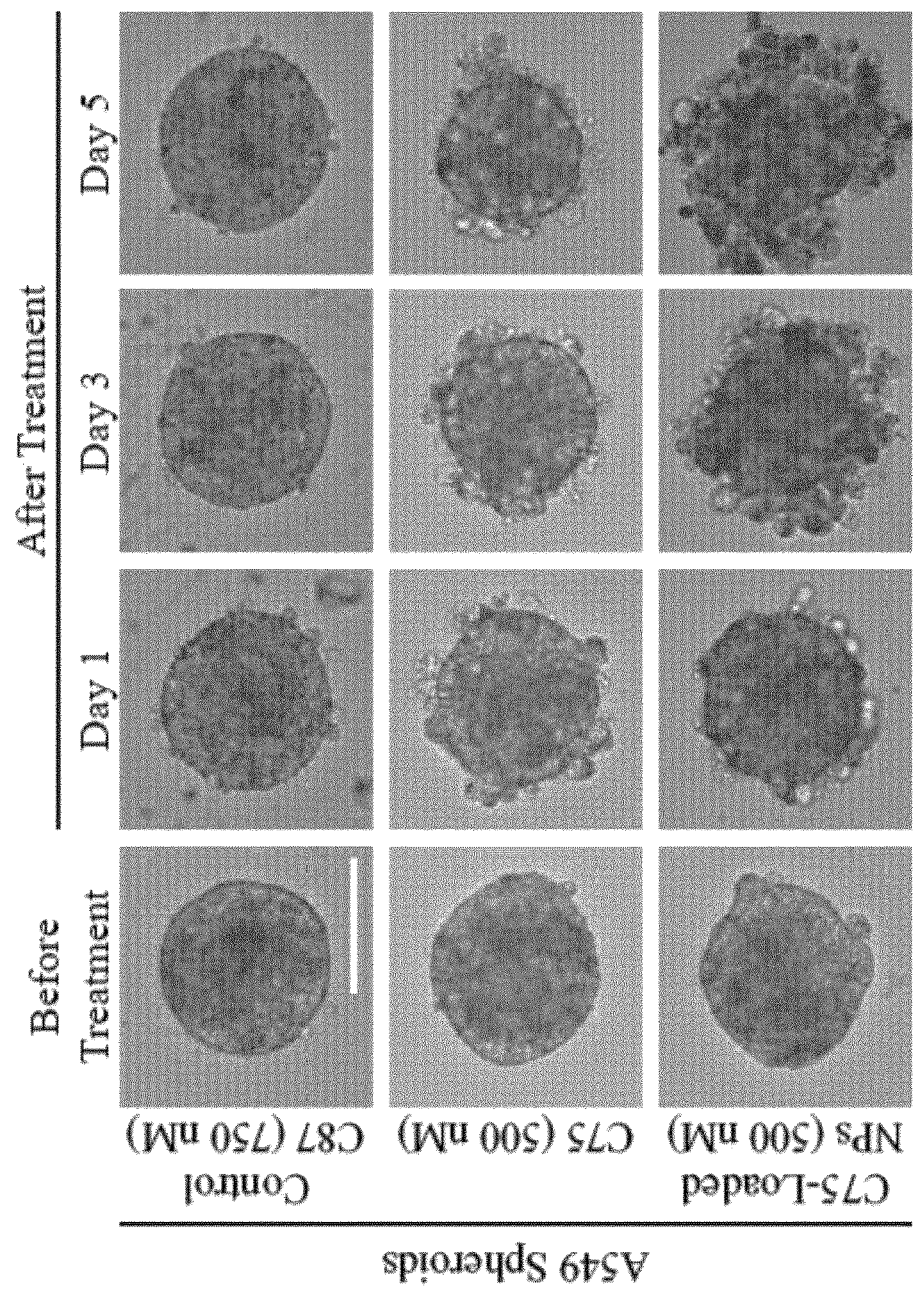
Figure 5:
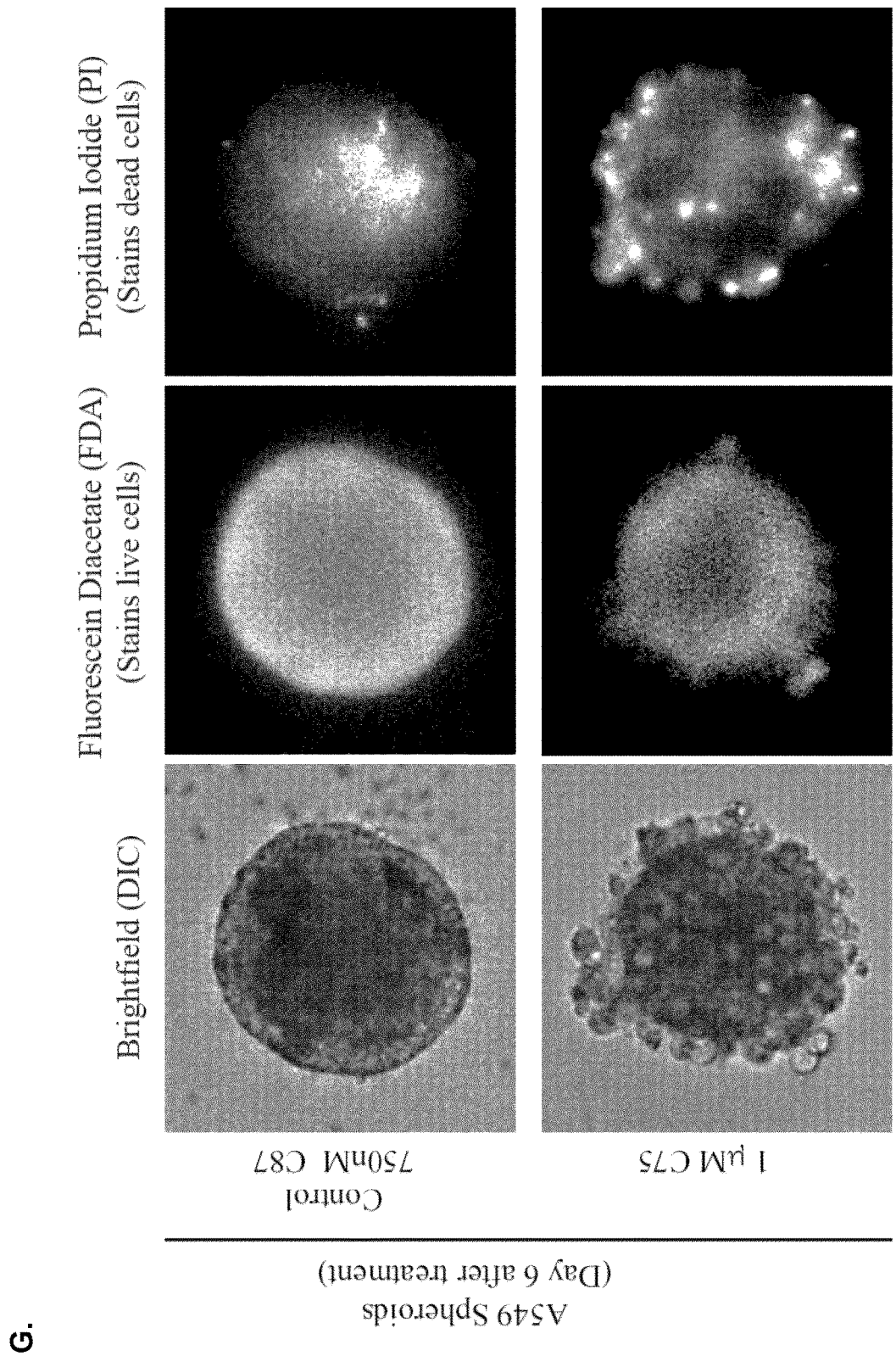

C75 was further tested in multicellular tumour spheroids, which are more representative of in vivo tumours. These spheroids were produced according to the methods of Friedrich et al. 2009[34]. Briefly, 96-well plates coated with 1.5% agarose were seeded with 500-1000 HeLa or HCT116 cells as outlined for the liquid-overlay technique. They were left to aggregate with gravity in optimal growth conditions, and individual spheroids were transferred to 24-well dishes for further growth and treatment. A549 spheroids were initiated using the hanging-drop method outlined by Froehlich et al. 2016[35], and transferred to 24-well dishes for further growth and treatment. HeLa, HCT116 and A549 spheroids were treated with C75 alone, or C75-loaded into polymeric nanoparticles. Nanoparticles can be produced for example according to the methods reviewed in Zhang et al. 2012[36]. Both C75 alone and C75-loaded nanoparticles were shown to disrupt HeLa spheroids (FIGS. 5A and 5B), and regress the growth of HCT116 spheroids (FIGS. 5C, 5D and 5E) and A549 spheroids (FIGS. 5F and 5G).

Example 8—New Synthetic Route

Another novel synthesis for thienoisoquinoline scaffold derivatives was designed.

C-75 Derivative Synthesis Experimental

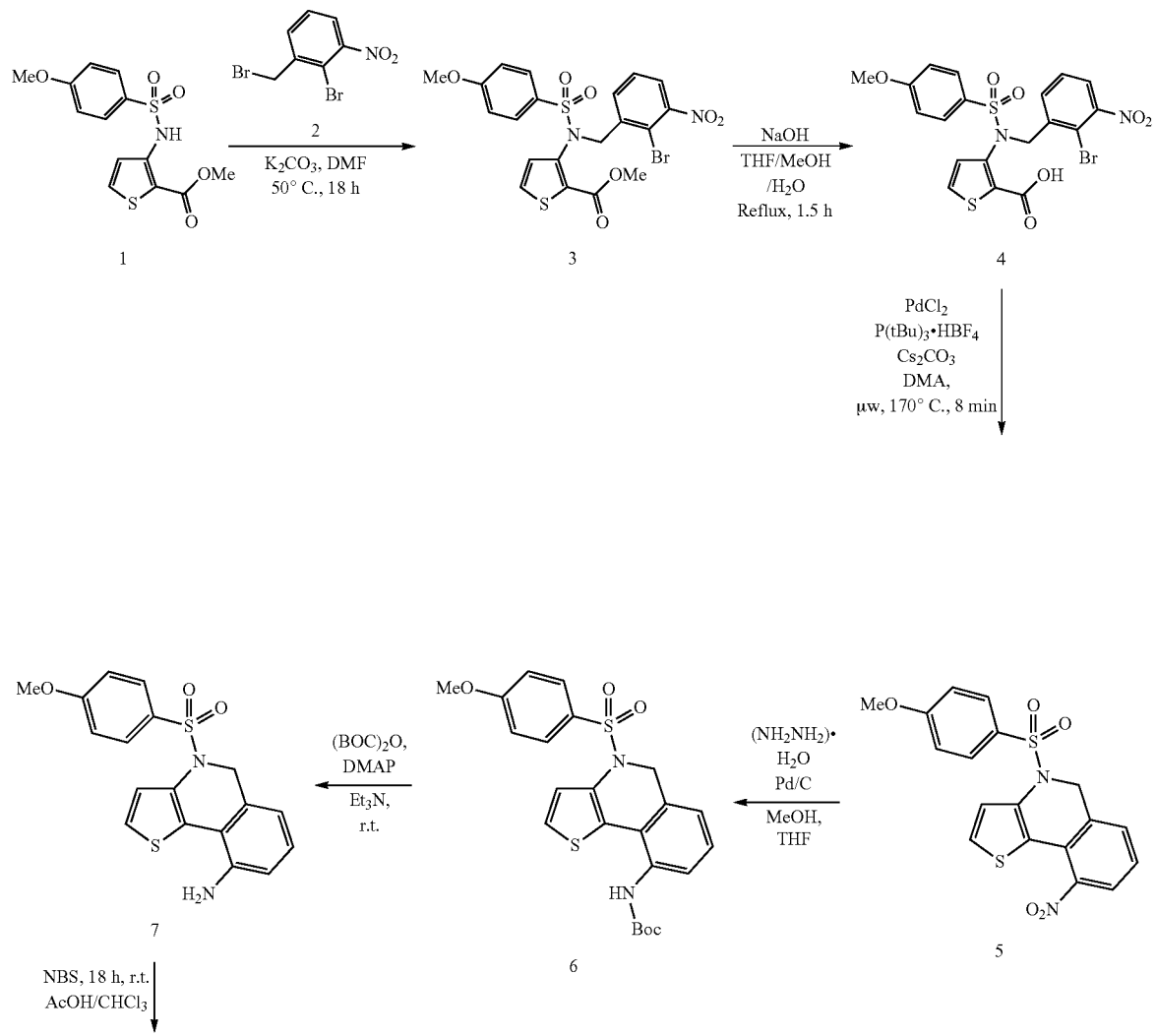

Scheme 1. Synthetic pathway of C75 meta amine handle

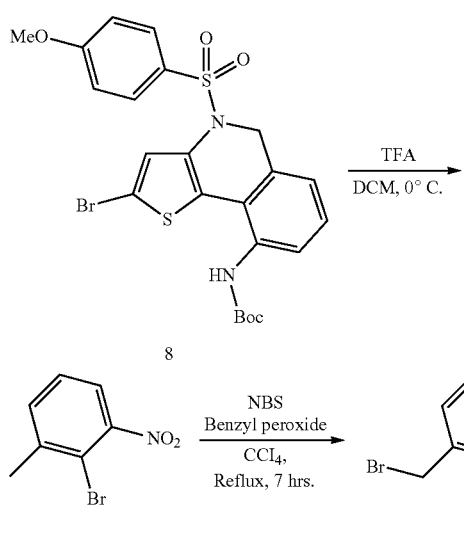
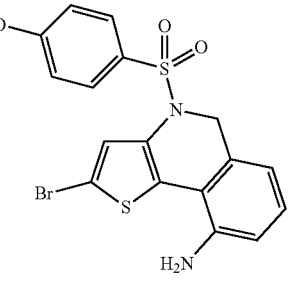

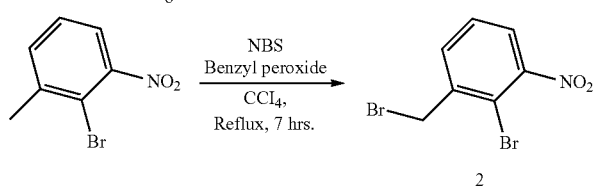

General Procedure for Bromination of Nitrotoluene 2-bromo-1-methyl-3-nitrobenzene (1 equiv.) and NBS (1.1 equiv) are mixed in 0.8M of anhydrous CCl$_4$ in an oven-dried vessel. The mixture is purged with Argon gas, and heated under reflux for 7 hours. The mixture is cooled to room temperature and diluted with DCM, then follow by washing with distilled water. The Aqueous layer is extract with DCM. The combined organic layers are washed three times with distilled water, and dried over Na$_2$SO$_4$. The compound is purified with column chromatography. The product is white solid. Isolated yield 72%.

Reaction mixture is cooled to room temperature after 18 hours. The mixture is diluted with EtOAc and washed with distilled water, and aqueous layer is extracted with EtOAc. The combined organic layers are washed with distill water three times, saturated salt solution three times, and dried over Na$_2$SO$_4$ The solvent is evaporated under reduced pressure, and solid residue is recrystallized with EtOAc and hexane. The final product is pale yellow crystal. Isolated yield: 92%

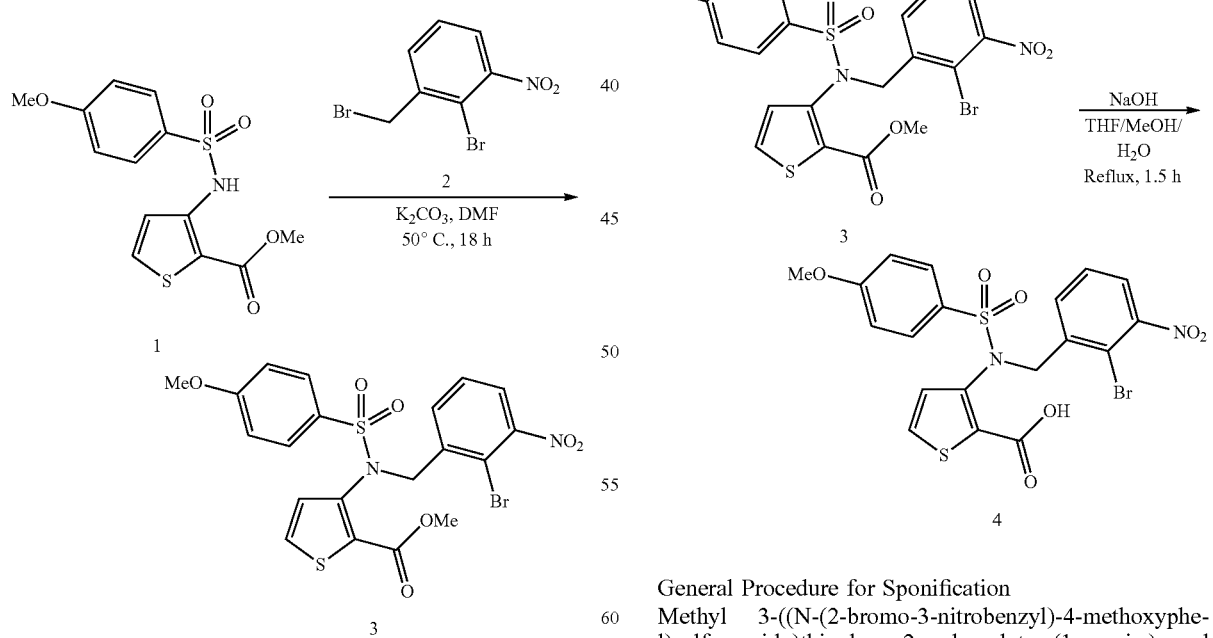

General Procedure for Benzylation

Methyl 3-((4-methoxyphenyl)sulfonamido)thiophene-2-carboxylate (1 equiv.), 2-bromo-1-(bromomethyl)-3-nitrobenzene (1.2 equiv.), and K$_2$CO$_3$ (3 equiv.) are mixed in 0.3M of DMF. Solution is heated to 50° C. for 18 hours.

General Procedure for Sponification

Methyl 3-((N-(2-bromo-3-nitrobenzyl)-4-methoxyphenyl)sulfonamido)thiophene-2-carboxylate (1 equiv.) and NaOH powder (5 equiv.) was mixed and dissolved with THF, water, and MeOH (2:1:1 respectively, 0.1M overall). The mixture is heated under reflux, then cooled to room temperature after 1.5 hours for completion, TLC is used to monitor the reaction. The mixture is treated with 1M HCl solution until pH reaches 1. The mixture is diluted with distilled water and extracted with DCM two times. The combined organic layers are washed with water three time, saturated salt solution two times, and dried over Na₂SO₄. The solvent is evaporated under reduced pressure, and residue is recrystallized with EtOAc and hexane. The final product is yellow solid. Isolated yield: 95%

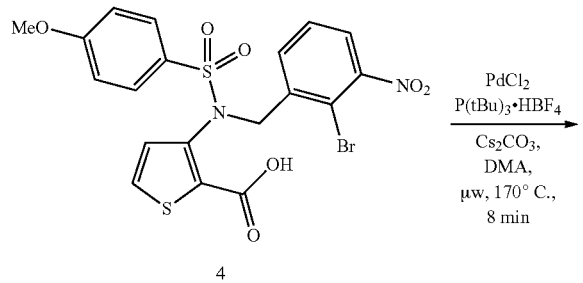

4

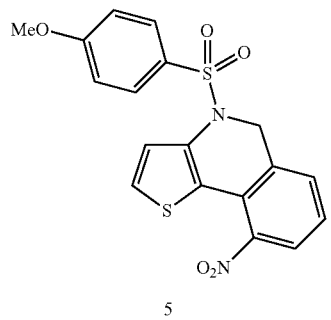

5

General Procedure for Decarboxylative Cross-Coupling 3-((N-(2-bromo-3-nitrobenzyl)-4-methoxyphenyl)sulfonamido)thiophene-2-carboxylic acid (1 equiv.) in DMA (0.1M) was added to an oven-dried microwave vial contain PdCl₂ (0.1 equiv.), P(tBu)₃.HBF₄ (0.2 equiv.), Cs₂CO₃ (3 equiv.). The mixture is heated under microwave radiation at 170° C. for 8 min, then cooled to room temperature, and diluted with EtOAc. The mixture is washed with distilled water, and aqueous layer is extracted with EtOAc. The combined layers are washed with saturated NaHCO₃, distilled water, saturated NaCl solution, and dried over Na₂SO₄. The solvent is evaporated under reduced pressure. The product is purified by column chromatography and recrystallization from CHCl₃ and MeOH. The final product is yellow crystal. Isolated yield: 41%.

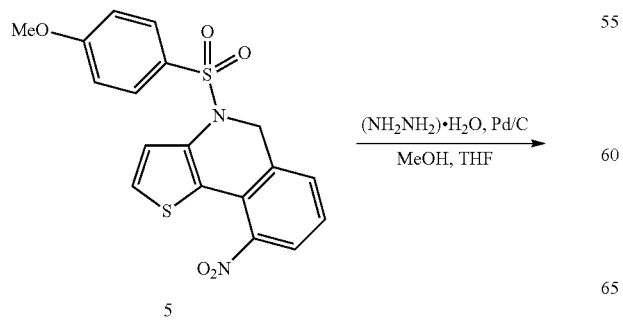

5

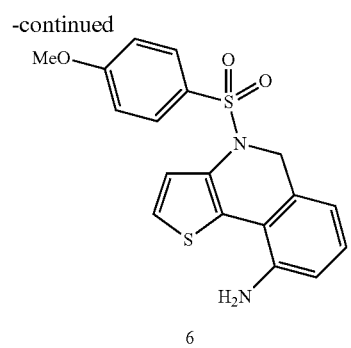

6

General Procedure for Reduction 4-((4-methoxyphenyl)sulfonyl)-9-nitro-4,5-dihydrothieno[3,2-c]isoquinoline (1 equiv.) and Pd/C (0.1 equiv. 10 mol %) is mixed with THF and MeOH (1:1 ratio, 0.2M overall). Hydrazine hydrate (10 equiv.) is added slowly to the mixture. The mixture is heated under reflux for 20 mins for completion. TLC is used to monitor the reaction. Mixture is filtered from a pad of celite and washed with EtOAc. The mixture is washed with distilled water, and aqueous layer is extracted with EtOAc, The combined organic layer is washed with distilled water one time, saturated salt solution one time, and dried over Na₂SO₄. The solvent is evaporated under reduced pressure. The residue is recrystallized with CHCl₃ and MeOH. Isolated yield: 70%.

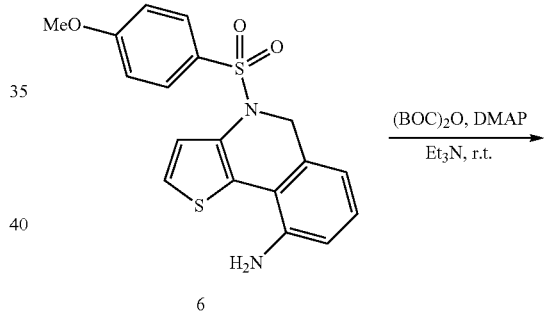

General Procedure for Amine Protection 4-((4-methoxyphenyl)sulfonyl)-4,5-dihydrothieno[3,2-c]isoquinolin-9-amine (1 equiv.) and Di-tert-butyl dicarbonate (2 equiv.) are dissolved in Et₃N (0.4 M), DMAP (1 equiv.) is added into mixture. The mixture is placed under room temperature for 48 hours. The mixture is diluted with EtOAc and washed with distilled water. The aqueous layer is extracted with EtOAc. The combined organic layers are washed with 1M HCl one time, distilled water three times, saturated salt solution one time, and dried over Na₂SO₄. The solvent is evaporated under reduced pressure. The product is purified by column chromatography. The product is colorless solid. Isolated yield: 60%

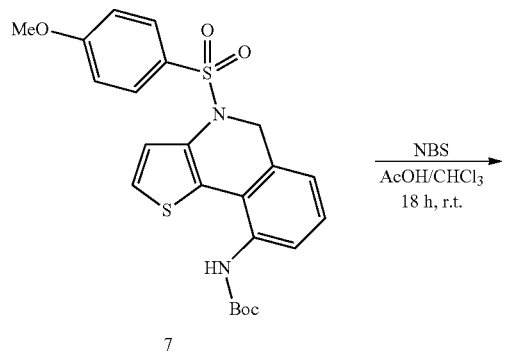

7

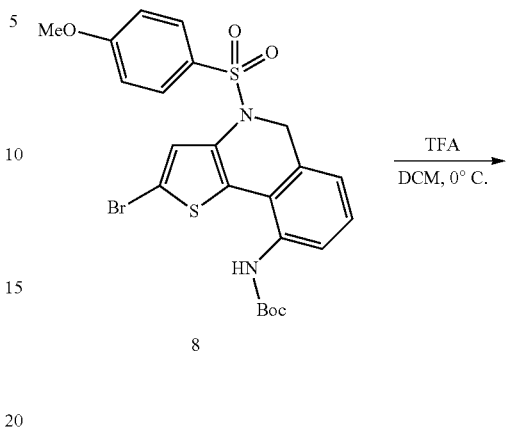

8

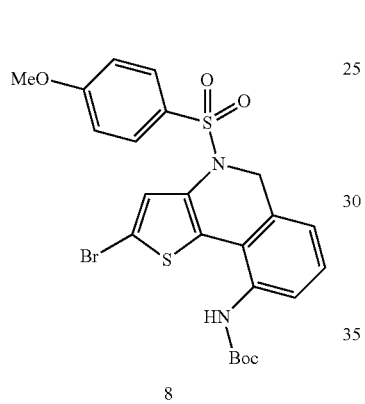

8

General Procedure for Bromination tert-butyl (4-((4-methoxyphenyl)sulfonyl)-4,5-dihydrothieno[3,2-c]isoquinolin-9-yl)carbamate (1 equiv.) and NBS (1.1 equiv.) are mixed with CHCl₃ (0.1M) in an ember vial, and mixture is placed in ice bath follow by 2 v/v % AcOH. The reaction is slowly return to room temperature and run for 18 hours. The mixture is diluted with EtOAc then washed with distilled water, and aqueous layer is extracted with EtOAc. The combined organic layer is washed with distilled water one time, saturated salt solution one time, and dried over Na₂SO₄. The solvent is evaporated under reduced pressure. The product is purified by column chromatography. The product is light brown solid. Isolated yield: 30%

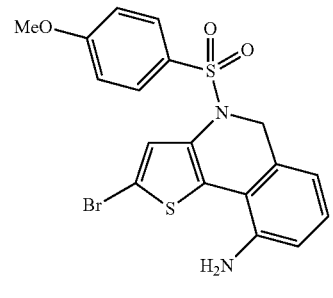

9

General Procedure for Boc Group Deprotection tert-butyl (2-bromo-4-((4-methoxyphenyl)sulfonyl)-4,5-dihydrothieno[3,2-c]isoquinolin-9-yl)carbamate (1 equiv.) is dissolved on DCM (0.1M) and placed in ice bath. 50 v/v % TFA is added slowly to mixture. The reaction is monitored by TLC, and stopped after 5 hours. The mixture is diluted with EtOAc then washed with distilled water, and aqueous layer is extracted with EtOAc. The combined organic layer is washed with saturated NaHCO₃ one time, distilled water one time, saturated NaCl solution one time, and dried over Na₂SO₄. The solvent is evaporated under reduced pressure. The product is purified by column chromatography. The product is brown solid. Isolated yield: 25% Scheme 2. Synthetic pathway of C75 B-Ring derivative

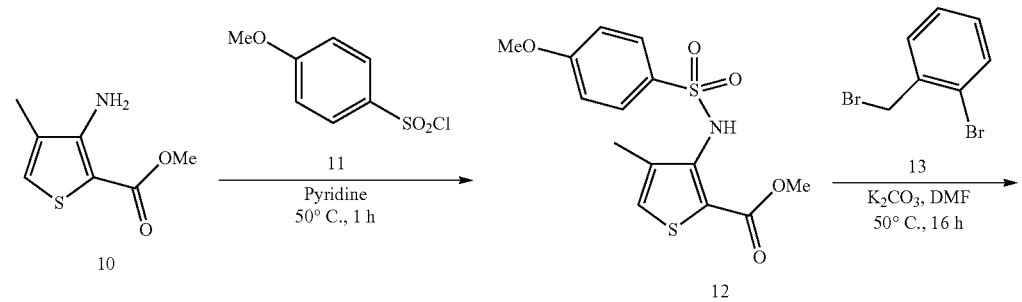

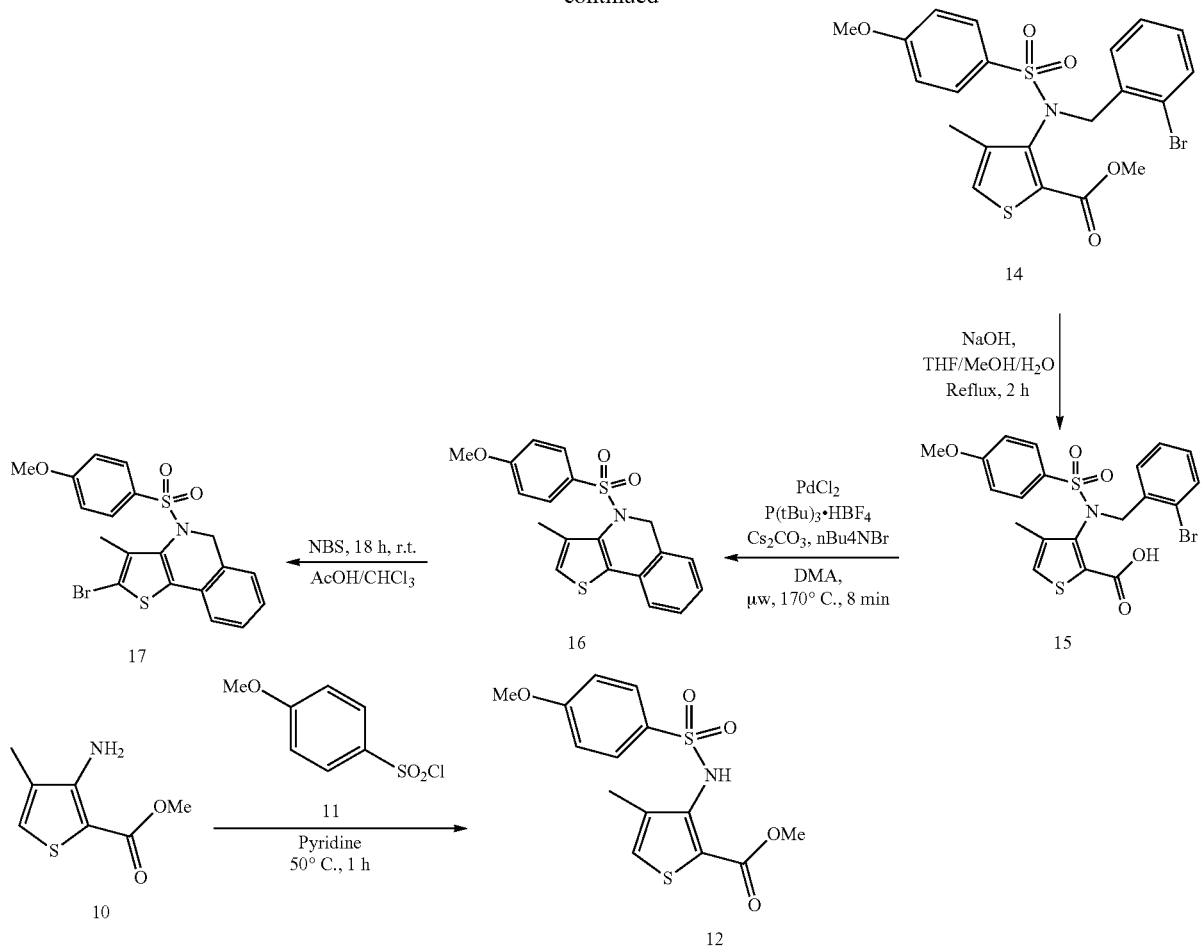

General Procedure for Sulfonylation

Methyl 3-amino-4-methylthiophene-2-carboxylate (1 equiv.) and 4-methoxybenzenesulfonyl chloride (1.5 equiv.) are mixed in 0.8M of Pyridine. Solution is heated to 50° C. for 1.5 hour, and is cooled to room temperature. The mixture is diluted with EtOAc and washed with distilled water, and aqueous layer is extracted with EtOAc. The combined organic layers are washed with distill water three times and Saturated salt solution three times. The solvent is evaporated under reduced pressure, and solid residue is recrystallized with EtOAc and hexane. Product is colorless crystal. Isolated yield: 74%

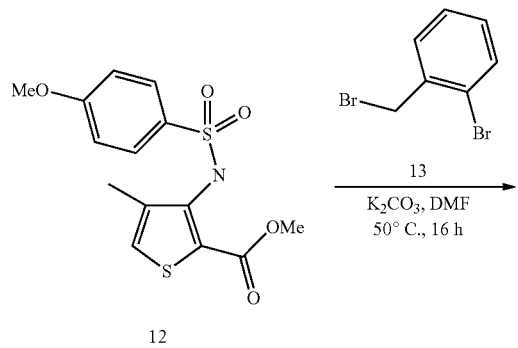

-continued

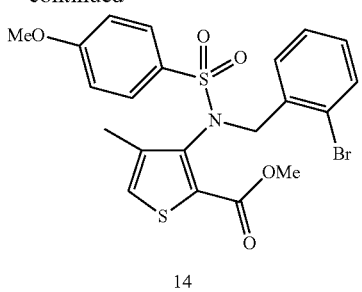

General Procedure for Benzylation methyl 3-((4-methoxyphenyl)sulfonamido)thiophene-2-carboxylate (1 equiv.), 1-bromo-2-(bromomethyl)benzene (1.2 equiv.), and $K_2CO_3$ (3 equiv.) are mixed in 0.3M of DMF. Solution is heated to 50° C. for 16 hours. Reaction mixture is cooled to room temperature after 18 hours. The mixture is diluted with EtOAc and washed with distilled water, and aqueous layer is extracted with EtOAc. The combined organic layers are washed with distill water three times, saturated salt solution three times, and dried over $Na_2SO_4$ The solvent is evaporated under reduced pressure, and solid residue is recrystallized with EtOAc and hexane. The final product is colorless crystal. Isolated yield: 73%

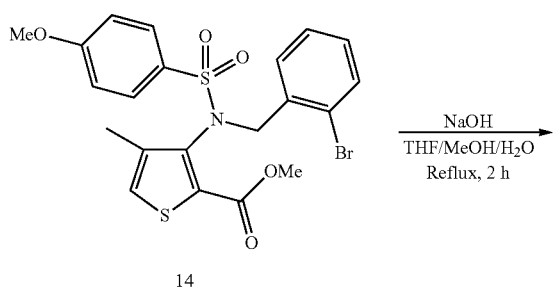

14

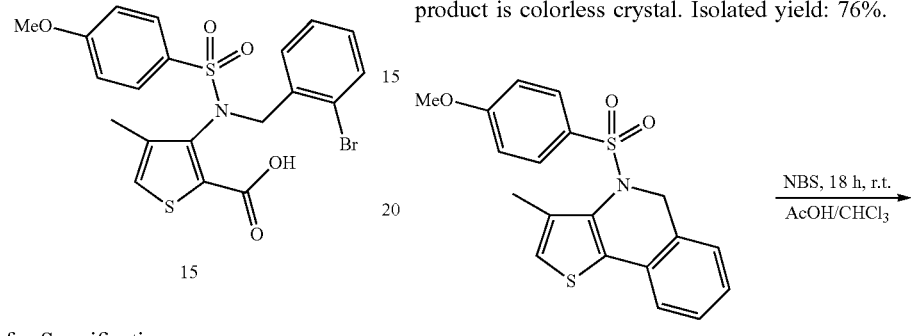

General Procedure for Sponification methyl 3-((N-(2-bromobenzyl)-4-methoxyphenyl)sulfonamido)-4-methylthiophene-2-carboxylate (1 equiv.) and NaOH powder (5 equiv.) was mixed and dissolved with THF, water, and MeOH (2:1:1 respectively, 0.1M overall). The mixture is heated under reflux, then cooled to room temperature after 2 hours for completion, TLC is used to monitor the reaction. The mixture is treated with 1M HCl solution until pH reaches 1. The mixture is diluted with distilled water and extracted with DCM two times. The combined organic layers are washed with water three time, saturated salt solution two times, and dried over $Na_2SO_4$. The solvent is evaporated under reduced pressure, and residue is recrystallized with EtOAc and hexane. The final product is colorless solid. Isolated yield: 84%

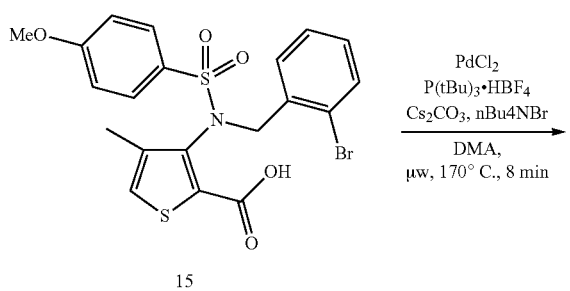

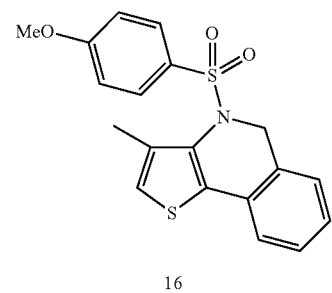

16

General Procedure for Decarboxylative Cross-Coupling 3-((N-(2-bromobenzyl)-4-methoxyphenyl)sulfonamido)-4-methylthiophene-2-carboxylic acid (1 equiv.) in DMA (0.1M) was added to an oven-dried microwave vial contain $PdCl_2$ (0.1 equiv.), $P(tBu)_3 \cdot HBF_4$ (0.2 equiv.), $nBu_4NBr$ (0.15 equiv.), and $Cs_2CO_3$ (3 equiv.). The mixture is heated under microwave radiation at 170° C. for 8 min, then cooled to room temperature, and diluted with EtOAc. The mixture is washed with distilled water, and aqueous layer is extracted with EtOAc. The combined layers are washed with saturated $NaHCO_3$, distilled water, saturated NaCl solution, and dried over $Na_2SO_4$. The solvent is evaporated under reduced pressure. The product is purified by column chromatography and recrystallization from $CHCl_3$ and MeOH. The final product is colorless crystal. Isolated yield: 76%.

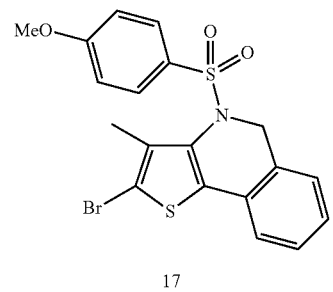

16

17

General Procedure for Bromination 4-((4-methoxyphenyl)sulfonyl)-3-methyl-4,5-dihydrothieno[3,2-c]isoquinoline (1 equiv.) and NBS (1.1 equiv.) are mixed with $CHCl_3$ (0.1M) in an ember vial, and mixture is placed in ice bath follow by 1 v/v % AcOH. The reaction is slowly return to room temperature and run for 18 hours. The mixture is diluted with EtOAc then washed with distilled water, and aqueous layer is extracted with EtOAc. The combined organic layer is washed with distilled water one time, saturated salt solution one time, and dried over $Na_2SO_4$. The solvent is evaporated under reduced pressure. The product is purified by column chromatography. The product is colorless solid. Isolated yield: 71%

The embodiments of paragraphs of the present disclosure are presented in such a manner in the present disclosure so as to demonstrate that every combinations of embodiments, when applicable can be made. These embodiments have thus been presented in the description in a manner equivalent to making dependent claims for all the embodiments that depend upon any of the preceding claims (covering the previously presented embodiments), thereby demonstrating that they can be combined together in all possible manners. For example, all the possible combination, when applicable, between the embodiments of paragraphs of the present disclosure and the processes of the SUMMARY OF THE DISCLOSURE are hereby covered by the present disclosure.

REFERENCES

1. Hay, M., Thomas D. W., Craighead J. L., Economides C., and Rosenthal, J. 2014. Clinical development success rates for investigational drugs. *Nature Biotech.* 32: 40-51.
2. Pearce, B. C., Sofia, M. J., Good, A. C., Drexler, D. M., and Stock, D. A. 2006. An empirical process for the design of high-throughput screening deck filters. *J. Chem. Inf. Model.* 46: 1060-1068.
3. Baell, J. B., and Holloway, G. A. 2010. New substructure filters for removal of pan assay interference compounds (PAINS) from screening libraries and for their exclusion in bioassays. *J. Med. Chem.* 53: 2719-2740.
4. Lagorce, D., Sperandio, O., Galons, H., Miteva, M. A., and Villoutreix, B. O. 2008. FAF-Drugs2: Free ADME/tox filtering tool to assist drug discovery and chemical biology projects. *BMC Bioinformatics* 9: 396.
5. Kazius, J., McGuire, R., and Bursi, R. 2005. Derivation and validation of toxicophores for mutagenicity prediction. *J. Med. Chem.* 48: 312-320.
6. Bruns, R. F., and Watson, I. A. 2012. Rules for identifying potentially reactive or promiscuous compounds. *J. Med. Chem.* 55: 9763-9772.
7. Mukherjee, S., and Pal., M. 2013. Quinolines: a new hope against inflammation. *Drug Discovery Today* 18: 389-398.
8. Mukherjee, S., and Pal., M. 2013. Medicinal chemistry of quinolines as emerging anti-inflammatory agents: an overview. *Curr Med Chem.* 20: 4386-4410.
9. Beccalli, E. M. Broggini, G. Martinelli, M., and Sottocornola, S. 2008. Microwave-assisted intramolecular cyclization of electron-rich heterocycle derivatives by a palladium-catalyzed coupling reaction. *Synthesis* 1: 136-140.
10. Wong, N. W. Y, and Forgione, P. 2012. A one-pot double C—H activation palladium-catalyzed route to a unique class of highly functionalized thienoisoquinolines *Org. Lett.* 14: 2738-2741.
11. Chen, F. Wong, N. W. Y., and Forgione, P. 2014. One-pot tandem palladium-catalyzed decarboxylative cross-coupling and C—H activation route to thienoisoquinolines. *Adv Synth Cat.* 365: 1725-1730.
12. Chan, K. S., Koh, C. G., and Li, H. Y. 2012. Mitosis-targeted anti-cancer therapies: where they stand. *Cell Death Dis.* 3: e411; doi:10.1038/cddis.2012.148.
13. Parker, A. L., Kavallaris, M., and McCarroll, J. A. 2014. Microtubules and their role in cellular stress in cancer. *Front. Oncol.* 4: 1-19.
14. Mogilner, A., and Craig, E. 2010. Towards a quantitative understanding of mitotic spindle assembly and mechanics. *J. Cell Science* 123: 3435-3445.
15. Sacristan, C., and Kops, G. J. 2015. Joined at the hip: kinetochores, microtubules, and spindle assembly checkpoint signaling. *Trends Cell Biol.* 25: 21-28.
16. Topham, C. H., and Taylor, S. S. 2013. Mitosis and apoptosis: how is the balance set? Curr. *Opin. Cell Biol.* 25: 780-785.
17. Burgess, A., Rasouli, M., and Rogers, S. 2014. *Stressing mitosis to death. Front. Oncol.* 4: 140. Doi: 10.3389/fonc.2014.00140.
18. Zasadil, L. M., Andersen, K. A., Yeum, D., Rocque, G. B., Wilke, L. G., Tevaarwerk, A. J., Raines, R. T., Burkard, M. E., and Weaver, B. A. 2014. Cytotoxicity of paclitaxel in breast cancer is due to chromosome missegregation on multipolar spindles. *Science Translational Medicine* 6:229ra43.
19. Hinchcliffe, E. H. 2014. Centrosomes and the art of mitotic spindle maintenance. *Int. Rev. Mol. Cell Mol. Biol.* 313: 179-217.
20. Gergely, F., and Basto, R. 2008. Multiple centrosomes: together they stand, divided they fall. *Genes Dev.* 22: 2291-2296.
21. Godinho, S. A., and Pellman, D. 2014. Causes and consequences of centrosome abnormalities in cancer. *Philos. Trans. R. Soc. Lond. B Biol. Sci.* 369: 20130467.
22. Ogden, A., Rida, P. C., and Aneja, R. 2012. Let's huddle to prevent a muddle: centrosome declustering as an attractive anticancer strategy. *Cell Death Differ.* 19: 1255-1267.
23. Chan, J. Y. 2011. A clinical overview of centrosome amplification in human cancers. *Int. J. Biol. Sci.* 7: 1122-1144.
24. Kawamura, E., Fielding, A. B., Kannan, N., Balgi, A., Eaves, C. J., Roberge, M., and Dedhar, S. 2013. Identification of novel small molecule inhibitors of centrosome clustering in cancer cells. *Oncotarget* 4: 1763-1776.
25. Eke, I., Leonhardt, F., Storch, K., Hehlgans, S., and Cordes, N. 2009. The small molecule inhibitor QLT0267 radiosensitizes squamous cell carcinoma cells of the head and neck. *PLoS One* 4: e6434.
26. Fielding, A. B., Lim, S., Montgomery, K., Dobreva, I., and Dedhar, S. 2011. A critical role of integrin-linked kinase, ch-TOG and TACC3 in centrosome clustering in cancer cells. *Oncogene* 30: 521-534.
27. Yang, B. et al. 2014. Discovery of potent KIFC1 inhibitors using a method of high-throughput synthesis and screening. *J. Med. Chem.* 57: 9958-9970.
28. Li, Y., Lu, W., Chen, D., Boohaker, R. J., Zhai, L., Padmalayam, I., Wennerberg, K., Xu, B., and Zhang, W. 2015. KIFC1 is a novel potential therapeutic target for breast cancer. *Cancer Biol. Ther.* 16: 1316-1322.
29. Zhang, W. et al. 2016. Discovery of a novel inhibitor of kinesin-like protein KIFC1. *Biochem. J.* 473: 1027-1035.
30. Akhmanova, A., and Steinmetz, M. O. 2015. Control of microtubule organization and dynamics: two ends in the limelight. *Nat. Rev. Mol. Cell Biol.* 16: 711-726.
31. Luconi, M. and Mannelli, M. 2012. Xenograft models for preclinical drug testing: Implications for adrenocortical cancer. *Molecular and Cellular Endocrinology* 351: 71-77.
32. Hollingshead, M. G. 2008. Antitumor efficacy testing in rodents. *J. Natl. Cancer Inst.* 100: 1500-1510.
33. Fiebig, H. H., Maier, A., Burger A. M. 2004. Clonogenic assay with established human tumour xenografts: correlation of in vitro to in vivo activity as a basis for anticancer drug discovery. *European J. Cancer* 40: 802-820.
34. Friedrich, J., Seidel, C., Ebner, R. and Kunz-Schughart, L. A. 2009. Spheroid-based drug screen: considerations and practical approach. *Nature protocols.* 4: 309-324.
35. Froehlich, K., Haeger, J., Heger, J., Pastuschek, J., Photini, S. M., Yan, Y., Lupp, A., Pfarrer, C., Mrowka, R., Schleussner, E., Markert, U. R. and Schmidt, A. 2016. Generation of multicellular breast cancer tumor spheroids: comparison of different protocols. *J. Mammary Gland Biol. Neoplasia* 21:89-98.
36. Zhang, Q., Re, Ko, N., Kwon, Oh, J. Recent advances in stimuli-responsive degradable block copolymer micelles: synthesis and controlled drug delivery applications. *Chem. Commun.* 48, 7542-7552.

The invention claimed is:
1. A method for selectively inhibiting growth in a cancer cell, comprising exposing said cancer cell to a compound, wherein said compound is chosen from
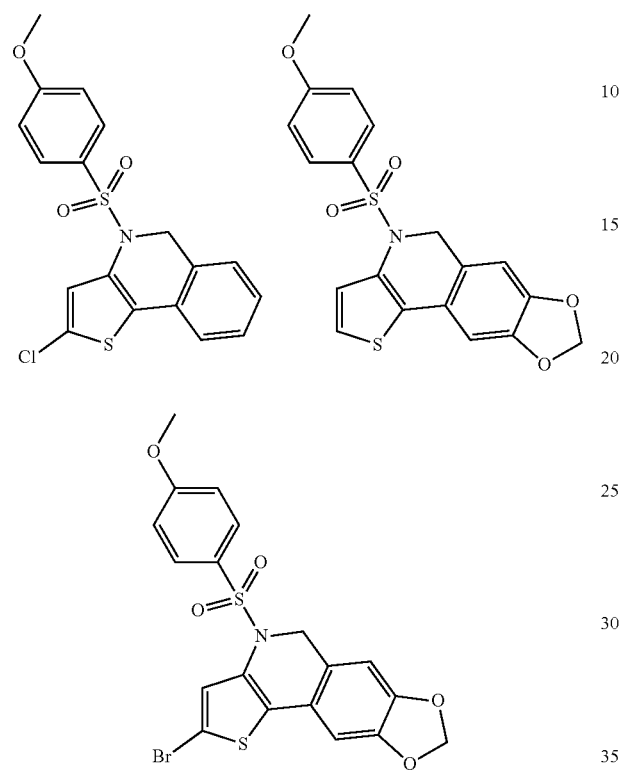
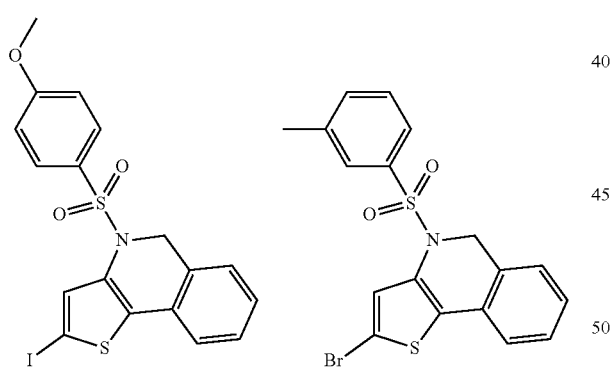
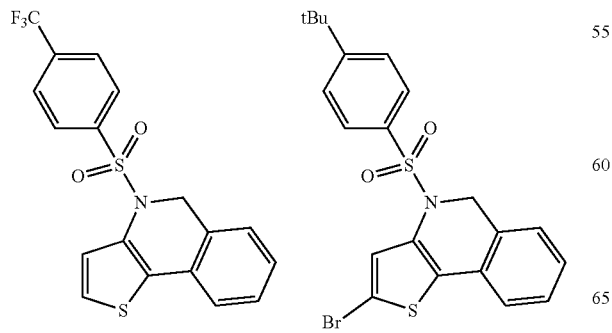
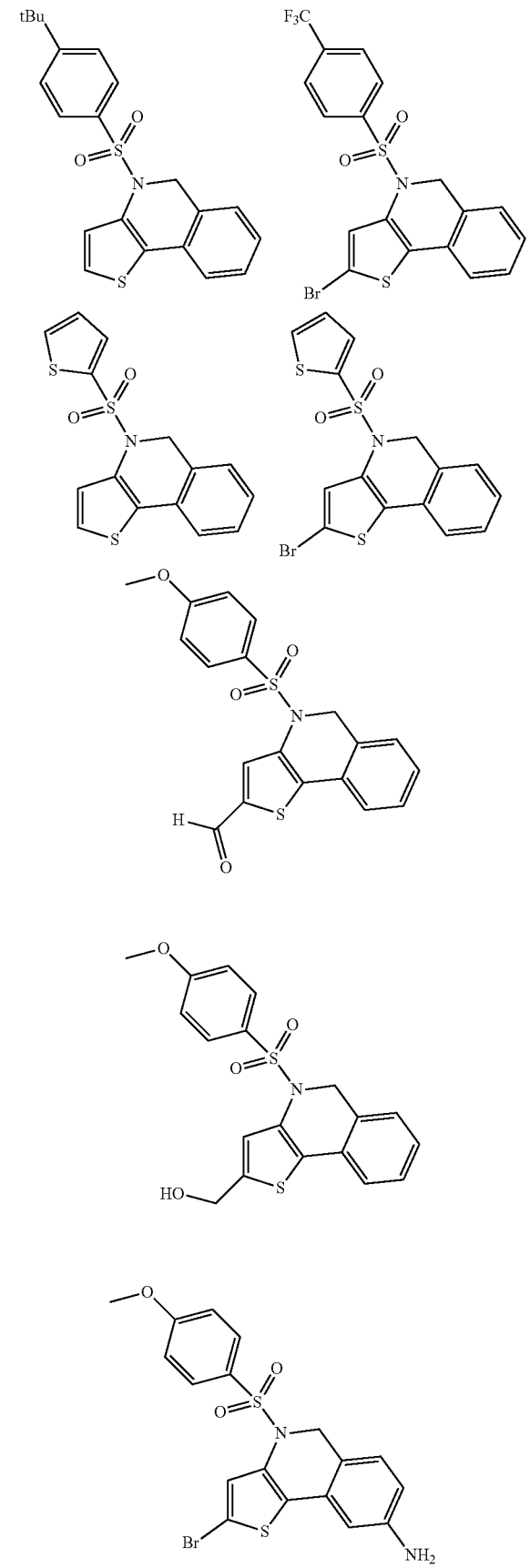

-continued
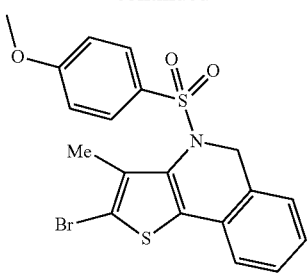
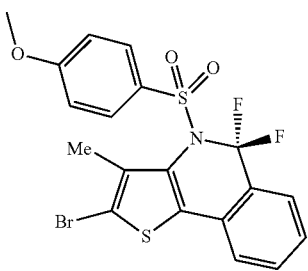
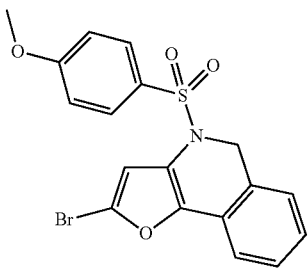
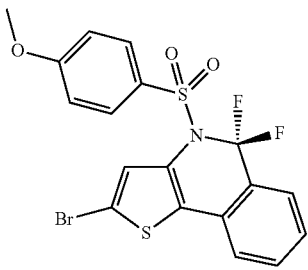
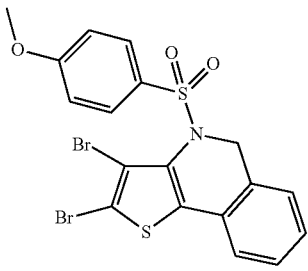
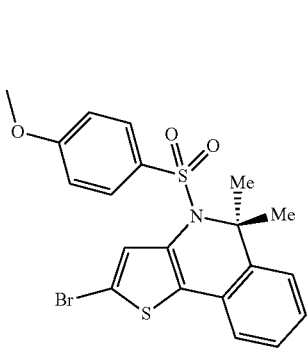
-continued
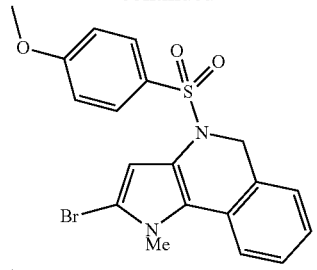
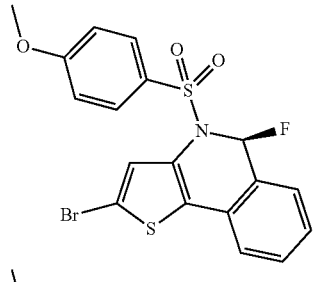
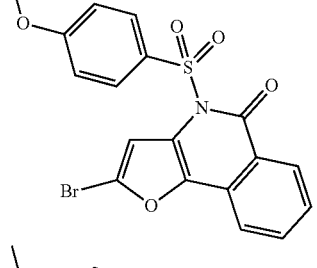
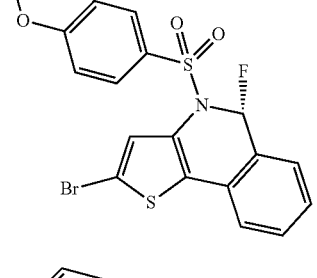
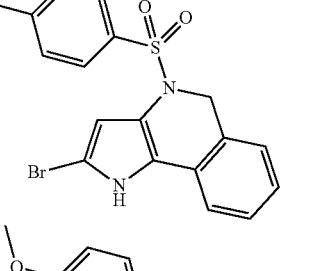 and
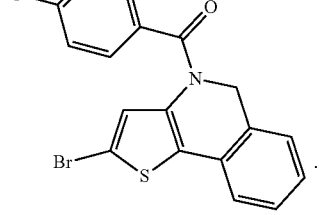.
2. The method of claim 1, wherein inhibiting growth comprises inducing mitotic arrest in said cancer cell.
3. The method of claim 1, comprising exposing said cancer cell to said compound having a concentration of about 1 nM, about 5 nM, about 100 nM, about 150 nM, about 200 nM, about 250 nM, about 300 nM, about 350 nM, about 400 nM, about 450 nM, about 500 nM, about 550 nM, about 600 nM, about 1000 nM, about 5000 nM or about 10000 nM.

4. The method of claim 1, comprising exposing said cancer cell to said compound for at least 1 minute, 2 minutes, 3 minutes, 4 minutes, 5 minutes, 10 minutes, 15 minutes, 20 minutes, 30 minutes, at least 45 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 24 hours, at least 30 hours or at least 36 hours.

5. The method of claim 1, wherein said cancer cell is a cancer cell with aberrant centrosomes.

6. The method of claim 1, wherein the cancer cell is a breast cancer cell, a cervical cancer cell, a non-small cell lung cancer cell, a pancreatic cancer cell, a colon cancer cell, a neuroblastoma cancer cell or an ovarian cancer cell.

7. The method of claim 1, wherein the cancer ell is a lung cancer cell or a colorectal cancer cell.

8. A method for selectively inhibiting growth in a cancer cell, comprising exposing said cancer cell to a compound, wherein said compound is

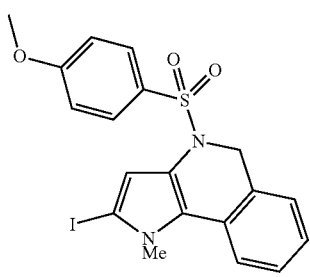

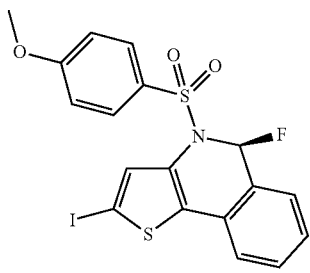

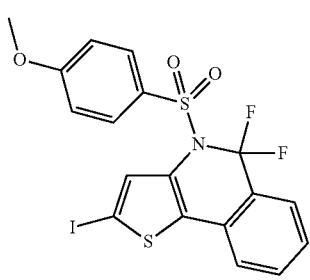

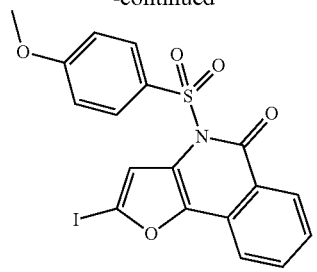

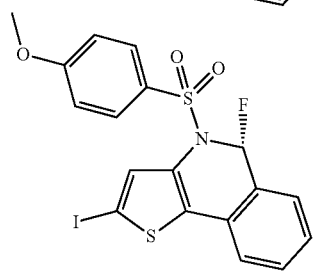

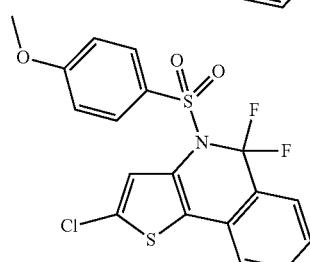

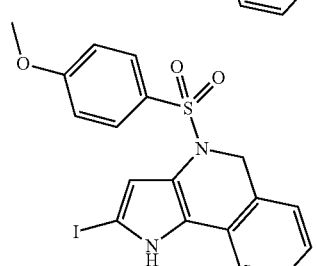

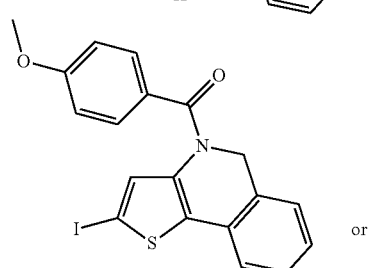

or

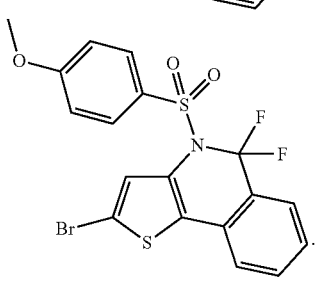

9. The method of claim 8, wherein inhibiting growth comprises inducing mitotic arrest in said cancer cell.

10. The method of claim 8, comprising exposing said cancer cell to said compound having a concentration of about 1 nM, about 5 nM, about 100 nM, about 150 nM, about 200 nM, about 250 nM, about 300 nM, about 350 nM, about 400 nM, about 450 nM, about 500 nM, about 550 nM, about 600 nM, about 1000 nM, about 5000 nM or about 10000 nM.

11. The method of claim 8, comprising exposing said cancer cell to said compound for at least 1 minute, 2 minutes, 3 minutes, 4 minutes, 5 minutes, 10 minutes, 15 minutes, 20 minutes, 30 minutes, at least 45 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 24 hours, at least 30 hours or at least 36 hours.

12. The method of claim 8, wherein said cancer cell is a cancer cell with aberrant centrosomes.

13. The method of claim 8, wherein the cancer cell is a breast cancer cell, a cervical cancer cell, a non-small cell lung cancer cell, a pancreatic cancer cell, a colon cancer cell, a neuroblastoma cancer cell or an ovarian cancer cell.

14. The method of claim 8, wherein the cancer cell is a lung cancer cell or a colorectal cancer cell.

* * * * *